US012691117B2

(12) United States Patent
Aronow et al.

(10) Patent No.: US 12,691,117 B2
(45) Date of Patent: Jul. 28, 2026

(54) KRAS INHIBITORS

(71) Applicant: ELI LILLY AND COMPANY, Indianapolis, IN (US)

(72) Inventors: Sean Aronow, Boulder, CO (US); Mario Barberis, Madrid (ES); Alexandra Bosnidou, Tres Cantos (ES); Desta Bume, Erie, CO (US); Xiaohong Chen, Carmel, IN (US); Sonia Maria Gutierrez Sanfeliciano, Carmel, IN (US); Timothy Scott Kercher, Longmont, CO (US); Wenceslao Lumeras Amador, Madrid (ES); Alicia Marcos Llorente, Moralzarzal (ES); Julian Priego Soler, Madrid (ES); Maria Lourdes Prieto Vallejo, Madrid (ES); Ramkumar Rajamani, Acton, MA (US); Isabel Rojo Garcia, Madrid (ES); William Rush Scaggs, Broomfield, CO (US); Victoriano Molero Flórez, Madrid (ES)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 19/324,975

(22) Filed: Sep. 10, 2025

(65) Prior Publication Data

US 2026/0166037 A1 Jun. 18, 2026

(30) Foreign Application Priority Data

Sep. 11, 2024 (EP) .................................... 24382971
Jul. 29, 2025 (EP) .................................... 25382789

(51) Int. Cl.
*A61K 31/517* (2006.01)
*A61K 31/519* (2006.01)

(52) U.S. Cl.
CPC .......... *A61K 31/517* (2013.01); *A61K 31/519* (2013.01)

(58) Field of Classification Search
CPC ............................ A61K 31/517; A61K 31/519
See application file for complete search history.

(56) References Cited

FOREIGN PATENT DOCUMENTS

| | | | |
|---|---|---|---|
| WO | 2021/118877 | A1 | 6/2021 |
| WO | 2022/261154 | A1 | 12/2022 |
| WO | 2023/183585 | A1 | 9/2023 |
| WO | 2024/206747 | A1 | 10/2024 |
| WO | 2024/206766 | A1 | 10/2024 |
| WO | 2025/072457 | A1 | 4/2025 |
| WO | 2025/092798 | A1 | 5/2025 |

OTHER PUBLICATIONS

PCT International Search Report and the Written Opinion of the International Searching Authority pertaining to international Application No. PCT/US2025/045670; Date of Mailing: Nov. 26, 2025; 13 pages.

*Primary Examiner* — Clinton A Brooks
*Assistant Examiner* — Jerica Katlynn Wilson
(74) *Attorney, Agent, or Firm* — Stefan Ochiana

(57) ABSTRACT

The present invention provides compounds of the formula:

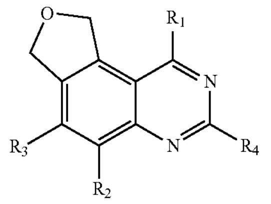

wherein $R_1$, $R_2$, $R_3$, and $R_4$ are as described herein, pharmaceutically acceptable salts thereof, and methods of using these compounds and pharmaceutically acceptable salts thereof for treating patients with cancer.

26 Claims, No Drawings

KRAS INHIBITORS

CROSS-REFERENCE TO RELATED PATENT APPLICATIONS

The present application claims the benefit of priority to European Patent Application Nos. EP 24382971.0, filed Sep. 11, 2024, and 25382789.3, filed on Jul. 29, 2025, the contents of which are incorporated herein by reference in their entireties.

FIELD

The present disclosure is directed to KRAS inhibitors useful in the treatment of diseases or disorders associated with KRAS modulation.

BACKGROUND

The MAPK/ERK signaling pathway relays extracellular stimuli to the nucleus, thereby regulating diverse cellular responses including cell proliferation, differentiation, and apoptosis. KRAS protein is an initiator of the MAPK/ERK signaling pathway and functions as a switch responsible for inducing cell division. In its inactive state, KRAS binds guanosine diphosphate (GDP), effectively sending a negative signal to suppress cell division. In response to an extracellular signal, KRAS is allosterically activated allowing for nucleotide exchange of GDP for guanosine triphosphate (GTP). In its GTP-bound active state, KRAS recruits and activates proteins necessary for the propagation of growth factor induced signaling, as well as other cell signaling receptors. Examples of the proteins recruited by KRAS-GTP are c-Raf and PI3-kinase. KRAS, as a GTP-ase, converts the bound GTP back to GDP, thereby returning itself to an inactive state, and again propagating signals to suppress cell division. KRAS gain of function mutations exhibit an increased degree of GTP binding and a decreased ability to convert GTP into GDP. The result is an increased MAPK/ERK signal which promotes cancerous cell growth. Missense mutations of KRAS at codon 12 are the most common mutations and markedly diminish GTPase activity.

Oncogenic KRAS mutations have been identified in approximately 30% of human cancers and have been demonstrated to activate multiple downstream signaling pathways. Despite the prevalence of KRAS mutations, it has been a difficult therapeutic target. (Cox, A. D. *Drugging the Undruggable RAS: Mission Possible*? Nat. Rev. Drug Disc. 2014, 13, 828-851; Pylayeva-Gupta, y et al. *RAS Oncogenes: Weaving a Tumorigenic Web.* Nat. Rev. Cancer 2011, 11, 761-774).

Thus far, work has focused on KRAS G12C mutant inhibitors (e.g., WO2019/099524, WO2020/081282, WO2020/101736, WO2020/146613, and WO2021/118877 disclose KRAS G12C inhibitors), whereas WO2021/041671 discloses small molecules inhibitors of KRAS G12D and WO2017/011920 discloses small molecule inhibitors of KRAS G12C, G12D, and G12V.

There remains a need to provide alternative, small molecule KRAS inhibitors. In particular, there is a need to provide orally deliverable KRAS inhibitors that are useful for treating cancer. More particularly, there is a need to provide small molecule inhibitors that specifically inhibit KRAS GTP activity. There is also a need to provide small molecule KRAS inhibitors that exhibit greater efficacy at the same or reduced KRAS inhibitory activity. Further, there is a desire to provide KRAS inhibitors that exhibit better pharmacokinetic/pharmacodynamic properties. Even further, there is a desire to provide KRAS inhibitors that exhibit good oral bioavailability and target coverage (KRAS G12V inhibition). Additionally, there is a need to provide KRAS inhibitors that exhibit selective inhibition preference for KRAS G12V mutant over KRAS wild-type and preferably also exhibit selective inhibition preference for KRAS G12V mutant over HRAS or NRAS. Also, there is a need to provide more potent KRAS inhibitors that exhibit increased efficacy with reduced or minimized untoward or undesired effects. The present invention addresses one or more of these needs by providing novel KRAS inhibitors.

SUMMARY

Compounds of Formula I are provided herein:

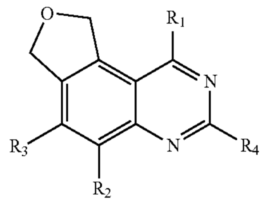

wherein:

$R_1$ is a group of the formula selected from

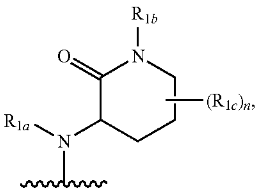

or

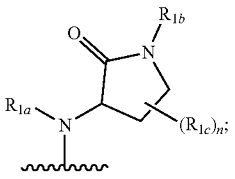

$R_{1a}$ is H, or a $C_{1-3}$ alkyl;

$R_{1b}$ is H, $C_{1-3}$ alkyl, or cyclopropyl;

n is 0, or 1;

$R_{1c}$ is a $C_{1-3}$ alkyl $R_2$ is H, halogen, or methyl;

$R_3$ is a group of the formula

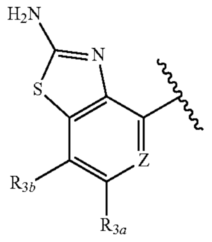

or

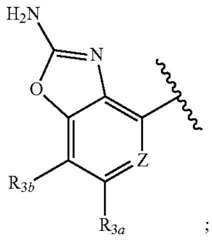

;

Z is —C($R_{3c}$)— or —N—;

$R_{3a}$, $R_{3b}$, and $R_{3c}$ are each independently H, halogen, or methyl;

$R_4$ is a group of the formula selected from

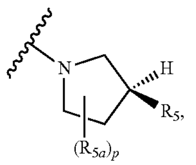
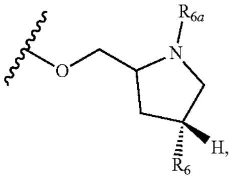
and
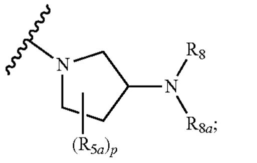

$R_5$ is —$NR_7R_{7a}$;
p is 0 or 1;
$R_{5a}$ and $R_{6a}$ are each independently a $C_{1-3}$ alkyl;
$R_6$ is a halogen or $C_{1-3}$ alkoxy;
$R_7$ is H or a $C_{1-3}$ alkyl;
$R_{7a}$ is a $C_{1-3}$ alkyl or $C_{1-3}$ alkoxy-$C_{1-3}$ alkyl; and
$R_8$ and $R_{8a}$ are each independently a $C_{1-3}$ alkyl; or
$R_8$ and $R_{8a}$ together with the nitrogen atom to which they are attached form an optionally substituted 4-, 5-, or 6-membered heterocycle optionally containing a further heteroatom selected from N, O, and S, wherein the heterocycle is optionally substituted with a $C_{1-3}$ alkyl;
or a pharmaceutically acceptable salt thereof.

Also provided herein are methods of using the compounds of Formula I, pharmaceutically acceptable salts thereof, and pharmaceutical compositions thereof, to treat cancer, in particular for the treatment of lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer. The methods include administering a therapeutically effective amount of a compound of Formula I, or a pharmaceutically acceptable salt thereof, to a patient in need thereof.

Further provided herein, are compounds of Formula I, and pharmaceutically acceptable salts thereof, for use in therapy. Additionally provided herein, are the compounds of Formula I, and pharmaceutically acceptable salts thereof, for use in the treatment of cancer, in particular for the treatment of lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer. Also additionally provided herein is the use of compounds of Formula I, or pharmaceutically acceptable salts thereof, in the manufacture of a medicament for treating cancer, in particular for the treatment of lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

DETAILED DESCRIPTION

Novel inhibitors of the KRAS gain of function mutation G12V are described herein. These new compounds could address the needs noted above for inhibitors of KRAS GTP activity in gain of function mutants in the treatment of cancers such as lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, or peritoneum cancer. Some of these new KRAS G12V mutant inhibitor compounds are selective to KRAS G12V mutants over wild-type KRAS, preferably they are also selective over hRAS and nRAS. Additionally, some of these new selective KRAS G12V mutant inhibitor compounds are also inhibitors of other mutant types such as KRAS G12C or G12D. Some of these new KRAS G12V mutant inhibitor compounds have good oral bioavailability and good target coverage (KRAS G12V mutant inhibition).

The present invention provides a compound of Formula I:

Formula I

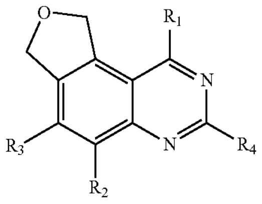

wherein $R_1$, $R_2$, $R_3$, and $R_4$ are as defined above, or a pharmaceutically acceptable salt thereof.

As used herein, the term halogen means fluoro (F), chloro (Cl), bromo (Br), or iodo (I). As used herein, the term alkyl means saturated linear or branched-chain monovalent hydrocarbon radicals of one to a specified number of carbon atoms, e.g., "$C_{1-4}$ alkyl" or "$C_{1-3}$ alkyl." Examples of alkyls include, but are not limited to, methyl, ethyl, propyl, 1-propyl, isopropyl, butyl, and iso-butyl.

In an embodiment of a compound of Formula I or a pharmaceutically acceptable salt thereof, $R_3$ is a group of the formula

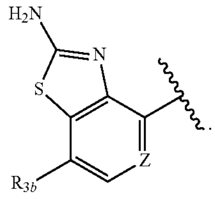

In an embodiment of a compound of Formula I or a pharmaceutically acceptable salt thereof, $R_3$ is a group of the formula

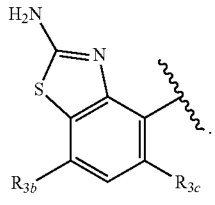

In an embodiment of a compound of Formula I or a pharmaceutically acceptable salt thereof, $R_3$ is a group of the formula

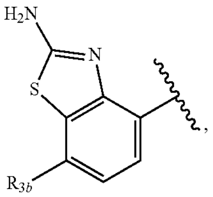

wherein preferably $R_{3b}$ is F or Cl, most preferably $R_{3b}$ is F.

In an embodiment of a compound of Formula I or a pharmaceutically acceptable salt thereof, $R_3$ is a group of the formula

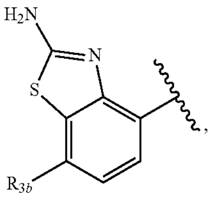

wherein preferably $R_{3b}$ is H.

In an embodiment of a compound of Formula I or a pharmaceutically acceptable salt thereof, $R_3$ is a group of the formula

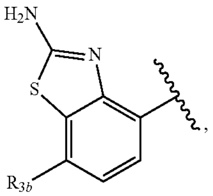

wherein preferably $R_{3b}$ is methyl.

In an embodiment of a compound of Formula I or a pharmaceutically acceptable salt thereof, $R_3$ is a group of the formula

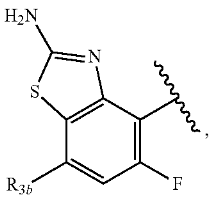

wherein preferably $R_{3b}$ is H or F.

In an embodiment of a compound of Formula I or a pharmaceutically acceptable salt thereof, $R_3$ is a group of the formula

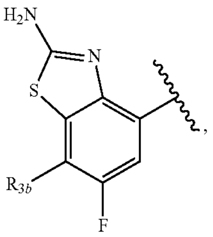

wherein preferably $R_{3b}$ is H.

In an embodiment of a compound of Formula I or a pharmaceutically acceptable salt thereof, $R_3$ is a group of the formula

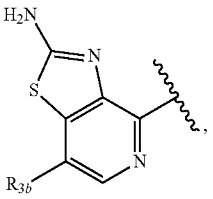

wherein preferably $R_{3b}$ is F.

In an embodiment of a compound of Formula I or a pharmaceutically acceptable salt thereof, $R_3$ is a group of the formula selected from

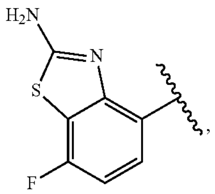

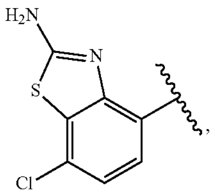

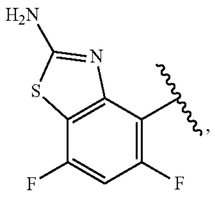

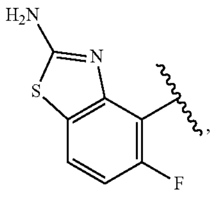

or

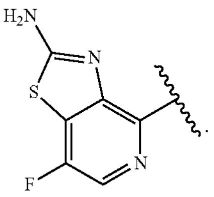

In an embodiment of a compound of Formula I or a pharmaceutically acceptable salt thereof, $R_3$ is a group of the formula selected from

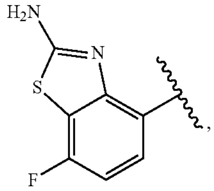,
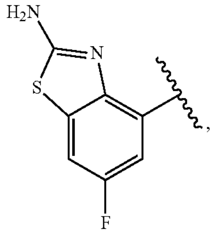,
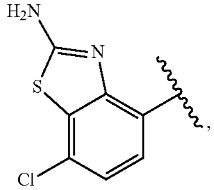,
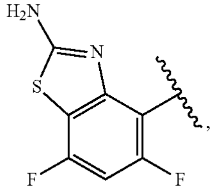,
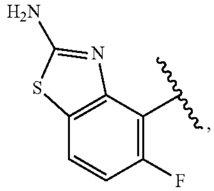,
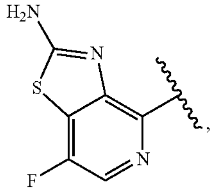,
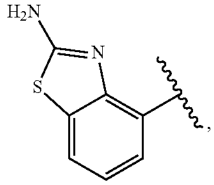, and
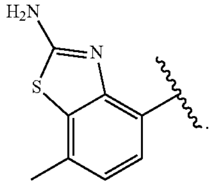.

In an embodiment of a compound of Formula I or a pharmaceutically acceptable salt thereof, $R_3$ is a group of the formula

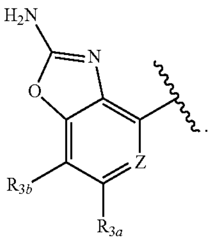.

In an embodiment of a compound of Formula I or a pharmaceutically acceptable salt thereof, $R_3$ is a group of the formula

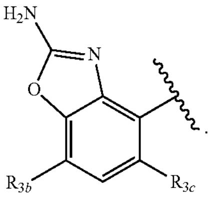.

In an embodiment of a compound of Formula I or a pharmaceutically acceptable salt thereof, $R_3$ is a group of the formula

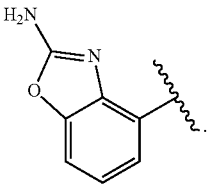 [SMILES: *c1cccc2oc(N)nc12].

In an embodiment of a compound of Formula I or a pharmaceutically acceptable salt thereof, $R_2$ is F or Cl.

In an embodiment of a compound of Formula I, or a pharmaceutically acceptable salt thereof, $R_2$ is F.

In an embodiment of a compound of Formula I, or a pharmaceutically acceptable salt thereof, $R_2$ is Cl.

In an embodiment of a compound of Formula I or a pharmaceutically acceptable salt thereof, $R_1$ is a group of the formula

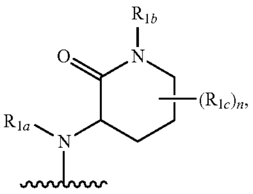

In an embodiment of a compound of Formula I or a pharmaceutically acceptable salt thereof, $R_1$ is a group of the formula

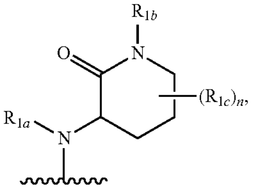

wherein $R_{1a}$ is H.

In an embodiment of a compound of Formula I or a pharmaceutically acceptable salt thereof, $R_1$ is a group of the formula

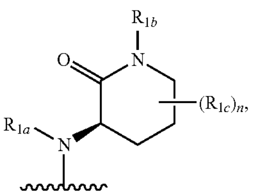

wherein $R_{1a}$ is preferably H.

In an embodiment of a compound of Formula I or a pharmaceutically acceptable salt thereof, $R_1$ is a group of the formula

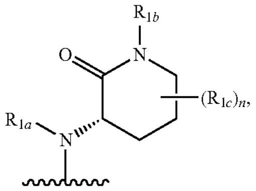

wherein $R_{1a}$ is preferably H.

In an embodiment of a compound of Formula I or a pharmaceutically acceptable salt thereof, $R_{1a}$ is H.

In an embodiment of a compound of Formula I or a pharmaceutically acceptable salt thereof, $R_{1b}$ is H, methyl, ethyl, isopropyl, or cyclopropyl.

In an embodiment of a compound of Formula I or a pharmaceutically acceptable salt thereof, $R_{1b}$ is H, or methyl, preferably $R_{1b}$ is methyl.

In an embodiment of a compound of Formula I or a pharmaceutically acceptable salt thereof, $R_{1b}$ is a $C_{1-3}$ alkyl.

In an embodiment of a compound of Formula I or a pharmaceutically acceptable salt thereof, n is 0.

In an embodiment of a compound of Formula I or a pharmaceutically acceptable salt thereof, n is 1 and $R_{1c}$ is a $C_{1-3}$ alkyl, preferably $R_{1c}$ is methyl.

In an embodiment of a compound of Formula I or a pharmaceutically acceptable salt thereof, $R_{1a}$ is H, $R_{1b}$ is a $C_{1-3}$ alkyl, and n is 0.

In an embodiment of a compound of Formula I or a pharmaceutically acceptable salt thereof, $R_1$ is a group of the formula

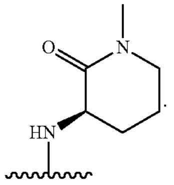 [SMILES: *N[C@@H]1CCCN(C)C1=O]

In an embodiment of a compound of Formula I or a pharmaceutically acceptable salt thereof, $R_{1a}$ is H, $R_{1b}$ is a $C_{1-3}$ alkyl, n is 1 and $R_{1c}$ is a $C_{1-3}$ alkyl, preferably $R_{1b}$ and $R_{1c}$ are methyl.

In an embodiment of a compound of Formula I or a pharmaceutically acceptable salt thereof, $R_1$ is a group of the formula selected from

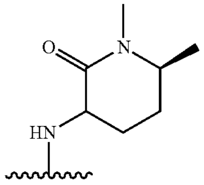

or

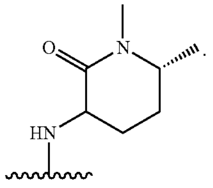

In an embodiment of a compound of Formula I or a pharmaceutically acceptable salt thereof, $R_1$ is a group of the formula selected from

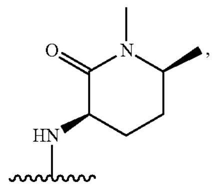

, or

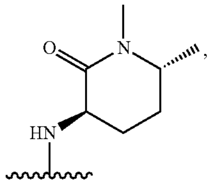

In an embodiment of a compound of Formula I or a pharmaceutically acceptable salt thereof, $R_1$ is a group of the formula

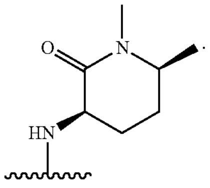 [SMILES: *N[C@@H]1CC[C@H](C)N(C)C1=O]

In an embodiment of a compound of Formula I or a pharmaceutically acceptable salt thereof, $R_1$ is a group of the formula selected from

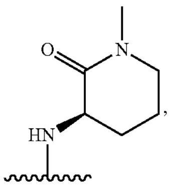

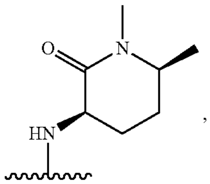

,

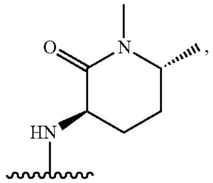

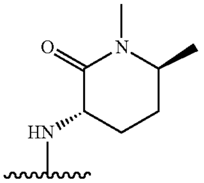

or

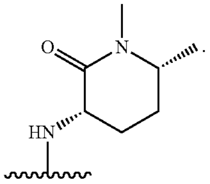

In an embodiment of a compound of Formula I or a pharmaceutically acceptable salt thereof, $R_1$ is a group of the formula selected from

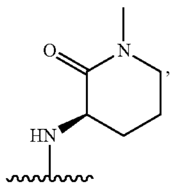

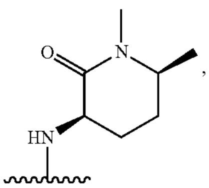

, or

-continued

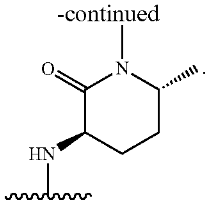

In an embodiment of a compound of Formula I or a pharmaceutically acceptable salt thereof, $R_4$ is a group of the formula

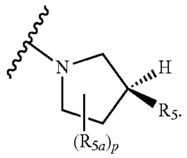

In an embodiment of a compound of Formula I or a pharmaceutically acceptable salt thereof, $R_4$ is a group of the formula

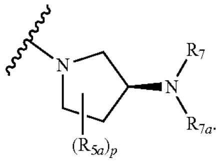

In an embodiment of a compound of Formula I or a pharmaceutically acceptable salt thereof, $R_7$ is H or a $C_{1-3}$ alkyl, preferably $R_7$ is H.

In an embodiment of a compound of Formula I or a pharmaceutically acceptable salt thereof, $R_7$ is selected from H, methyl, ethyl, and isopropyl.

In an embodiment of a compound of Formula I or a pharmaceutically acceptable salt thereof, $R_7$ is methyl or ethyl.

In an embodiment of a compound of Formula I or a pharmaceutically acceptable salt thereof, $R_7$ is methyl.

In an embodiment of a compound of Formula I or a pharmaceutically acceptable salt thereof, $R_7$ is ethyl.

In an embodiment of a compound of Formula I or a pharmaceutically acceptable salt thereof, $R_{7a}$ is selected from methyl, ethyl, isopropyl, and methoxyethyl.

In an embodiment of a compound of Formula I or a pharmaceutically acceptable salt thereof, $R_{7a}$ is methyl.

In an embodiment of a compound of Formula I or a pharmaceutically acceptable salt thereof, $R_{7a}$ is ethyl.

In an embodiment of a compound of Formula I or a pharmaceutically acceptable salt thereof, $R_{7a}$ is isopropyl.

In an embodiment of a compound of Formula I or a pharmaceutically acceptable salt thereof, $R_{7a}$ is methoxyethyl.

In an embodiment of a compound of Formula I or a pharmaceutically acceptable salt thereof, p is 0.

In an embodiment of a compound of Formula I or a pharmaceutically acceptable salt thereof, p is 1.

In an embodiment of a compound of Formula I or a pharmaceutically acceptable salt thereof, $R_5$ is methyl, $R_7$ is H, $R_{7a}$ is isopropyl, and p is 1.

In an embodiment of a compound of Formula I or a pharmaceutically acceptable salt thereof, $R_5$, $R_7$, and $R_{7a}$ are each methyl, and p is 1.

In an embodiment of a compound of Formula I or a pharmaceutically acceptable salt thereof, $R_5$ is methyl, $R_7$ is methyl, $R_{7a}$ is ethyl, and p is 1.

In an embodiment of a compound of Formula I or a pharmaceutically acceptable salt thereof, $R_5$ and $R_7$ are each methyl, $R_{7a}$ is ethyl, and p is 1.

In an embodiment of a compound of Formula I or a pharmaceutically acceptable salt thereof, $R_5$ is methyl, $R_7$ and $R_{7a}$ are each ethyl, and p is 1.

In an embodiment of a compound of Formula I or a pharmaceutically acceptable salt thereof, $R_5$ and $R_7$ are each methyl, $R_{7a}$ is isopropyl, and p is 1.

In an embodiment of a compound of Formula I or a pharmaceutically acceptable salt thereof, $R_7$ and $R_{7a}$ are each ethyl, and p is 0.

In an embodiment of a compound of Formula I or a pharmaceutically acceptable salt thereof, $R_5$ and $R_{7a}$ are each methyl, $R_7$ is methoxyethyl, and p is 1.

In an embodiment of a compound of Formula I or a pharmaceutically acceptable salt thereof, $R_4$ is a group of the formula selected from

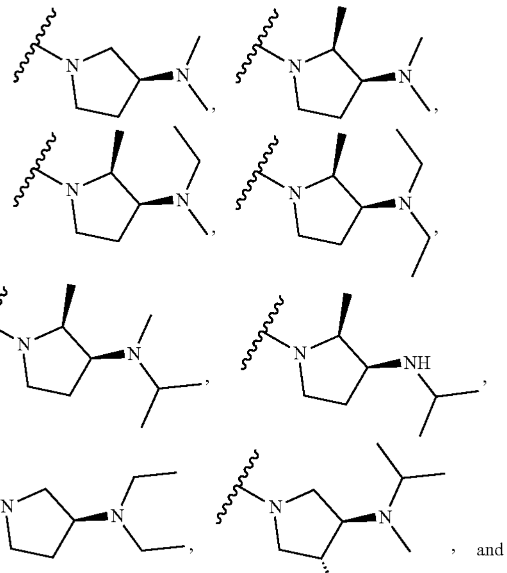

and

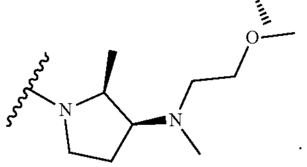

In an embodiment of a compound of Formula I or a pharmaceutically acceptable salt thereof, $R_4$ is a group of the formula selected from

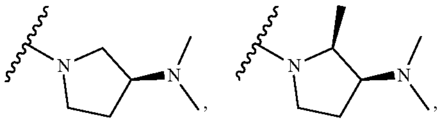

-continued

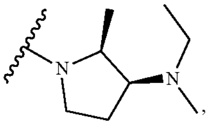, 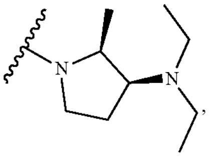,

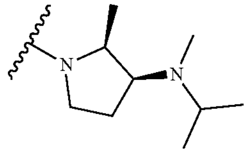, or 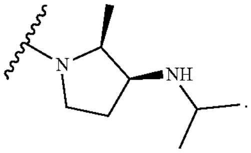.

In an embodiment of a compound of Formula I or a pharmaceutically acceptable salt thereof, $R_4$ is a group of the formula

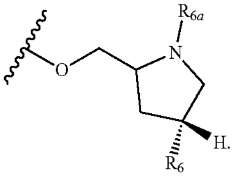

In an embodiment of a compound of Formula I or a pharmaceutically acceptable salt thereof, $R_{6a}$ is selected from methyl, ethyl, and isopropyl, preferably $R_{6a}$ is methyl.

In an embodiment of a compound of Formula I or a pharmaceutically acceptable salt thereof, $R_6$ is halogen or $C_{1-3}$ alkoxy.

In an embodiment of a compound of Formula I or a pharmaceutically acceptable salt thereof, $R_6$ is F.

In an embodiment of a compound of Formula I or a pharmaceutically acceptable salt thereof, $R_6$ is methoxy.

In an embodiment of a compound of Formula I or a pharmaceutically acceptable salt thereof, $R_4$ is a group of the formula selected from

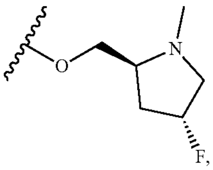, 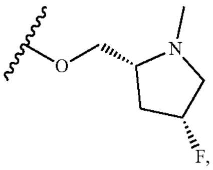, and

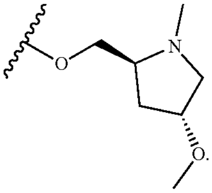

In an embodiment of a compound of Formula I or a pharmaceutically acceptable salt thereof, $R_4$ is a group of the formula selected from

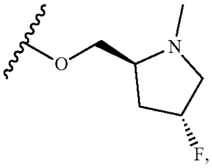, or 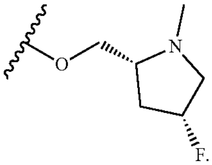

In an embodiment of a compound of Formula I or a pharmaceutically acceptable salt thereof, $R_4$ is a group of the formula

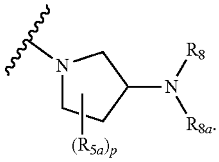

In an embodiment of a compound of Formula I or a pharmaceutically acceptable salt thereof, $R_4$ is a group of the formula

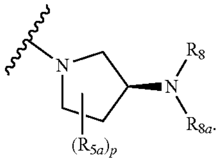

In an embodiment of a compound of Formula I or a pharmaceutically acceptable salt thereof, $R_4$ is a group of the formula

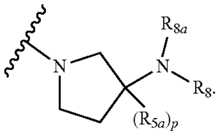

In an embodiment of a compound of Formula I or a pharmaceutically acceptable salt thereof, $R_8$ and $R_{8a}$ are each independently a $C_{1-3}$ alkyl.

In an embodiment of a compound of Formula I or a pharmaceutically acceptable salt thereof, $R_8$ is methyl and $R_{8a}$ is ethyl.

In an embodiment of a compound of Formula I or a pharmaceutically acceptable salt thereof, $R_8$ and $R_{8a}$ together with the nitrogen atom to which they are attached form an optionally substituted 4-, 5-, or 6-membered heterocycle optionally containing a further heteroatom selected from N, O, and S, wherein the heterocycle is optionally substituted with a $C_{1-3}$ alkyl.

In an embodiment of a compound of Formula I or a pharmaceutically acceptable salt thereof, $R_8$ and $R_{8a}$ together with the nitrogen atom to which they are attached form a 4- or 5-membered heterocycle optionally containing a further heteroatom selected from N, O, and S.

In an embodiment of a compound of Formula I or a pharmaceutically acceptable salt thereof, $R_{5a}$ is methyl or ethyl, preferably methyl.

In an embodiment of a compound of Formula I or a pharmaceutically acceptable salt thereof, p is 1.

In an embodiment of a compound of Formula I or a pharmaceutically acceptable salt thereof, p is 0.

In an embodiment of a compound of Formula I or a pharmaceutically acceptable salt thereof, $R_8$ and $R_{8a}$ are each ethyl, and p is 0.

In an embodiment of a compound of Formula I or a pharmaceutically acceptable salt thereof, $R_5$ is methyl, $R_8$ and $R_{8a}$ together with the nitrogen atom to which they are attached form a 4-membered heterocycle, and p is 1.

In an embodiment of a compound of Formula I or a pharmaceutically acceptable salt thereof, $R_5$ is methyl, $R_8$ and $R_{8a}$ together with the nitrogen atom to which they are attached form a 5-membered heterocycle, and p is 1.

In an embodiment of a compound of Formula I or a pharmaceutically acceptable salt thereof, $R_4$ is a group of the formula selected from

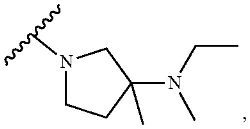,
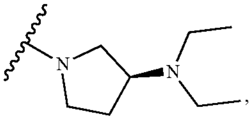,
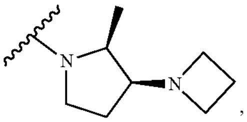, and
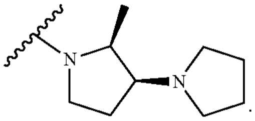.

In an embodiment of a compound of Formula I or a pharmaceutically acceptable salt thereof, $R_4$ is a group of the formula selected from

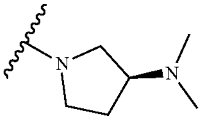,
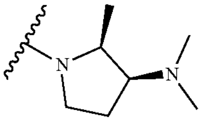,
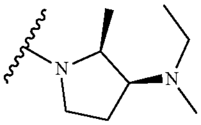,
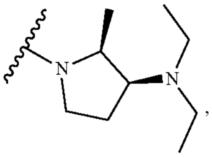,
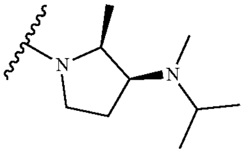,
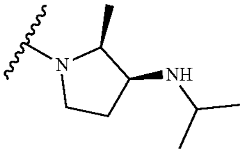,
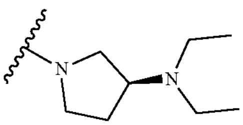,
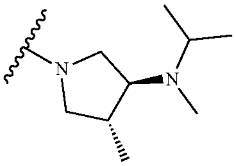,
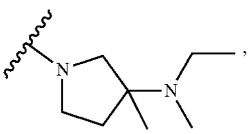,
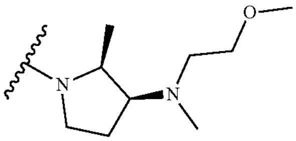

-continued

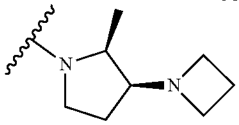,
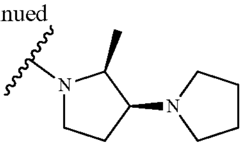,
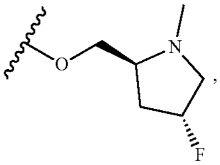,
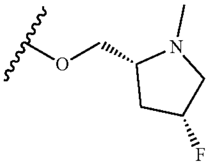, and
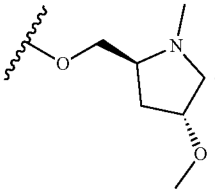.

In an embodiment of a compound of Formula I or a pharmaceutically acceptable salt thereof, $R_4$ is a group of the formula selected from

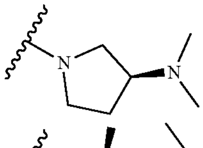,
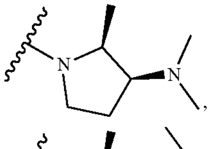,
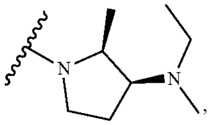,
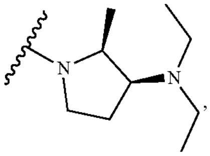,
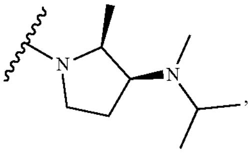,
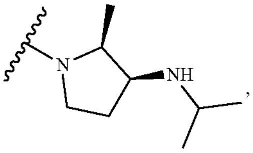,
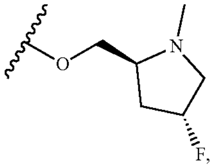, or
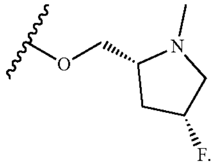.

In the above embodiments of the compounds of Formula I, the chemical drawings are shown flat without chiral information. These compounds often have multiple chiral centers and are contemplated to exist in various forms with various combinations of chiral centers. Additionally, these compounds have various enantiomers, diastereomers, and atropisomers that can exist and are included herein.

In an embodiment of a compound of Formula I or a pharmaceutically acceptable salt thereof, the compound is an isotopic derivative of any one of the compounds described herein or a pharmaceutically acceptable salt thereof.

It is understood that the isotopic derivative can be prepared using any of a variety of art-recognized techniques. For example, the isotopic derivatives can generally be prepared by carrying out the procedures disclosed in the schemes and/or in the examples described herein or a pharmaceutically acceptable salt thereof, by substituting an isotopically labeled reagent for a non-isotopically labeled reagent.

In a further embodiment of a compound of Formula I or a pharmaceutically acceptable salt thereof, the compound may be deuterated at one or more positions. Unless otherwise stated, when an atom is designated specifically as "H" or "hydrogen", the atom is understood to have hydrogen at its natural abundance isotopic composition. Also, unless otherwise stated, when an atom is designated specifically as "D" or "deuterium", the atom is understood to have deuterium at an abundance substantially greater than the natural abundance of deuterium, which is 0.015%.

In an embodiment of a compound of Formula I or a pharmaceutically acceptable salt thereof, the compound is a deuterium labeled compound of any one of the compounds described herein and pharmaceutically acceptable salts thereof.

The following are further numbered embodiments of the invention:

1. A compound of the formula:

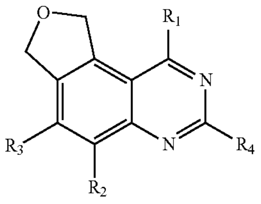

wherein:

$R_1$ is a group of the formula

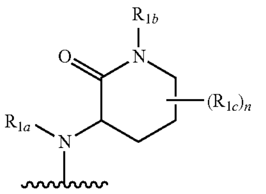

or

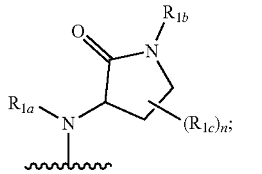

$R_{1a}$ is H or a $C_{1-3}$ alkyl;

$R_{1b}$ is H, $C_{1-3}$ alkyl, or cyclopropyl;

n is 0 or 1;

$R_{1c}$ is a $C_{1-3}$ alkyl $R_2$ is H, halogen, or methyl;

$R_3$ is a group of the formula

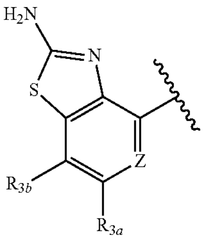

or

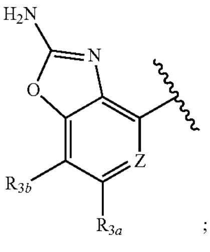

;

Z is —C($R_{3c}$)— or —N—;

$R_{3a}$, $R_{3b}$, and $R_{3c}$ are each independently H, halogen, or methyl;

$R_4$ is a group of the formula

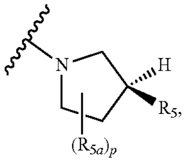

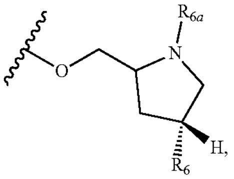

or

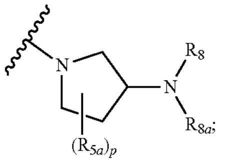

$R_5$ is —$NR_7R_{7a}$;

p is 0 or 1;

$R_{5a}$ and $R_{6a}$ are each independently a $C_{1-3}$ alkyl;

$R_6$ is a halogen or $C_{1-3}$ alkoxy;

$R_7$ is H or a $C_{1-3}$ alkyl;

$R_{7a}$ is a $C_{1-3}$ alkyl or $C_{1-3}$ alkoxy-$C_{1-3}$ alkyl; and $R_8$ and $R_{8a}$ are each independently a $C_{1-3}$ alkyl; or $R_8$ and $R_{8a}$ together with the nitrogen atom to which they are attached form an optionally substituted 4-, 5-, or 6-membered heterocycle optionally containing a further heteroatom selected from N, O, and S, wherein the heterocycle is optionally substituted with a $C_{1-3}$ alkyl;

or a pharmaceutically acceptable salt thereof.

2. A compound of the formula:

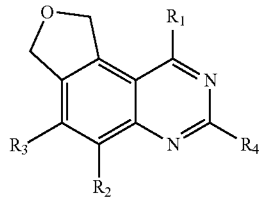

wherein:

$R_1$ is a group of the formula selected from

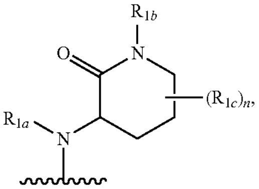

or

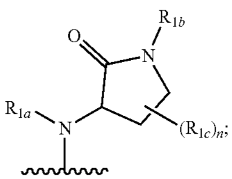

$R_{1a}$ is H, or a $C_{1-3}$ alkyl;

$R_{1b}$ is H, $C_{1-3}$ alkyl, or cyclopropyl;

n is 0, or 1;

$R_{1c}$ is a $C_{1-3}$ alkyl $R_2$ is H, halogen, or methyl;

$R_3$ is a group of the formula

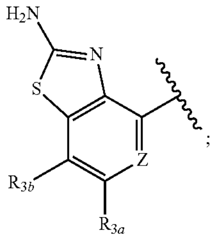

Z is —$C(R_{3c})$— or —N—;

$R_{3a}$, $R_{3b}$, and $R_{3c}$ are each independently H, halogen, or methyl;

$R_4$ is a group of the formula selected from

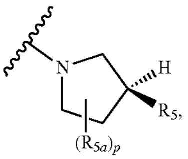

or

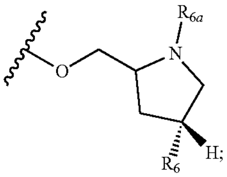

$R_5$ is —$NR_7R_{7a}$;

p is 0 or 1;

$R_{5a}$ and $R_{6a}$ are each independently a $C_{1-3}$ alkyl;

$R_6$ is a halogen;

$R_7$ is H or a $C_{1-3}$ alkyl; and $R_{7a}$ is a $C_{1-3}$ alkyl; or a pharmaceutically acceptable salt thereof.

3. The compound according to embodiment 1 or 2, wherein $R_3$ is a group of the formula

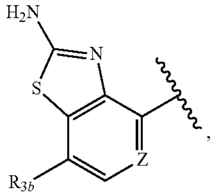

or a pharmaceutically acceptable salt thereof.

4. The compound according to embodiment 3, wherein $R_3$ is a group of the formula

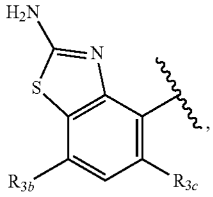

or a pharmaceutically acceptable salt thereof.

5. The compound according to embodiment 3, wherein $R_3$ is a group of the formula

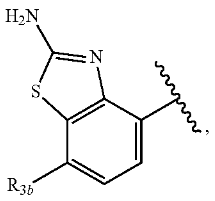

wherein preferably $R_{3b}$ is F or Cl, most preferably $R_{3b}$ is F, or a pharmaceutically acceptable salt thereof.

6. The compound according to embodiment 3, wherein $R_3$ is a group of the formula

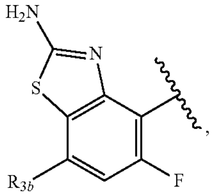

wherein preferably $R_{3b}$ is H or F, most preferably $R_{3b}$ is H, or a pharmaceutically acceptable salt thereof.

7. The compound according to embodiment 3, wherein $R_3$ is a group of the formula

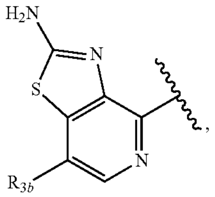

wherein preferably $R_{3b}$ is F, or a pharmaceutically acceptable salt thereof.

8. The compound according to embodiment 3, wherein $R_3$ is a group of the formula

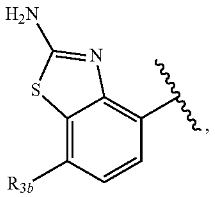

wherein preferably $R_{3b}$ is H, or a pharmaceutically acceptable salt thereof.

9. The compound according to embodiment 3, wherein $R_3$ is a group of the formula

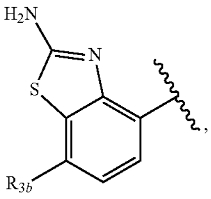, wherein preferably $R_{3b}$ is methyl, or a pharmaceutically acceptable salt thereof.

10. The compound according to embodiment 3, wherein $R_3$ is a group of the formula

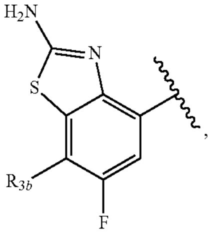, wherein preferably $R_{3b}$ is H, or a pharmaceutically acceptable salt thereof.

11. The compound according to embodiment 3, wherein $R_3$ is a group of the formula selected from

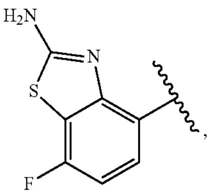,
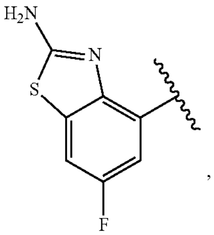,
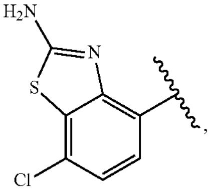,
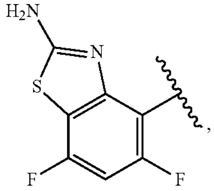,
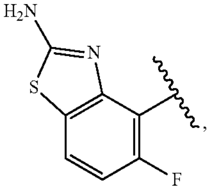,
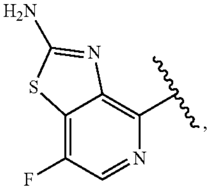,
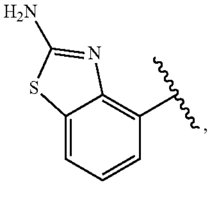, and
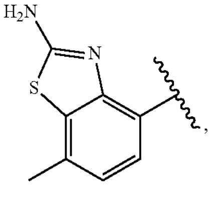, or a pharmaceutically acceptable salt thereof.

12. The compound according to embodiment 3, wherein $R_3$ is a group of the formula selected from

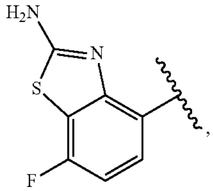,
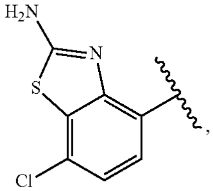,
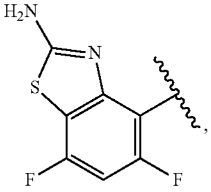,
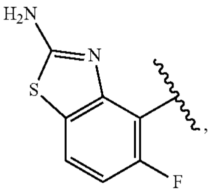, and
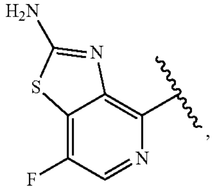, or a pharmaceutically acceptable salt thereof.

13. The compound according to embodiment 1, wherein $R_3$ is a group of the formula

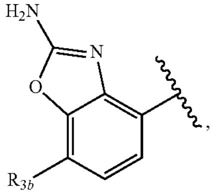, wherein preferably $R_{3b}$ is H, or a pharmaceutically acceptable salt thereof.

14. The compound according to embodiment 1 or 13, wherein $R_3$ is a group of the formula

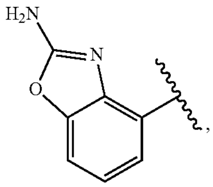, or a pharmaceutically acceptable salt thereof.

15. The compound according to any one of embodiments 1-14, wherein $R_2$ is F or Cl, or a pharmaceutically acceptable salt thereof.

16. The compound according to embodiment 15, wherein $R_2$ is F, or a pharmaceutically acceptable salt thereof.

17. The compound according to embodiment 15, wherein $R_2$ is Cl, or a pharmaceutically acceptable salt thereof.

18. The compound according to any one of embodiments 1-17, wherein $R_1$ is a group of the formula

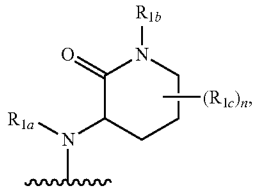

or a pharmaceutically acceptable salt thereof.

19. The compound according to embodiment 18, wherein $R_1$ is a group of the formula

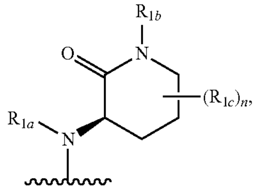

or a pharmaceutically acceptable salt thereof.

20. The compound according to embodiment 18, wherein $R_1$ is a group of the formula

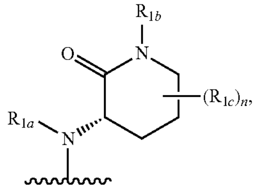

or a pharmaceutically acceptable salt thereof.

21. The compound according to any one of embodiments 1-20, wherein $R_{1a}$ is H, or a pharmaceutically acceptable salt thereof.

22. The compound according to any one of embodiments 1-21, wherein $R_{1b}$ is H, methyl, ethyl, isopropyl, or cyclopropyl, or a pharmaceutically acceptable salt thereof.

23. The compound according to any one of embodiments 1-22, wherein $R_{1b}$ is H, or methyl, preferably $R_{1b}$ is methyl, or a pharmaceutically acceptable salt thereof.

24. The compound according to any one of embodiments 18-23, wherein n is 0, or a pharmaceutically acceptable salt thereof.

25. The compound according to any one of embodiments 18-23, wherein n is 1 and $R_{1c}$ is a $C_{1-3}$ alkyl, preferably $R_{1c}$ is methyl, or a pharmaceutically acceptable salt thereof.

26. The compound according to any one of embodiments 1-20, wherein $R_{1a}$ is H, $R_{1b}$ is a CI-3 alkyl, and n is 0, or a pharmaceutically acceptable salt thereof.

27. The compound according to embodiment 26, wherein $R_1$ is a group of the formula

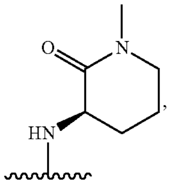 [SMILES: *N[C@@H]1CCCN(C)C1=O]

or a pharmaceutically acceptable salt thereof.

28. The compound according to any one of embodiments 1-20, wherein $R_{1a}$ is H, $R_{1b}$ is a CI-3 alkyl, n is 1, and $R_{1c}$ is a $C_{1-3}$ alkyl, preferably $R_{1b}$ and $R_{1c}$ are methyl, or a pharmaceutically acceptable salt thereof.

29. The compound according to embodiment 28, wherein $R_1$ is a group of the formula selected from

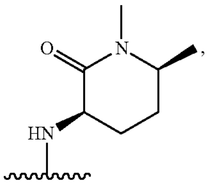 or 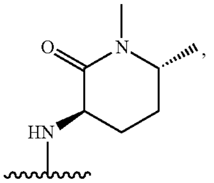

or a pharmaceutically acceptable salt thereof.

30. The compound according to embodiment 28, wherein $R_1$ is a group of the formula

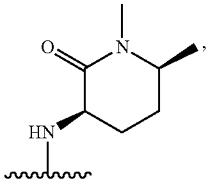 [SMILES: *N[C@@H]1CC[C@H](C)N(C)C1=O]

or a pharmaceutically acceptable salt thereof.

31. The compound according to embodiment 18, wherein $R_1$ is a group of the formula selected from

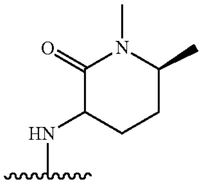 or 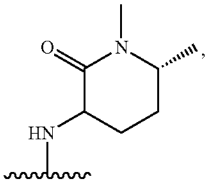

or a pharmaceutically acceptable salt thereof.

32. The compound according to embodiment 18, wherein $R_1$ is a group of the formula selected from

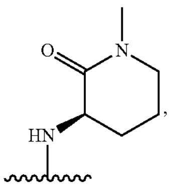 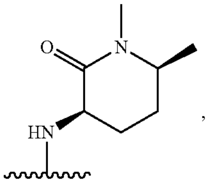

-continued

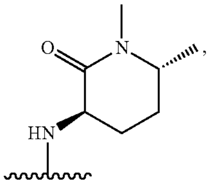

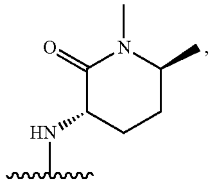

or

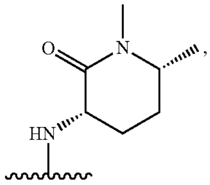

or a pharmaceutically acceptable salt thereof.

33. The compound according to embodiment 18, wherein $R_1$ is a group of the formula selected from

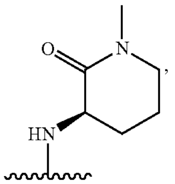

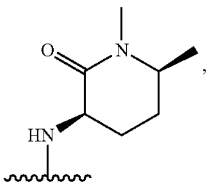

or

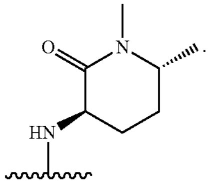

or a pharmaceutically acceptable salt thereof.

34. The compound according to any one of embodiments 1-33, wherein $R_4$ is a group of the formula

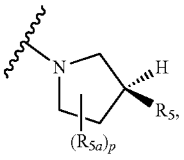

or a pharmaceutically acceptable salt thereof.

35. The compound according to any one of embodiments 1-34, wherein $R_4$ is a group of the formula

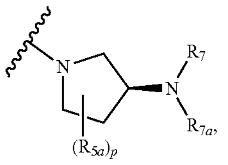

or a pharmaceutically acceptable salt thereof.

36. The compound according to embodiment 34 or 35, wherein $R_4$ is a group of the formula selected from

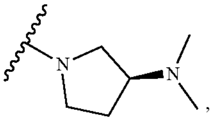

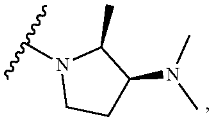

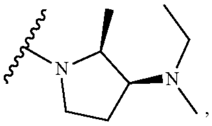

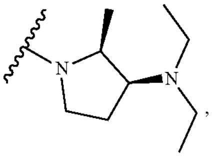

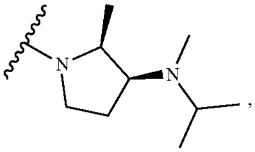

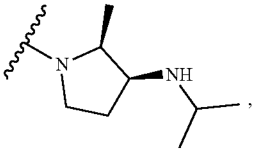

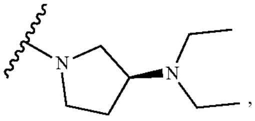

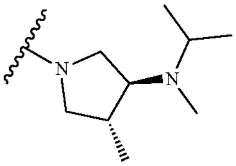

, and

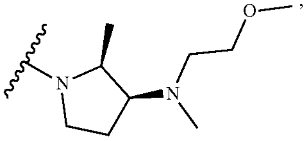

or a pharmaceutically acceptable salt thereof.

37. The compound according to embodiment 36, wherein $R_4$ is a group of the formula selected from

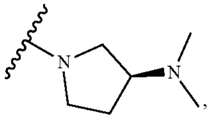

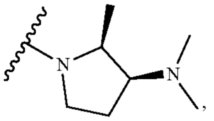

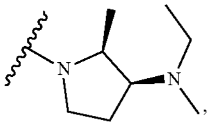

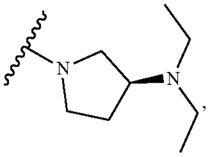

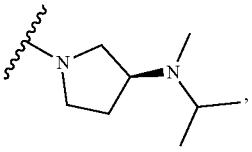

or

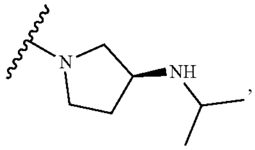

or a pharmaceutically acceptable salt thereof.

38. The compound according to any one of embodiments 1-33, wherein $R_4$ is a group of the formula

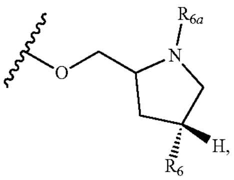

or a pharmaceutically acceptable salt thereof.

39. The compound according to embodiment 38, wherein $R_4$ is a group of the formula selected from

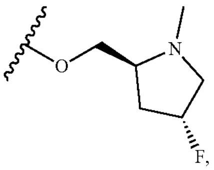
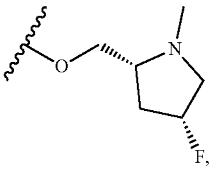
and
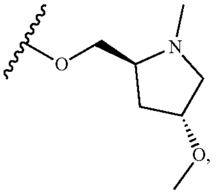

or a pharmaceutically acceptable salt thereof.

40. The compound according to embodiment 39, wherein $R_4$ is a group of the formula selected from

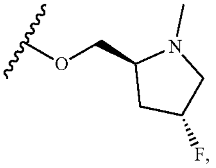
or
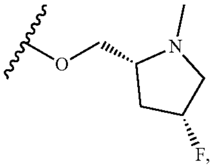

or a pharmaceutically acceptable salt thereof.

41. The compound according to any one of embodiments 1 or 3-33, wherein $R_4$ is a group of the formula

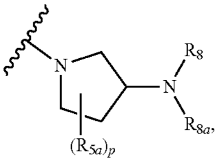

or a pharmaceutically acceptable salt thereof.

42. The compound according to embodiment 41, wherein $R_4$ is a group of the formula

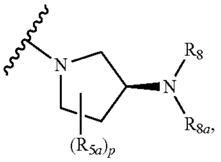

or a pharmaceutically acceptable salt thereof.

43. The compound according to embodiment 41 or 42, wherein $R_4$ is a group of the formula selected from

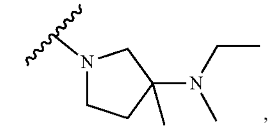
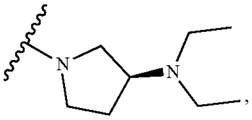
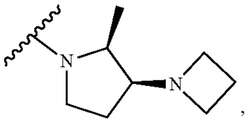
and
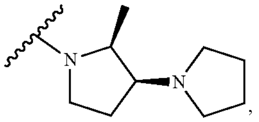

or a pharmaceutically acceptable salt thereof.

44. The compound according to any one of embodiments 1 or 3-33, wherein $R_4$ is a group of the formula selected from

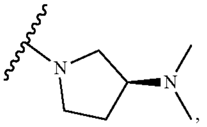
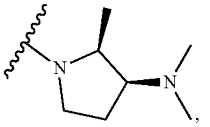
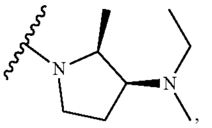
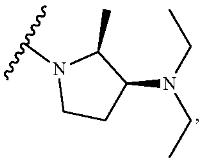
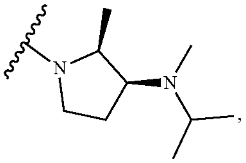
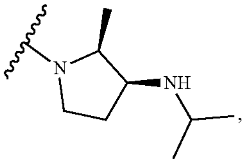
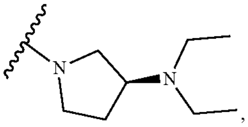
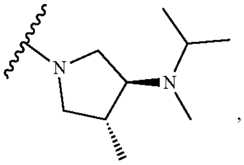
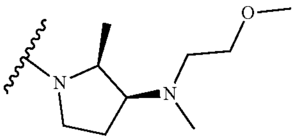
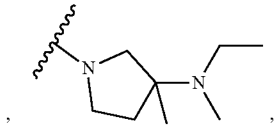
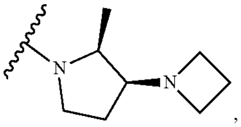
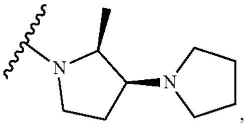
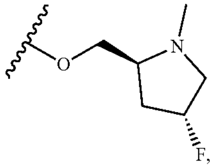
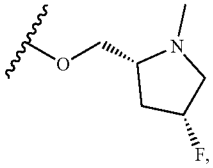
and
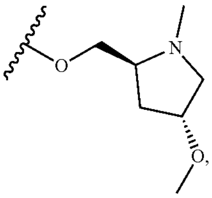

or a pharmaceutically acceptable salt thereof.

45. The compound according to any one of embodiments 1-33, wherein $R_4$ is a group of the formula selected from
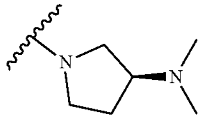,
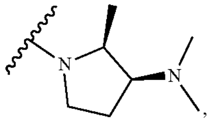,
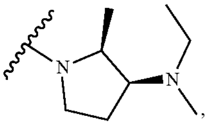,
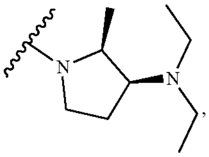,
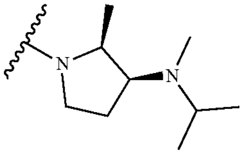,
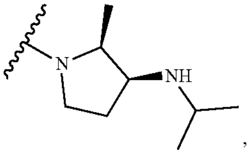,
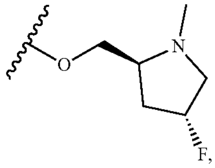, or
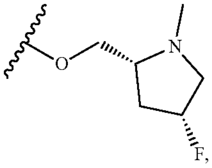,
or a pharmaceutically acceptable salt thereof.
46. The compound according to embodiment 1 or 2, selected from
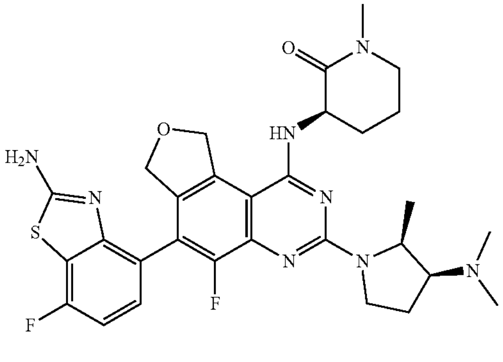,
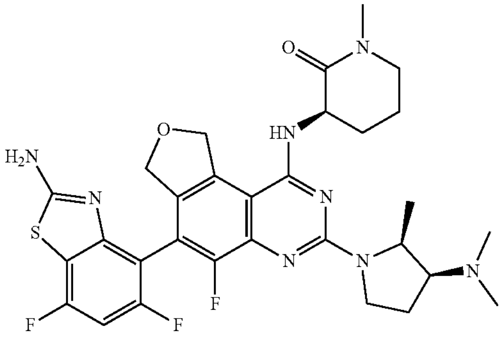,
-continued
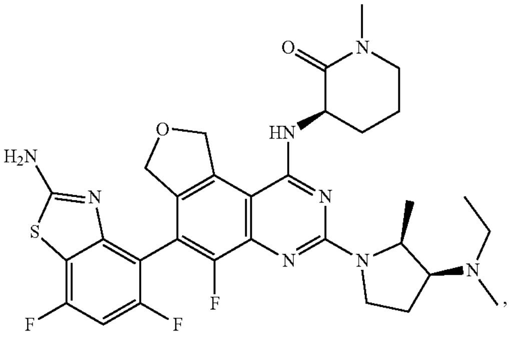,
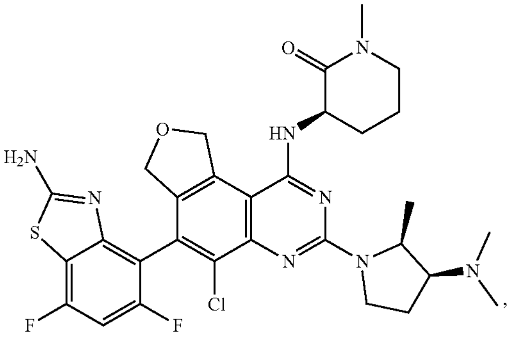,
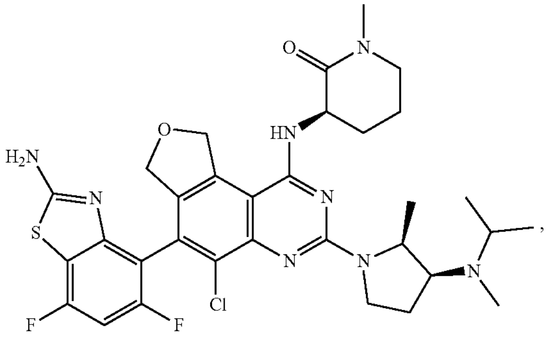,
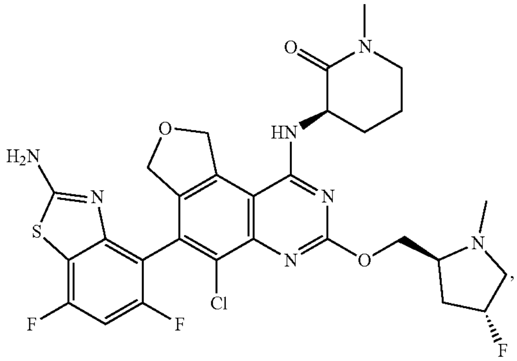,
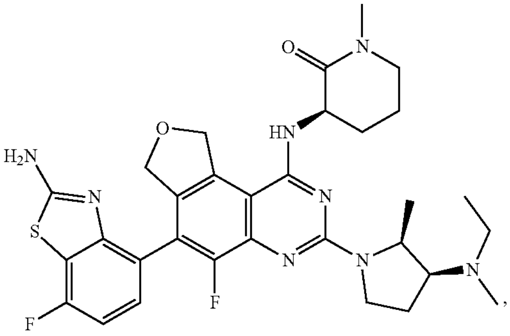, -continued
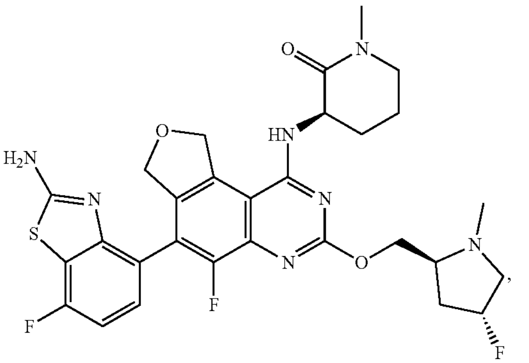
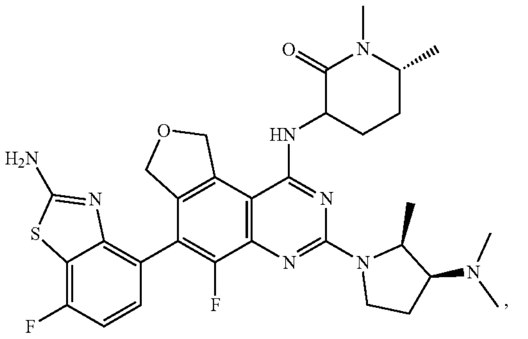
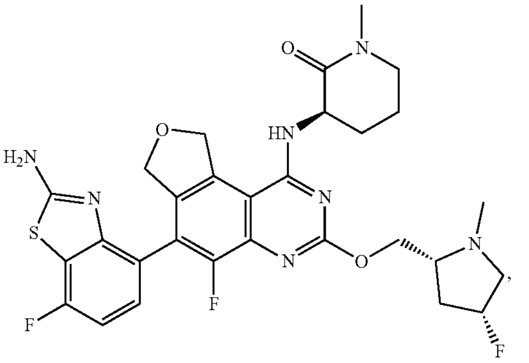
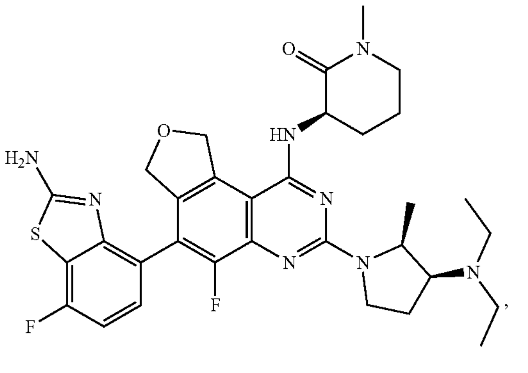
-continued
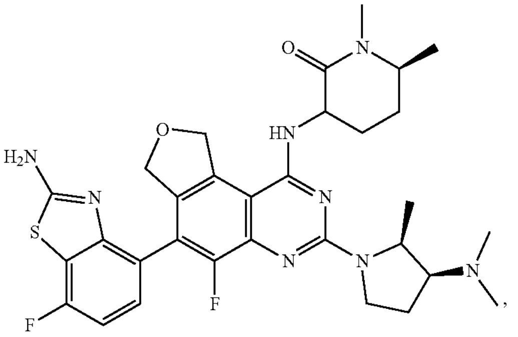
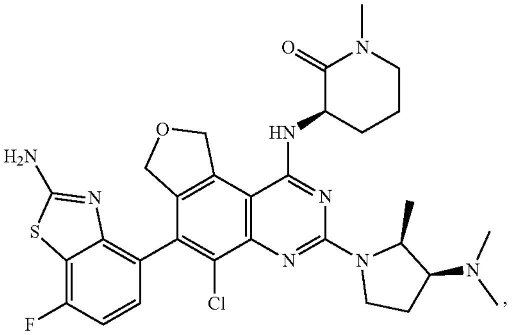
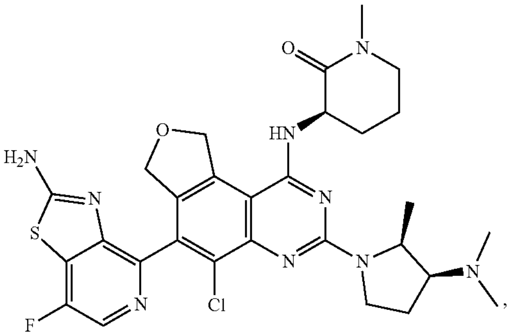
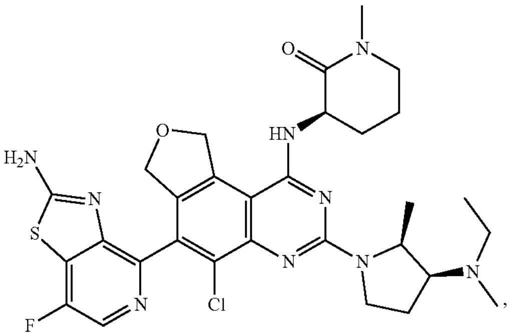
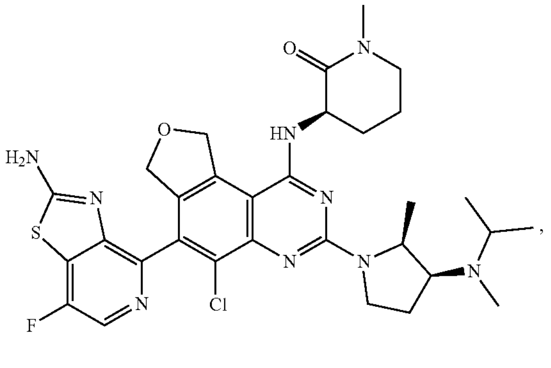

-continued
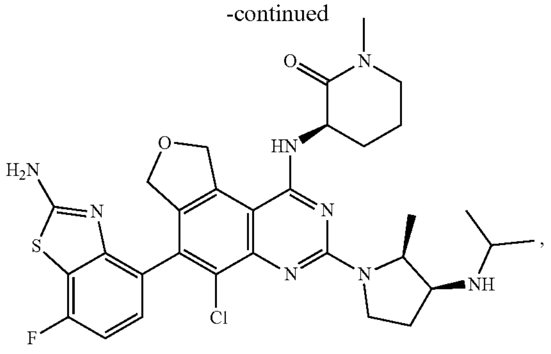
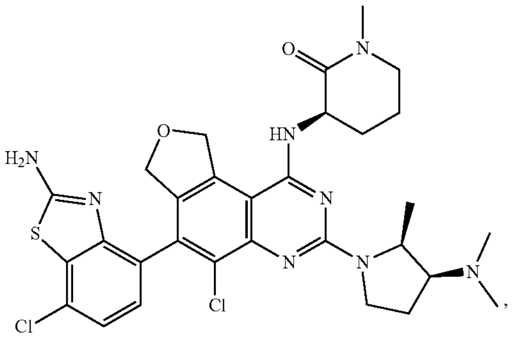
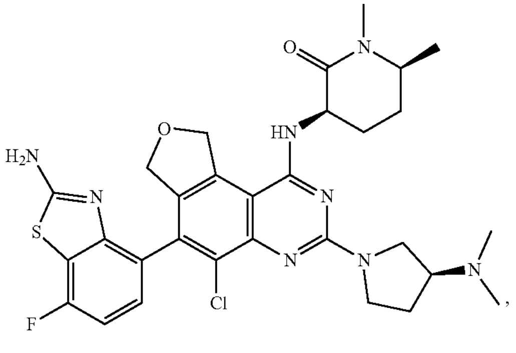
or
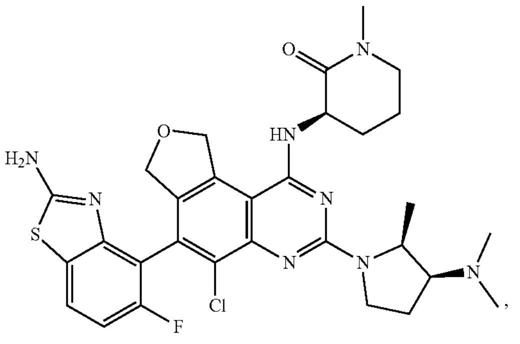
or a pharmaceutically acceptable salt thereof.
47. The compound according to embodiment 1, wherein the compound is selected from
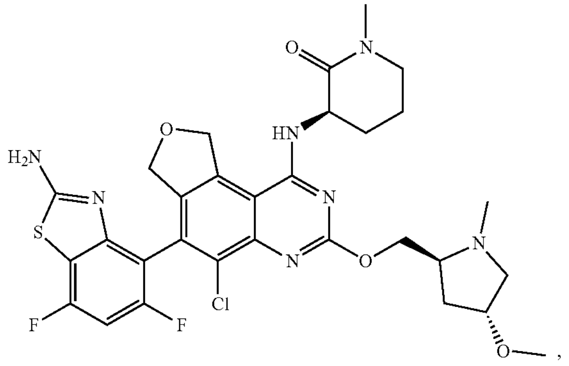
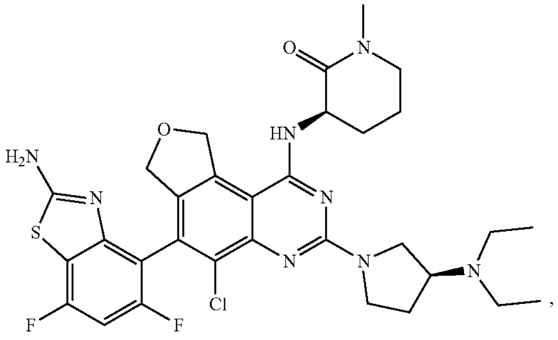
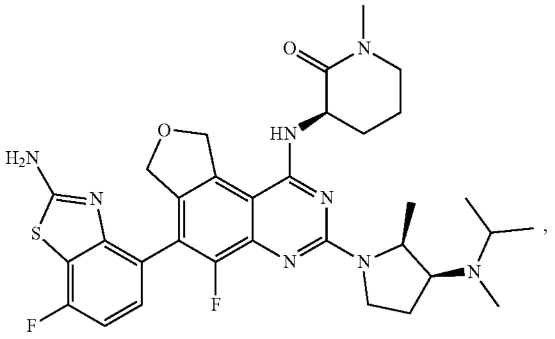
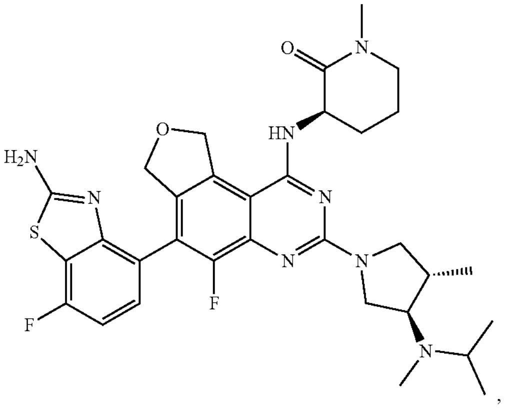

-continued
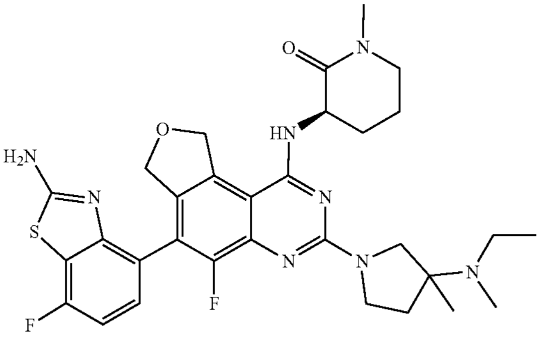
,
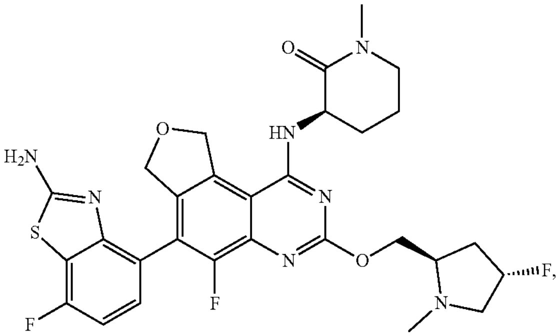
,
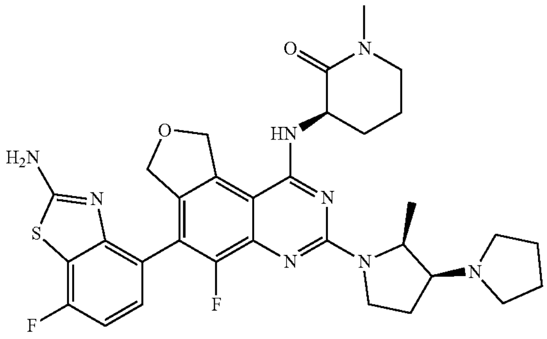
,
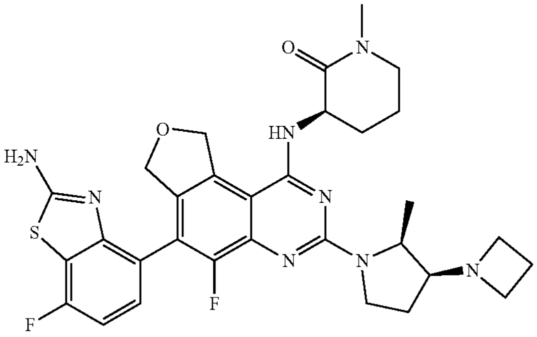
,
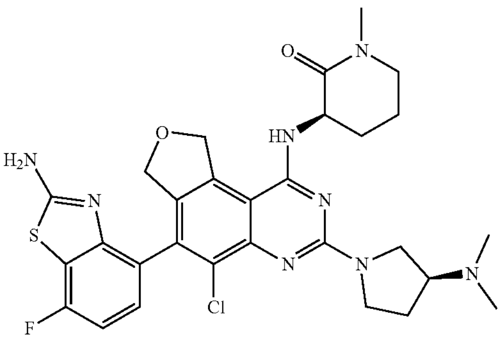
,
-continued
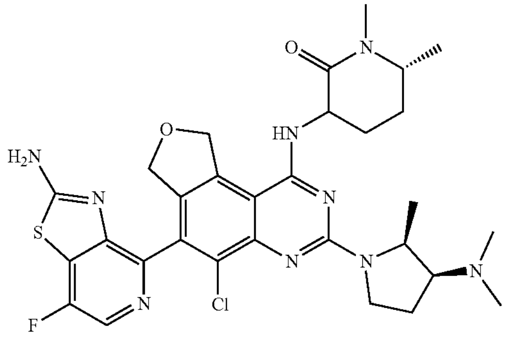
,
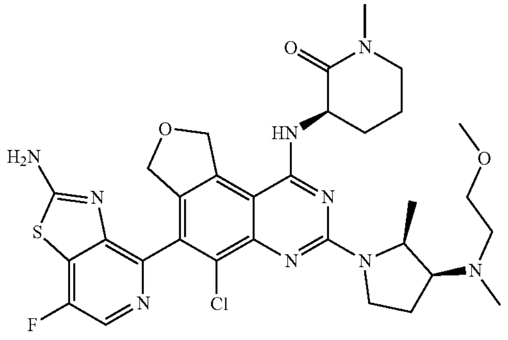
,
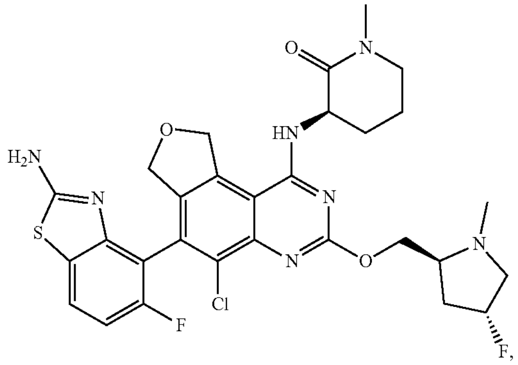
,
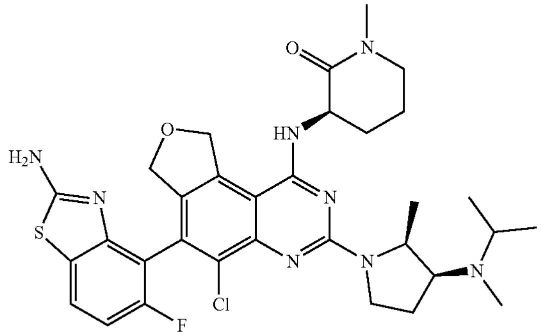
,
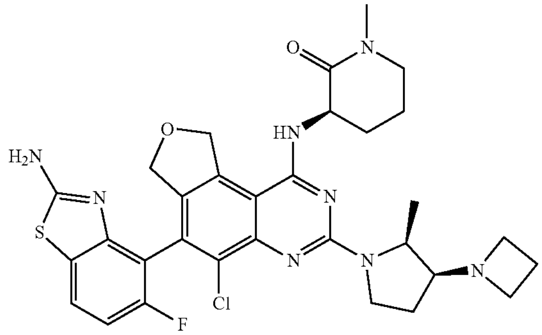
, -continued

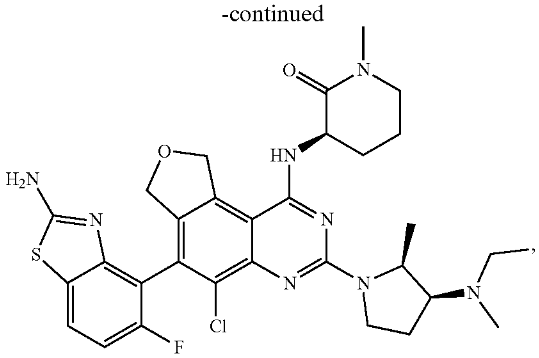

,

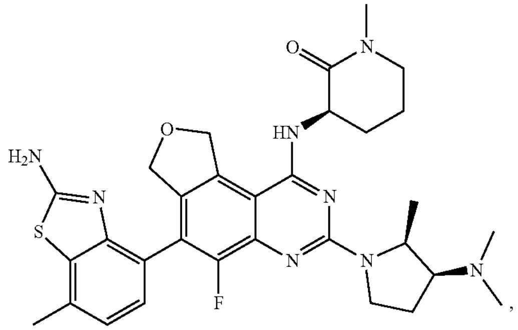

,

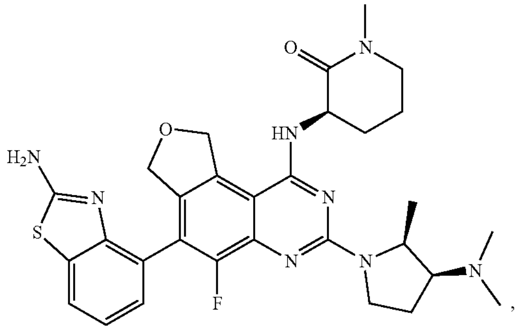

,

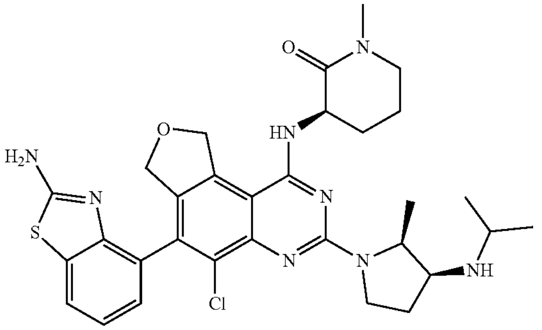

,

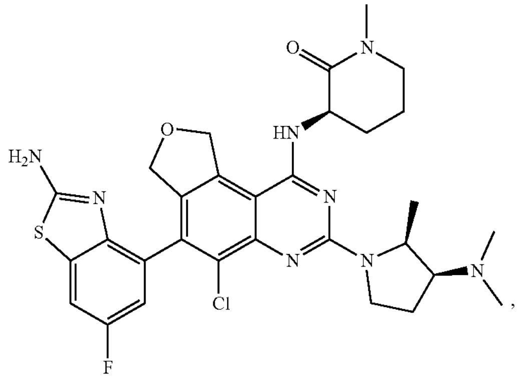

, and

-continued

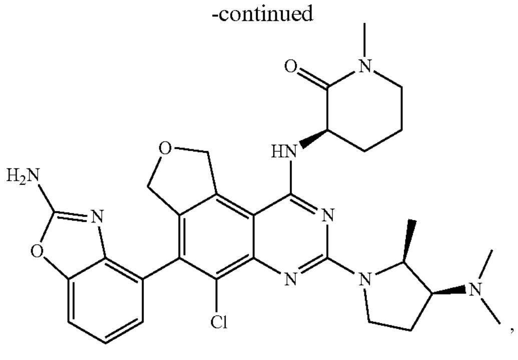

, or a pharmaceutically acceptable salt thereof.

48. A pharmaceutical composition comprising a compound according to any one of embodiments 1-47, or a pharmaceutically acceptable salt thereof, and a pharmaceutically acceptable carrier, diluent or excipient.

49. A method of treating a patient with cancer, comprising administering to a patient in need thereof, an effective amount of a pharmaceutical composition according to embodiment 48, wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

50. A method of treating a patient with cancer, comprising administering to a patient in need thereof, an effective amount of a compound according to any one of embodiments 1-47, or a pharmaceutically acceptable salt thereof, wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

51. The method according to embodiments 49 or 50, wherein the patient has a cancer that was determined to have one or more cells expressing the KRAS G12V mutant protein prior to administration of the compound or a pharmaceutically acceptable salt thereof.

52. The method according to embodiment 49 or 50, wherein one or more cells express KRAS G12V mutant protein.

53. A method of treating a patient with a cancer that has a KRAS G12V mutation comprising administering to a patient in need thereof an effective amount of a compound according to any one of embodiments 1-47, or a pharmaceutically acceptable salt thereof.

54. The method according to embodiment 53, wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

55. The method according to any one of embodiments 49-54, wherein the patient is also administered an effective amount of one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof.

56. The compound, or a pharmaceutically acceptable salt thereof, according to any one of embodiments 1-47, for use in therapy.

57. The compound, or a pharmaceutically acceptable salt thereof, according to any one of embodiments 1-47, for use in the treatment of cancer.

58. The compound, or a pharmaceutically acceptable salt thereof, for use according to embodiment 57, wherein the cancer has a KRAS G12V mutation.

59. The compound, or a pharmaceutically acceptable salt thereof, for use according to embodiment 57 or 58, wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

60. The compound, or a pharmaceutically acceptable salt thereof, according to any one of embodiments 1-47 for use in simultaneous, separate, or sequential combination with one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in the treatment of cancer.

61. The method according to embodiment 55, or compound, or a pharmaceutically acceptable salt thereof, for use according to embodiment 60, wherein the patient is also administered an effective amount of a PD-1 inhibitor.

62. The method according to embodiment 55, or compound, or a pharmaceutically acceptable salt thereof, for use according to embodiment 60, wherein the patient is also administered an effective amount of a PD-L1 inhibitor.

63. The method according to embodiment 55, or compound, or a pharmaceutically acceptable salt thereof, for use according to embodiment 60, wherein the patient is also administered an effective amount of a CDK4/CDK6 inhibitor.

64. The method according to embodiment 55, or compound, or a pharmaceutically acceptable salt thereof, for use according to embodiment 60, wherein the patient is also administered an effective amount of an EGFR inhibitor.

65. The method according to embodiment 55, or compound, or a pharmaceutically acceptable salt thereof, for use according to embodiment 60, wherein the patient is also administered an effective amount of an ERK inhibitor.

66. The method according to embodiment 55, or compound, or a pharmaceutically acceptable salt thereof, for use according to embodiment 60, wherein the patient is also administered an effective amount of an Aurora A inhibitor.

67. The method according to embodiment 55, or compound, or a pharmaceutically acceptable salt thereof, for use according to embodiment 60, wherein the patient is also administered an effective amount of a SHP2 inhibitor.

68. The method according to embodiment 55, or compound, or a pharmaceutically acceptable salt thereof, for use according to embodiment 60, wherein the patient is also administered an effective amount of a platinum agent.

69. The method according to embodiment 55, or compound, or a pharmaceutically acceptable salt thereof, for use according to embodiment 60, wherein the patient is also administered an effective amount of pemetrexed, or pharmaceutically acceptable salts thereof.

70. The method according to any one of embodiments 49-55 or 61-69, or the compound, or a pharmaceutically acceptable salt thereof, for use according to embodiment 57-69, wherein the cancer is non-small cell lung cancer.

71. The method according to any one of embodiments 49-55 or 61-69, or the compound, or a pharmaceutically acceptable salt thereof, for use according to embodiment 57-69, wherein the cancer is colorectal cancer.

72. The method according to any one of embodiments 49-55 or 61-69, or the compound, or a pharmaceutically acceptable salt thereof, for use according to embodiment 57-69, wherein the cancer is pancreatic cancer.

73. The method according to any one of embodiments 49-55 or 61-69, or the compound, or a pharmaceutically acceptable salt thereof, for use according to any one of embodiments 57-69, wherein the cancer is cervical cancer.

74. The method according to any one of embodiments 49-55 or 61-69, or the compound, or a pharmaceutically acceptable salt thereof, for use according to any one of embodiments 57-69, wherein the cancer is esophageal cancer.

75. The method according to any one of embodiments 49-55 or 61-69, or the compound, or a pharmaceutically acceptable salt thereof, for use according to any one of embodiments 57-69, wherein the cancer is endometrial cancer.

76. The method according to any one of embodiments 49-55 or 61-69, or the compound, or a pharmaceutically acceptable salt thereof, for use according to any one of embodiments 57-69, wherein the cancer is ovarian cancer.

77. The method according to any one of embodiments 49-55 or 61-69, or the compound, or a pharmaceutically acceptable salt thereof, for use according to any one of embodiments 57-69, wherein the cancer is cholangiocarcinoma.

78. The method according to any one of embodiments 49-55 or 61-69, or the compound, or a pharmaceutically acceptable salt thereof, for use according to any one of embodiments 57-69, wherein the cancer is stomach adenocarcinoma.

79. The method according to any one of embodiments 49-55 or 61-69, or the compound, or a pharmaceutically acceptable salt thereof, for use according to any one of embodiments 57-69, wherein the cancer is invasive ductal carcinoma.

80. The method according to any one of embodiments 49-55 or 61-69, or the compound, or a pharmaceutically acceptable salt thereof, for use according to any one of embodiments 57-69, wherein the cancer is uterine carcinosarcoma.

81. The method according to any one of embodiments 49-55 or 61-69, or the compound, or a pharmaceutically acceptable salt thereof, for use according to any one of embodiments 57-69, wherein the cancer is a germ cell tumor.

82. The method according to any one of embodiments 49-55 or 61-69, or the compound, or a pharmaceutically acceptable salt thereof, for use according to any one of embodiments 57-69, wherein the cancer is bladder cancer.

83. The method according to any one of embodiments 49-55 or 61-69, or the compound, or a pharmaceutically acceptable salt thereof, for use according to any one of embodiments 57-69, wherein the cancer is small bowel adenocarcinoma.

84. The method according to any one of embodiments 49-55 or 61-69, or the compound, or a pharmaceutically acceptable salt thereof, for use according to any one of embodiments 57-69, wherein the cancer is appendix cancer.

85. The method according to any one of embodiments 49-55 or 61-69, or the compound, or a pharmaceutically acceptable salt thereof, for use according to any one of embodiments 57-69, wherein the cancer is peritoneum cancer.

The chemical drawings in the compounds above contain indications of chiral aspects of the specific compounds shown. However, the chemical drawings in the compounds above do not contain all the possible chiral features of these compounds and the chiral indications shown are not intended to exclude changes to the chiral aspects shown. Thus, alternate chiral versions of the compounds as well as different combinations of chiral attributes are contemplated and included herein.

Further provided herein are methods of treating cancer, comprising administering to a patient in need thereof, an effective amount of a compound according to Formula I, or a pharmaceutically acceptable salt thereof. In this method, the cancer can be lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, or peritoneum cancer. In this method, the cancer can more specifically be non-small cell lung cancer, pancreatic cancer, or colorectal cancer. In an embodiment the cancer can be non-small cell lung cancer. In an embodiment the cancer can be pancreatic cancer. In an embodiment the cancer can be colorectal cancer. In an embodiment the cancer can be stomach adenocarcinoma. In an embodiment the cancer can be invasive ductal carcinoma. In an embodiment the cancer can be uterine carcinosarcoma. In an embodiment the cancer can be germ cell tumors. In an embodiment the cancer can be bladder cancer. In an embodiment the cancer can be small bowel adenocarcinoma. In an embodiment the cancer can be appendix cancer. In an embodiment the cancer can be peritoneum cancer.

Also provided herein is a method of treating cancer, comprising administering to a patient in need thereof, an effective amount of a compound according to Formula I, or a pharmaceutically acceptable salt thereof, in which the cancer has one or more cells that express a mutant KRAS G12V protein. In this method, the cancer can be non-small cell lung cancer, pancreatic cancer, or colorectal cancer, in which the cancer has one or more cells that express a KRAS G12V mutant protein. In an embodiment, the cancer is non-small cell lung carcinoma in which the cancer has one or more cells that express a KRAS G12V mutant protein. In an embodiment, the cancer is mutant pancreatic cancer in which the cancer has one or more cells that express a KRAS G12V mutant protein. In an embodiment, the cancer is colorectal carcinoma in which the cancer has one or more cells that express a KRAS G12V mutant protein. This method also includes treating KRAS G12V mutant bearing cancers of other origins.

Further provided herein is a method of treating a patient with a cancer that has a KRAS G12V mutation comprising administering to a patient in need thereof an effective amount of a compound according to Formula I or a pharmaceutically acceptable salt thereof. In this method, the cancer that has a KRAS G12V mutation can be KRAS G12V mutant lung cancer, KRAS G12V mutant pancreatic cancer, KRAS G12V mutant cervical cancer, KRAS G12V mutant esophageal cancer, KRAS G12V mutant endometrial cancer, KRAS G12V mutant ovarian cancer, KRAS G12V mutant cholangiocarcinoma, KRAS G12V mutant colorectal cancer, KRAS G12V mutant stomach adenocarcinoma, KRAS G12V mutant invasive ductal carcinoma, KRAS G12V mutant uterine carcinosarcoma, KRAS G12V mutant germ cell tumors, KRAS G12V mutant bladder cancer, KRAS G12V mutant small bowel adenocarcinoma, KRAS G12V mutant appendix cancer, and KRAS G12V mutant peritoneum cancer. In an embodiment the cancer that has a KRAS G12V mutation can be KRAS G12V mutant non-small cell lung cancer. In an embodiment the cancer that has a KRAS G12V mutation can be KRAS G12V mutant pancreatic cancer. In an embodiment the cancer that has a KRAS G12V mutation can be KRAS G12V mutant colorectal cancer.

Additionally provided herein is a method of modulating a mutant KRAS G12V enzyme in a patient in need thereof, by administering a compound according to Formula I, or a pharmaceutically acceptable salt thereof. In one embodiment this method comprises inhibiting a human mutant KRAS G12V enzyme.

Also provided herein is a method of treating cancer in a patient in need thereof, wherein the patient has a cancer that was determined to express the KRAS G12V mutant protein. The method comprises administering to a patient an effective amount of a compound according to Formula I, or a pharmaceutically acceptable salt thereof. The G12V mutational status of one or more cancer cells can be determined by a number of assays known in the art. Typically, one or more biopsies containing one or more cancer cells are obtained, and subjected to sequencing and/or polymerase chain reaction (PCR). Circulating cell-free DNA can also be used, e.g. in advanced cancers. Non-limiting examples of sequencing and PCR techniques used to determine the mutational status (e.g., G12C, G12D, and/or G12V mutational status, in one or more cancer cells or in circulating cell-free DNA) include direct sequencing, next-generation sequencing, reverse transcription polymerase chain reaction (RT-PCR), multiplex PCR, and pyrosequencing and multianalyte profiling.

Further provided herein is a compound or a pharmaceutically acceptable salt thereof according to Formula I for use in therapy. The compound or a pharmaceutically acceptable salt thereof, can be for use in treating cancer. For this use in treating cancer, the cancer can be lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, or peritoneum cancer. In an embodiment, the cancer is non-small cell lung cancer. In an embodiment, the cancer is pancreatic cancer. In an embodiment, the cancer is cervical cancer. In an embodiment, the cancer is esophageal cancer. In an embodiment, the cancer is endometrial cancer. In an embodiment, the cancer is ovarian cancer. In an embodiment, the cancer is cholangiocarcinoma. In an embodiment, the cancer is colorectal cancer. In an embodiment, the cancer is stomach adenocarcinoma. In an embodiment, the cancer is invasive ductal carcinoma. In an embodiment, the cancer is uterine carcinosarcoma. In an embodiment, the cancer is germ cell tumors. In an embodiment, the cancer is bladder cancer. In an embodiment, the cancer is small bowel adenocarcinoma. In an embodiment, the cancer is appendix cancer. In an embodiment, the cancer is peritoneum cancer. The cancer can have one or more cancer cells that express the mutant KRAS G12V protein such as KRAS G12V mutant lung cancer, KRAS G12V mutant pancreatic cancer, KRAS G12V mutant cervical cancer, KRAS G12V mutant esophageal cancer, KRAS G12V mutant endometrial cancer, KRAS G12V mutant ovarian cancer, KRAS G12V mutant cholangiocarcinoma, KRAS G12V mutant colorectal cancer, KRAS G12V mutant stomach adenocarcinoma, KRAS G12V mutant invasive ductal carcinoma, KRAS G12V mutant uterine carcinosarcoma, KRAS G12V mutant germ cell tumors, KRAS G12V mutant bladder cancer, KRAS G12V mutant small bowel adenocarcinoma, KRAS G12V mutant appendix cancer, or KRAS G12V mutant peritoneum cancer. Additionally, the cancer can be non-small cell lung cancer, and one or more cells express KRAS G12V mutant protein. Further, the cancer can be colorectal cancer, and one or more cells express KRAS G12V mutant protein. Additionally, the cancer can be pancreatic cancer, and one or more cells express KRAS G12V mutant protein. Further, the cancer can be KRAS G12V mutant cervical cancer, and one or more cells express KRAS G12V mutant protein. Additionally, the cancer can be KRAS G12V mutant esophageal cancer, and one or more cells express KRAS G12V mutant protein. Further, the cancer can be KRAS G12V mutant endometrial cancer, and one or more cells express KRAS G12V mutant protein. Additionally, the cancer can be KRAS G12V mutant ovarian cancer, and one or more cells express KRAS G12V mutant protein. Further, the cancer can be KRAS G12V mutant cholangiocarcinoma, and one or more cells express KRAS G12V mutant protein. Additionally, the cancer can be KRAS G12V mutant stomach adenocarcinoma, and one or more cells express KRAS G12V mutant protein. Further, the cancer can be KRAS G12V mutant invasive ductal carcinoma, and one or more cells express KRAS G12V mutant protein. Additionally, the cancer can be KRAS G12V mutant uterine carcinosarcoma, and one or more cells express KRAS G12V mutant protein. Further, the cancer can be KRAS G12V mutant germ cell tumors, and one or more cells express KRAS G12V mutant protein. Additionally, the cancer can be KRAS G12V mutant bladder cancer, and one or more cells express KRAS G12V mutant protein. Further, the cancer can be KRAS G12V mutant small bowel adenocarcinoma, and one or more cells express KRAS G12V mutant protein. Additionally, the cancer can be KRAS G12V mutant appendix cancer, and one or more cells express KRAS G12V mutant protein. Further, the cancer can be KRAS G12V mutant peritoneum cancer, and one or more cells express KRAS G12V mutant protein. The patient can have a cancer that was determined to have one or more cells expressing the KRAS G12V mutant protein prior to administration of the compound or a pharmaceutically acceptable salt thereof. The patient may have been treated with a different course of treatment prior to being treated as described herein.

The compounds provided herein according to Formula I, or a pharmaceutically acceptable salt thereof, may also be used in the manufacture of a medicament for treating cancer. When used in the manufacture of a medicament, the cancer can be lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer. In an embodiment, the cancer is non-small cell lung cancer. In an embodiment, the cancer is pancreatic cancer. In an embodiment, the cancer is cervical cancer. In an embodiment, the cancer is esophageal cancer. In an embodiment, the cancer is endometrial cancer. In an embodiment, the cancer is ovarian cancer. In an embodiment, the cancer is cholangiocarcinoma. In an embodiment, the cancer is colorectal cancer. In an embodiment, the cancer is stomach adenocarcinoma. In an embodiment, the cancer is invasive ductal carcinoma. In an embodiment, the cancer is uterine carcinosarcoma. In an embodiment, the cancer is germ cell tumors. In an embodiment, the cancer is bladder cancer. In an embodiment, the cancer is small bowel adenocarcinoma. In an embodiment, the cancer is appendix cancer. In an embodiment, the cancer is peritoneum cancer. The cancer can have one or more cancer cells that express the mutant KRAS G12V protein. When the cancer cells express KRAS G12V protein, the cancer can be selected from KRAS G12V mutant lung cancer, KRAS G12V mutant pancreatic cancer, KRAS G12V mutant cervical cancer, KRAS G12V mutant esophageal cancer, KRAS G12V mutant endometrial cancer, KRAS G12V mutant ovarian cancer, KRAS G12V mutant cholangiocarcinoma, KRAS G12V mutant colorectal cancer, KRAS G12V mutant stomach adenocarcinoma, KRAS G12V mutant invasive ductal carcinoma, KRAS G12V mutant uterine carcinosarcoma, KRAS G12V mutant germ cell tumors, KRAS G12V mutant bladder cancer, KRAS G12V mutant small bowel adenocarcinoma, KRAS G12V mutant appendix cancer, and KRAS G12V mutant peritoneum cancer.

Also provided herein is a method of treating cancer, comprising administering to a patient in need thereof, an effective amount of a compound according to Formula I, or a pharmaceutically acceptable salt thereof, and one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in which the cancer has one or more cells that express a mutant KRAS G12V protein. Further provided herein is a compound according to Formula I, or a pharmaceutically acceptable salt thereof, for use in simultaneous, separate, or sequential combination with one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in the treatment of cancer. Additionally provided is a combination comprising a compound according to Formula I, or a pharmaceutically acceptable salt thereof, and one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, for simultaneous, separate, or sequential use in the treatment of cancer.

Also provided is a method of treating cancer, comprising administering to a patient in need thereof, an effective amount of a compound according to Formula I, or a pharmaceutically acceptable salt thereof, and a PD-1 or PD-L1 inhibitor, in which the cancer has one or more cells that express a mutant KRAS G12V protein. Further provided is a compound according to Formula I, or a pharmaceutically acceptable salt thereof, for use in simultaneous, separate, or sequential combination with a PD-1 or PD-L1 inhibitor, for use in the treatment of cancer. Additionally provided is a combination comprising a compound according to Formula I, or a pharmaceutically acceptable salt thereof, and a PD-1 or PD-L1 inhibitor, for simultaneous, separate, or sequential use in the treatment of cancer. As used herein, the PD-1 or PD-L1 inhibitor can be pembrolizumab; the PD-1 or PD-L1 inhibitor can be nivolumab; the PD-1 or PD-L1 inhibitor can be cemiplimab; the PD-1 or PD-L1 inhibitor can be sintilimab; the PD-1 or PD-L1 inhibitor can be atezolizumab; the PD-1 or PD-L1 inhibitor can be avelumab; the PD-1 or PD-L1 inhibitor can be durvalumab; or the PD-1 or PD-L1 inhibitor can be lodapilimab.

Also provided is a method of treating cancer, comprising administering to a patient in need thereof, an effective amount of a compound according to Formula I, or a pharmaceutically acceptable salt thereof, and a CDK4/CDK6 inhibitor, or a pharmaceutically acceptable salt thereof, in which the cancer has one or more cells that express a mutant KRAS G12V protein. Further provided is a compound according to Formula I, or a pharmaceutically acceptable salt thereof, for use in simultaneous, separate, or sequential combination with a CDK4/CDK6 inhibitor, or a pharmaceutically acceptable salt thereof, for use in the treatment of cancer, in which the cancer has one or more cells that express a mutant KRAS G12V protein. Additionally provided is a combination comprising a compound according to Formula I, or a pharmaceutically acceptable salt thereof, and a CDK4/CDK6 inhibitor, or a pharmaceutically acceptable salt thereof, for simultaneous, separate, or sequential use in the treatment of cancer, in which the cancer has one or more cells that express a mutant KRAS G12V protein. As used herein, the CDK4/CDK6 inhibitor can be abemaciclib; the CDK4/CDK6 inhibitor can be palbociclib; or the CDK4/CDK6 inhibitor can be ribociclib.

Also provided is a method of treating cancer, comprising administering to a patient in need thereof, an effective amount of a compound according to Formula I, or a pharmaceutically acceptable salt thereof, and an EGFR inhibitor, or a pharmaceutically acceptable salt thereof, in which the cancer has one or more cells that express a mutant KRAS G12V protein. Further provided is a compound according to Formula I, or a pharmaceutically acceptable salt thereof, for use in simultaneous, separate, or sequential combination with an EGFR inhibitor, or a pharmaceutically acceptable salt thereof, for the treatment of cancer. Additional provided is a combination comprising a compound according to Formula I, or a pharmaceutically acceptable salt thereof, and an EGFR inhibitor, or a pharmaceutically acceptable salt thereof, for simultaneous, separate, or sequential use in the treatment of cancer. As used herein, the EGFR inhibitor can be erlotinib; the EGFR inhibitor can be afatinib; the EGFR inhibitor can be gefitinib; the EGFR inhibitor can be cetuximab.

Also provided is a method of treating cancer, comprising administering to a patient in need thereof, an effective amount of a compound according to Formula I, or a pharmaceutically acceptable salt thereof, and an ERK inhibitor, or a pharmaceutically acceptable salt thereof, in which the cancer has one or more cells that express a mutant KRAS G12V protein. Also provided is a method of treating cancer, comprising administering to a patient in need thereof, an effective amount of a compound according to Formula I, or a pharmaceutically acceptable salt thereof, and an Aurora A inhibitor, in which the cancer has one or more cells that express a mutant KRAS G12V protein. Further provided is a compound according to Formula I, or a pharmaceutically acceptable salt thereof, for use in simultaneous, separate, or sequential combination with an Aurora A inhibitor, or a pharmaceutically acceptable salt thereof, for the treatment of cancer, in which the cancer has one or more cells that express a mutant KRAS G12V protein. Further provided is a compound according to Formula I, or a pharmaceutically acceptable salt thereof, for use in simultaneous, separate, or sequential combination with an ERK inhibitor, or a pharmaceutically acceptable salt thereof, for the treatment of cancer, in which the cancer has one or more cells that express a mutant KRAS G12V protein. Additionally provided is a combination comprising a compound according to Formula I, or a pharmaceutically acceptable salt thereof, and an ERK inhibitor, or a pharmaceutically acceptable salt thereof, for simultaneous, separate, or sequential use in the treatment of cancer. As used herein, the ERK inhibitor can be LY3214996; the ERK inhibitor can be LTT462; or the ERK inhibitor can be KO-947.

Also provided is a method of treating cancer, comprising administering to a patient in need thereof, an effective amount of a compound according to Formula I, or a pharmaceutically acceptable salt thereof, and an Aurora A inhibitor, in which the cancer has one or more cells that express a mutant KRAS G12V protein. Further provided is a compound according to Formula I, or a pharmaceutically acceptable salt thereof, for use in simultaneous, separate, or sequential combination with an Aurora A inhibitor, or a pharmaceutically acceptable salt thereof, for the treatment of cancer, in which the cancer has one or more cells that express a mutant KRAS G12V protein. Additionally provided is a combination comprising a compound according to Formula I, or a pharmaceutically acceptable salt thereof, and an Aurora A inhibitor, for simultaneous, separate, or sequential use in the treatment of cancer. As used herein, the Aurora A inhibitor can be alisertib, tozasertib, (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:2-methylpropan-2-amine (1:1) salt, and (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:amine (1:1) salt, or a pharmaceutically acceptable salt thereof. In one embodiment, the Aurora A inhibitor is (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid.

Also provided is a method of treating cancer, comprising administering to a patient in need thereof, an effective amount of a compound according to Formula I, or a pharmaceutically acceptable salt thereof, and a SHP2 inhibitor, in which the cancer has one or more cells that express a mutant KRAS G12V protein. Further provided is a compound according to Formula I, or a pharmaceutically acceptable salt thereof, for use in simultaneous, separate, or sequential combination with a SHP2 inhibitor, or a pharmaceutically acceptable salt thereof, for the treatment of cancer, in which the cancer has one or more cells that express a mutant KRAS G12V protein. Additionally provided is a combination comprising a compound according to Formula I, or a pharmaceutically acceptable salt thereof, and a SHP2 inhibitor, for simultaneous, separate, or sequential use in the treatment of cancer. As used herein, the SHP2 inhibitor, or a pharmaceutically acceptable salt thereof, can be a Type I SHP2 Inhibitor or a Type II SHP2 Inhibitor. Examples of Type I SHP2 inhibitors include, but are not limited to, PHPS1, GS-493, NSC-87877, NSC-117199, and Cefsulodin, and pharmaceutically acceptable salts thereof. Examples of Type II SHP2 inhibitors include, but are not limited to, JAB-3068, JAB-3312, RMC-4550, RMC-4630, SHP099, SHP244, SHP389, SHP394, TNO155, RG-6433, and RLY-1971, and pharmaceutically acceptable salts thereof. Additional examples of SHP2 inhibitors include, but are not limited to, BBP-398, IACS-15509, IACS-13909, X37, ERAS-601, SH3809, HBI-2376, ETS-001, and PCC0208023, and pharmaceutically acceptable salts thereof. This method also includes treating KRAS G12V mutant protein mutant bearing cancers of other origins.

Also provided is a method of treating cancer, comprising administering to a patient in need thereof, an effective amount of a compound according to Formula I, or a pharmaceutically acceptable salt thereof, and a platinum agent, in which the cancer has one or more cells that express a mutant KRAS G12V protein. Further provided is a compound according to Formula I, or a pharmaceutically acceptable salt thereof, for use in simultaneous, separate, or sequential combination with a platinum agent, or a pharmaceutically acceptable salt thereof, for the treatment of cancer, in which the cancer has one or more cells that express a mutant KRAS G12V protein. Additionally provided is a combination comprising a compound according to Formula I, or a pharmaceutically acceptable salt thereof, and a platinum agent, for simultaneous, separate, or sequential use in the treatment of cancer. As used herein, the platinum agent can be cisplatin; the platinum agent can be carboplatin; or the platinum agent can be oxaliplatin.

Also provided is a method of treating cancer, comprising administering to a patient in need thereof, an effective amount of a compound according to Formula I, or a pharmaceutically acceptable salt thereof, and pemetrexed, in which the cancer has one or more cells that express a mutant KRAS G12V protein. Further provided is a compound according to Formula I, or a pharmaceutically acceptable salt thereof, for use in simultaneous, separate, or sequential combination with pemetrexed, for the treatment of cancer, in which the cancer has one or more cells that express a mutant KRAS G12V protein. Additionally provided is a combination comprising a compound according to Formula I, or a pharmaceutically acceptable salt thereof, and pemetrexed, for simultaneous, separate, or sequential use in the treatment of cancer, in which the cancer has one or more cells that express a mutant KRAS G12V protein.

As described above, the cancer can be lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, or peritoneum cancer, in which the cancer has one or more cells that express a KRAS G12V mutant protein, or the cancer can be mutant lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, or peritoneum cancer, in which the cancer has one or more cells that express a KRAS G12V mutant protein. These methods also includes treating KRAS G12V mutant bearing cancers of other origins.

The term "pharmaceutically acceptable salt" as used herein refers to a salt of a compound considered to be acceptable for clinical and/or veterinary use. Examples of pharmaceutically acceptable salts and common methodology for preparing them can be found in "Handbook of Pharmaceutical Salts: Properties, Selection and Use" P. Stahl, et al., 2nd Revised Edition, Wiley-VCH, 2011 and S. M. Berge, et al., "Pharmaceutical Salts", *Journal of Pharmaceutical Sciences,* 1977, 66(1), 1-19.

Pharmaceutical compositions containing the compounds of Formula I as described herein may be prepared using pharmaceutically acceptable additives. The term "pharmaceutically acceptable additive(s)" as used herein for the pharmaceutical compositions, refers to one or more carriers, diluents, and excipients that are compatible with the other additives of the composition or formulation and not deleterious to the patient. Examples of pharmaceutical compositions and processes for their preparation can be found in "Remington: The Science and Practice of Pharmacy", Loyd, V., et al. Eds., $22^{nd}$ Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose, alginates, gelatin, and polyvinyl-pyrrolidone; kaolin and bentonite; and polyethyl glycols.

As used herein, the term "effective amount" refers to an amount that is a dosage, which is effective in achieve a desired therapeutic result such as treating a disorder or disease, like a cancerous lesion or progression of abnormal cell growth and/or cell division. Factors considered in the determination of an effective amount or dose of a compound include: whether the compound or its salt will be administered; the co-administration of other agents, if used; the species of patient to be treated; the patient's size, age, gender, and general health; the degree of involvement or stage and/or the severity of the disorder; the response of the individual patient; the mode of administration; the bioavailability characteristics of the preparation administered; the dose regimen selected; and the use of other concomitant medication.

A treating physician, veterinarian, or other medical person will be able to determine an effective amount of the compound for treatment of a patient in need. Pharmaceutical compositions can be formulated as a tablet or capsule for oral administration, a solution for oral administration, or an injectable solution. The tablet, capsule, or solution can include a compound of the present invention in an amount effective for treating a patient in need of treatment with cancer.

As used herein, the terms "treating", "to treat", or "treatment", includes slowing, controlling, delaying, reducing, stopping, reversing, preventing, or ameliorating the progression or severity of an existing symptom, disorder, condition, which can include specifically slowing the growth of a cancerous lesion or progression of abnormal cell growth and/or cell division. Treating does not necessarily indicate a total elimination of all disorder or disease symptoms.

As used herein, the term "patient" refers to a mammal in need of treatment. Specifically, the patient can be a human that is in need of treatment with cancer, for example, KRAS G12V mutant protein mutant bearing cancers.

Certain abbreviations are defined as follows: "ACN" refers to acetonitrile; "AcOH" or "HOAc" refer to acetic acid; "aq." refers to aqueous; "conc." refers to concentrated; "DCM" refers to dichloromethane; "DIBAL-H" refers to diisobutylaluminum hydride; "DIEA" and "DIPEA" refer to N,N-diisopropyl ethylamine; "DMAP" refers to 4-dimethylaminopyridine; "DMEA" refers to N,N-dimethylethylamine; "DMF" refers to N,N-dimethylformamide; "DMSO" refers to dimethylsulfoxide; "ELISA" refers to enzyme-linked immunosorbent assay; "ERK" refers to extracellular signal-regulated kinases; "Et" refers to an ethyl group; "EtOAc" refers to ethyl acetate; "$Et_2O$" refers to diethyl ether; "EtOH" refers to ethanol; "FA" refers to formic acid; "FBS" refers to fetal bovine serum; "GDP" refers to guanosine diphosphate; "GTP" refers to guanosine triphosphate; "h" refers to hour or hours; "Hex" or "hex" refers to hexane or hexanes; "HPLC" refers to high-performance liquid chromatography; "IPA" refers to isopropyl alcohol; "IPAm" refers to isopropyl amine; "KOAc" refers to potassium acetate; "LC-ES/MS" refers to liquid chromatograph-electrospray mass spectrometry; "LC-MS" refers to liquid chromatography mass spectrometry; "LiHMDS" refers to lithium bis(trimethylsilyl)amide; "MAPK" refers to mitogen-activated protein kinases; "mCPBA" refers to 3-chloroperoxybenzoic acid; "Me" refers to a methyl group; "MeOH" refers to methanol; "min" refers to minute or minutes; "MTBE" refers to methyl tert-butyl ether; "NMP" refers to 1-methylpyrrolidin-2-one; "$Pd(OAc)_2$ refers to palladium (II) acetate; "RT" refers to room temperature; "sat." refers to saturated; "SCX" refers to strong cation exchange; "TBAF" refers to tetrabutylammonium fluoride; "tBu" refers to the tert-butyl group; "t-BuOH" refers to tert-butanol or tert-butyl alcohol; "TEA" refers to triethylamine; "TFA" refers to trifluoracetic acid; "THF" refers to tetrahydrofuran; "XantPhos" refers to 4,5-bis(diphenylphosphino)-9,9-dimethylxanthene; "XPhos" refers to 2-(dicyclohexylphosphino)-2',4',6'-tri-isopropyl-1,1'-biphenyl.

Individual isomers, enantiomers, diastereomers, and atropisomers may be separated or resolved at any convenient point in the synthesis of compounds listed below, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994). The molecules described herein include compounds that are atropisomers and which can exist in different conformations or as different rotomers. Atropisomers are compounds that exist in different conformations arising from restricted rotation about a single bond. Atropisomers can be isolated as separate chemical species if the energy barrier to rotation about the single bond is sufficiently high that the rate of interconversion is slow enough to allow the individual rotomers to be separated from each other. This description is intended to include all of the isomers, enantiomers, diastereomers, and atropisomers possible for the compounds disclosed herein or that could be made using the compounds disclosed herein. In the molecules described herein, only molecules in which the absolute conformation of a chiral center (or atropisomer conformation) is known have used naming conventions or chemical formula that are drawn to indicate the chirality or atropisomerism. Those of skill in the art will readily understand when other chiral centers are present in the molecules described herein and be able to identify the same.

Compounds of any one of Formula I that are chemically capable of forming salts are readily converted to and may be isolated as a pharmaceutically acceptable salt. Salt formation can occur upon the addition of a pharmaceutically acceptable acid to form the acid addition salt. Salts can also form simultaneously upon deprotection of a nitrogen or oxygen, i.e., removing the protecting group. Examples, reactions and conditions for salt formation can be found in Gould, P. L., "Salt selection for basic drugs," *International Journal of Pharmaceutics,* 33: 201-217 (1986); Bastin, R. J., et al. "Salt Selection and Optimization Procedures for Pharmaceutical New Chemical Entities," *Organic Process Research and Development,* 4: 427-435 (2000); and Berge, S. M., et al., "Pharmaceutical Salts," *Journal of Pharmaceutical Sciences,* 66: 1-19, (1977).

The compounds of the present invention, or salts thereof, may be prepared by a variety of procedures, some of which are illustrated in the Schemes, Preparations, and Examples below. The specific synthetic steps for each of the routes described may be combined in different ways, or in conjunction with steps from different routes, to prepare compounds or salts of the present invention. The products of each step in the Preparations below can be recovered by conventional methods, including extraction, evaporation, precipitation, chromatography, filtration, trituration, and crystallization.

EXAMPLES

Preparation 1 tert-Butyl (4-bromo-5-fluorobenzo[d]thiazol-2-yl) carbamate

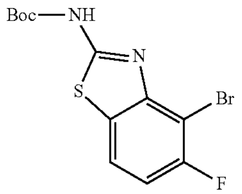 [SMILES: CC(C)(C)OC(=O)Nc1nc2c(Br)c(F)ccc2s1]

To a mixture of 4-bromo-5-fluorobenzo[d]thiazol-2-amine (10.6 g, 42.9 mmol) and di-tert-butyl dicarbonate (10.3 g, 47.2 mmol) in DCM (100 mL) was added 4-dimethylaminopyridine (0.262 g, 2.14 mmol). The mixture was stirred at room temperature overnight, then combined with diatomaceous earth. The crude material was purified on silica, eluting with 0-100% EtOAc in DCM to obtain the title compound (13.4 g, 90%) as an off-white solid. MS (ES) m/z=347 (M−1).

The following compounds in Table 1 were prepared in similar manner as described in Preparation 1. A base, such as triethylamine or diisopropylethylamine, may have been used. Various methods were used to purify the compounds, which would be apparent to one skilled in the art.

TABLE 1

| Preparation | Chemical Name | Structure | MS (ES) m/z (M + 1) |
|---|---|---|---|
| 2 | tert-Butyl (4-chloro-7-fluorothiazolo[4,5-c]pyridin-2-yl)carbamate | 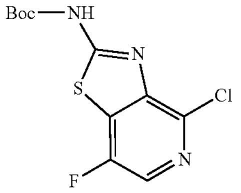 [SMILES: CC(C)(C)OC(=O)Nc1nc2c(Cl)ncc(F)c2s1] | 304 |
| 3 | tert-Butyl (7-chloro-4-iodobenzo[d]thiazol-2-yl)carbamate | 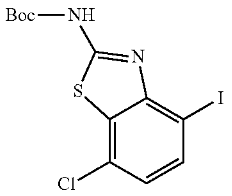 [SMILES: CC(C)(C)OC(=O)Nc1nc2c(I)ccc(Cl)c2s1] | 409 (M − 1) |

Preparation 4

(2-((tert-Butoxycarbonyl)amino)-5-fluorobenzo[d]thiazol-4-yl)boronic acid

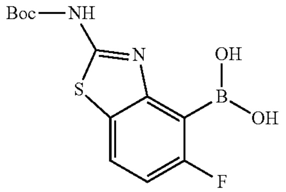 [SMILES: CC(C)(C)OC(=O)Nc1nc2c(B(O)O)c(F)ccc2s1]

Sodium hydride (60 wt % in mineral oil; 1.73 g, 43.2 mmol) was mixed with THF (100 mL) under argon and cooled to 0° C. A mixture of tert-butyl (4-bromo-5-fluorobenzo[d]thiazol-2-yl)carbamate (10.0 g, 28.8 mmol) in THF (35 mL) was added. The mixture was stirred at 0° C. for 30 min, cooled to −78° C., and n-butyllithium (2.5M in hexanes; 17.3 mL, 43.2 mmol) was slowly added. The mixture was stirred at −78° C. for 15 min, then triisopropyl borate (19.9 mL, 86.4 mmol) was slowly added. The mixture was stirred at −78° C. for 1 h, −40° C. for 1 h, −10° C. for 45 min, then slowly quenched with saturated aqueous ammonium chloride. The mixture was diluted with water (100 mL) and extracted with EtOAc (300 mL, 200 mL). The combined organics were dried over anhydrous $Na_2SO_4$, filtered, and concentrated under reduced pressure. The residue was diluted with hexanes, stirred at 50° C. for 30 min, cooled to room temperature, and filtered. The solids were washed with hexanes and dried under vacuum to obtain the title compound (7.2 g, 80%) as a white solid. MS (ES) m/z=313 (M+1).

Preparation 5

5-Fluoroisobenzofuran-1 (3H)-one

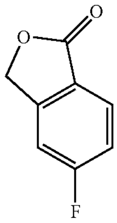 [SMILES: O=C1OCc2cc(F)ccc21]

To a stirred mixture of (2-bromo-5-fluorophenyl)methanol (500 g, 2.44 mol) and TEA (474.6 mL, 3.41 mol, 1.4 eq.) in ACN (2500 mL) was added $Pd(OAc)_2$ (10.95 g, 48.77 mmol, 0.02 eq.) and XantPhos (42.33 g, 73.16 mmol, 0.03 equiv.) at RT, then stirred for 3 days at 120° C. under 10 atm of carbon monoxide. The reaction was cooled to RT and concentrated. The residue was diluted with $H_2O$ (1,000 mL), then extracted with EtOAc (2×2000 mL). The combined organic layers were washed with brine (2×1,000 mL), dried over anhydrous $Na_2SO_4$, filtered and concentrated. The residue was triturated with 10:1 hexanes/EtOAc (1,100 mL) and then filtered. The filter cake was dried at 50° C. for ~18 h to obtain the title compound as a yellow solid (300 g, 81%). MS (ES) m/z=153 (M+1).

Preparation 6

4-Bromo-5-fluoro-6-nitroisobenzofuran-1 (3H)-one

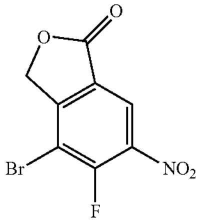 [SMILES: O=C1OCc2c1cc([N+](=O)[O-])c(F)c2Br]

To a stirred mixture of 5-fluoroisobenzofuran-1 (3H)-one (300 g, 1.97 mol) in $H_2SO_4$ (1,500 mL) was added $HNO_3$ (273.38 g, 4.348 mol, 2.2 eq.) dropwise at 65° C. The reaction was stirred for 1 h then cooled to RT. 1,3-dibromo-5,5-dimethylimidazolidine-2,4-dione (2,255.43 g, 7.88 mol, 4 eq.) was added in portions over 20 min and was stirred at RT for ~18 h. The mixture was poured onto ice/water (pre-treated with 3 kg $Na_2SO_3$) and filtered. The filter cake was dissolved in EtOAc (3,000 mL), washed with sat. aq. $Na_2CO_3$ (2×1,000 mL), brine (2×1,000 mL), dried over anhydrous $Na_2SO_4$ and concentrated. The residue was triturated with 10:1 hexanes/EtOAc (660 mL) and was filtered and dried at 50° C. for ~18 h to obtain the title compound as a yellow solid (270 g, 49%) which was used in a subsequent step without further purification. $^1$H NMR (400 MHz, DMSO-$d_6$) δ 8.58 (s, 1H), 5.51 (s, 2H).

Preparation 7

4-Bromo-5-fluoro-6-nitro-1,3-dihydroisobenzofuran

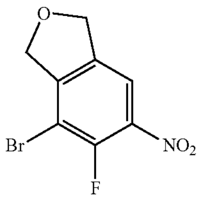

To a stirred mixture of 4-bromo-5-fluoro-6-nitroisobenzofuran-1 (3H)-one (270 g, 978 mmol) in DCM (2,500 mL) was added DIBAL-H (1M in THF, 1,467 mL, 1.467 mol, 1.5 eq.) dropwise at −78° C. under $N_2$. The reaction was stirred for 5 h at −78° C., then was quenched with 5N NaOH (300 mL) at −78° C. The resulting mixture was allowed to warm to RT, then was concentrated. The residue was diluted with EtOAc (2,500 mL), washed with brine (2×1,000 mL) and dried over anhydrous $Na_2SO_4$ and concentrated. The residue was triturated with 10:1 hexanes/EtOAc (550 mL) and filtered. The solids were dried (190 g, 683.4 mmol) then dissolved in DCM (1,500 mL) and treated dropwise with $Et_3SiH$ (662 mL, 4.10 mol, 6 eq.) at 0° C. The reaction was stirred for 20 min at 0° C. TFA (152 mL, 2.05 mol, 3 eq.) was added dropwise at 0° C. The ice bath was removed, and the reaction was stirred at RT for ~18 h. The reaction was concentrated to an oil, which was diluted with EtOAc (2,000 mL), washed with sat. aq. $Na_2CO_3$ (2×500 mL) and brine (2×500 mL), dried over anhydrous $Na_2SO_4$, filtered and concentrated to obtain the title compound (110 g, 42%) which was used in a subsequent step without further purification. $^1$H NMR (400 MHz, DMSO-$d_6$) δ 8.16 (d, J=6.2 Hz, 1H), 5.18-5.15 (m, 2H), 5.11-5.06 (m, 2H).

Preparation 8

7-Bromo-6-fluoro-1,3-dihydroisobenzofuran-5-amine

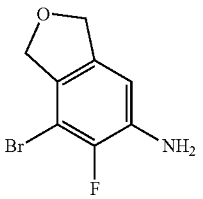 [SMILES: Nc1cc2c(c(Br)c1F)COC2]

To a stirred mixture of 4-bromo-5-fluoro-6-nitro-1,3-dihydroisobenzofuran (110 g, 420 mmol) and $NH_4Cl$ (112.3 g, 2.10 mol, 5 eq.) in EtOH (1,000 mL) and $H_2O$ (200 mL) was added Fe (117.22 g, 2.09 mol, 5 eq.) in portions at RT, then stirred for ~18 h at 80° C. The mixture was filtered and concentrated. The mixture was diluted with $H_2O$ (500 mL) and extracted with EtOAc (2×1,000 mL). The combined organic layers were washed with brine (2×500 mL), dried over anhydrous $Na_2SO_4$, filtered and concentrated. The residue was purified on silica (25% to 50% EtOAc/Hex) to afford the title compound (70 g, 72%) as a yellow solid. MS (ES) m/z=231 (M+1).

Preparation 9

(4-Chloro-1,2-phenylene)dimethanol

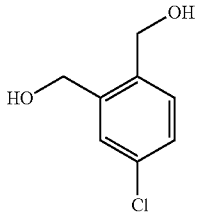

To a stirred mixture of $LiAlH_4$ (1.9 L, 2.74 mol, 2 eq., 2.5 M in THF) in THF (1 L) was added 4-chlorophthalic anhydride (250 g, 1.34 mol, 1.00 eq.) in THF (500 mL) dropwise at −20° C. under $N_2$. The resulting mixture was stirred for 30 min at 45° C. under $N_2$. The reaction was quenched by the addition of $H_2O$ (1.5 L) and 15% NaOH (500 mL) at RT. The mixture was filtered, and the filter cake was washed with MTBE (3×250 mL). The filtrate was extracted with MTBE (3×1.5 L). The combined organic layers were washed with brine (2×2 L) and dried over anhydrous $Na_2SO_4$. After filtration, the filtrate was concentrated under reduced pressure to obtain the title compound (219.5 g, 93%) as an off-white solid. $^1$H NMR (300 MHz, DMSO-$d_6$) δ 7.45-7.36 (m, 2H), 7.28 (dd, J=8.2 Hz, 1H), 5.40-5.13 (m, 2H), 4.54 (s, 2H), 4.49 (s, 2H).

Preparation 10

5-Chloro-1,3-dihydroisobenzofuran

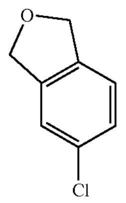

To a stirred mixture of (4-chloro-1,2-phenylene)dimethanol (219.5 g, 1.271 mol) and dimethyl carbonate (458.2 g, 5.082 mol, 4 eq.) in ACN (3 L) was added NaOMe (137.4 g, 2.544 mol, 2 eq.) in portions at RT. The resulting mixture was stirred for ~18 h at 80° C. under $N_2$. The mixture was concentrated under reduced pressure, diluted with $H_2O$ (2 L) and extracted with EtOAc (3×2 L). The combined organic layers were washed with brine (2×2 L) and dried over anhydrous $Na_2SO_4$. After filtration, the filtrate was concentrated under reduced pressure. The residue was purified on silica (10:1 to 8:1 hex/EtOAc) to obtain the title compound (165 g, 82%) as a light-brown solid. $^1$H NMR (300 MHz, DMSO-$d_6$) δ 7.42-7.37 (m, 1H), 7.33 (d, J=1.4 Hz, 2H), 4.99 (s, 4H).

Preparation 11

5-Chloro-6-nitro-1,3-dihydroisobenzofuran

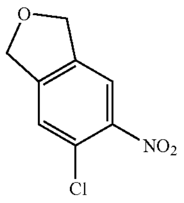 [SMILES: O=[N+]([O-])c1cc2c(cc1Cl)COC2]

A solution of 5-chloro-1,3-dihydroisobenzofuran (110 g, 712 mmol) in $H_2SO_4$ (700 mL) at −10° C. was charged with a solution of $KNO_3$ (64.74 g, 640 mmol, 0.9 eq.) in $H_2SO_4$ (200 mL) dropwise at −5° C.-0° C. The resulting mixture was stirred for additional 30 min at 0° C. and then was slowly added to stirred ice-cooled $H_2O$. The precipitated solids were collected by filtration and washed with $H_2O$ (3×1 L). The filter cake was dried in vacuo to afford the title compound (110 g, 77%) as a light-brown solid which was used in a subsequent step without further purification. $^1$H NMR (400 MHz, DMSO-$d_6$) δ 8.05 (s, 1H), 7.75 (s, 1H), 5.07-5.02 (m, 4H).

Preparation 12

4-Bromo-5-chloro-6-nitro-1,3-dihydroisobenzofuran

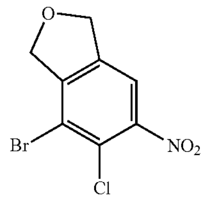 [SMILES: O=[N+]([O-])c1cc2c(c(Br)c1Cl)COC2]

To a stirred solution of 5-chloro-6-nitro-1,3-dihydroisobenzofuran (125 g, 626 mmol) in $H_2SO_4$ (700 mL) was added 1,3-dibromo-5,5-dimethylimidazolidine-2,4-dione (179.1 g, 626.3 mmol, 1 eq.) in portions at −10° C. The mixture was stirred for 1 h at −10° C. then slowly was added to stirred ice-cooled $H_2O$. The precipitated solids were collected by filtration and washed with $H_2O$ (3×0.5 L). The filter cake was dried in vacuo and purified on silica (10:1 to 5:1 Hex/EtOAc) to obtain the title compound (83.5 g, 47.9%) as a white solid. $^1$H NMR (300 MHz, DMSO-$d_6$) δ 8.07 (d, J=1.1 Hz, 1H), 5.19 (dt, J=2.3, 1.1 Hz, 2H), 5.08 (t, 2H).

Preparation 13

7-Bromo-6-chloro-1,3-dihydroisobenzofuran-5-amine

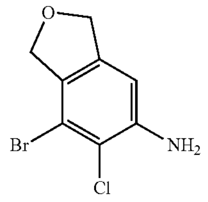 [SMILES: Nc1cc2c(c(Br)c1Cl)COC2]

To a stirred mixture of 4-bromo-5-chloro-6-nitro-1,3-dihydroisobenzofuran (37.0 g, 133 mmol) and $NH_4Cl$ (42.64 g, 797.2 mmol, 6 eq.) in EtOH (200 mL) and $H_2O$ (40 mL) was added Fe (44.52 g, 797.2 mmol, 6 equiv.) in portions at RT. The resulting mixture was stirred for ~18 h at 80° C. The resulting mixture was filtered hot and the filter cake was washed with EtOAc (3×500 mL). The filtrate was concentrated under reduced pressure and was purified on silica (15:1 to 10:1 Hex/EtOAc) to obtain the title compound (25 g, 76%) as a light-yellow solid. MS (ES) m/z=248 (M+1).

Preparation 14

Ethyl N-[(7-bromo-6-fluoro-1,3-dihydroisobenzofuran-5-yl)carbamothioyl]carbamate

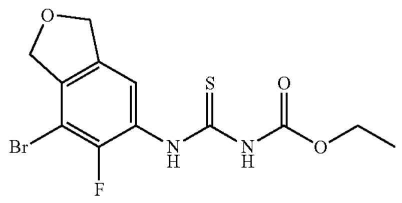 [SMILES: CCOC(=O)NC(=S)Nc1cc2c(c(Br)c1F)COC2]

A solution of 7-bromo-6-fluoro-1,3-dihydroisobenzofuran-5-amine (20.4 g, 87.9 mmol) in DCM (550 mL) was charged with ethoxycarbonyl isothiocyanate (9.7 mL, 82 mmol, 0.93 eq.) slowly via addition funnel and subsequently stirred at RT for ~4 h. The solids were filtered. The filtrate was concentrated, suspended in DCM (100 mL) and hexanes (350 mL) and stirred at RT. The resultant filtered solids and previous filtered solids were dried under vacuum at 50° C. for 2 h. The batches were combined to obtain the title compound (32.6 g, quantitative) as a white solid. MS (ES) m/z=363 (M+1).

Preparation 15

Ethyl N-[(7-bromo-6-chloro-1,3-dihydroisobenzofuran-5-yl)carbamothioyl]carbamate

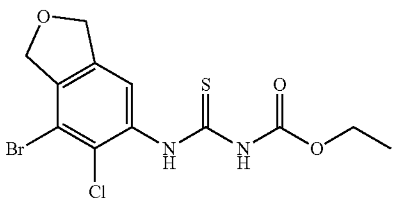

7-Bromo-6-chloro-1,3-dihydroisobenzofuran-5-amine was used in a manner analogous to the method of Preparation 14 to afford the title compound (14 g, 92%) as a white solid. MS (ES) m/z=379 (M+1).

Preparation 16

Ethyl (((7-bromo-6-fluoro-1,3-dihydroisobenzofuran-5-yl)amino)(ethylthio)methylene)carbamate

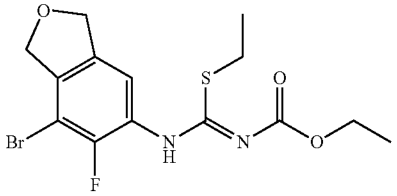 [SMILES: CCOC(=O)/N=C(/Nc1cc2c(c(Br)c1F)COC2)SCC]

A 2 L 3-necked RBF, equipped with an overhead stirrer, dropping funnel and thermocouple was charged with a suspension of ethyl N-[(7-bromo-6-fluoro-1,3-dihydroisobenzofuran-5-yl)carbamothioyl]carbamate (32.6 g, 89.8 mmol) and acetone (450 mL). To this was added solid $K_2CO_3$ (37.2 g, 269 mmol, 3.00 eq.) in several portions, followed by the dropwise addition of EtI (7.2 mL, 90 mmol, 1.0 eq.) over 20 min. The mixture was stirred at RT for ~18 h. The solids were filtered and the filtrate was concentrated and partitioned between DCM (500 mL) and $H_2O$ (500 mL). The organics were further washed with brine and dried over anhydrous $Na_2SO_4$, filtered and concentrated. The residue was purified on silica (0 to 30% EtOAc/Hex) to obtain the title compound (30.9 g, 85.6%) as a white solid. MS (ES) n/z=391 (M+1).

Preparation 17

Ethyl (((7-bromo-6-chloro-1,3-dihydroisobenzofuran-5-yl)amino)(ethylthio)methylene)carbamate

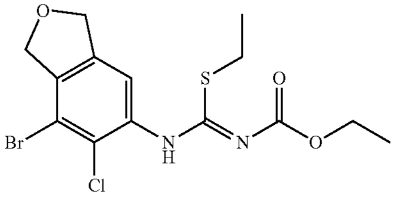 [SMILES: CCOC(=O)/N=C(/Nc1cc2c(c(Br)c1Cl)COC2)SCC]

Ethyl N-[(7-bromo-6-chloro-1,3-dihydroisobenzofuran-5-yl)carbamothioyl]carbamate was used in a manner analogous to the method of Preparation 16 to afford the title compound (15.4 g, crude) as a brown solid. MS (ES) m/z=407 (M+1).

Preparation 18

6-Bromo-3-(ethylthio)-5-fluoro-7,9-dihydrofuro[3,4-f]quinazolin-1-ol

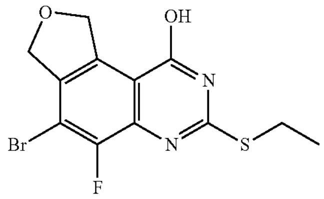 [SMILES: CCSc1nc(O)c2c3c(c(Br)c(F)c2n1)COC3]

A 2 L 4-necked RBF was equipped with an overhead stirrer, dropping funnel, $N_2$ inlet and thermocouple and was purged with $N_2$. NMP (anhydrous, 300 mL) was added. The mixture was heated to 175° C. In a second flask, ethyl (((7-bromo-6-fluoro-1,3-dihydroisobenzofuran-5-yl)amino)(ethylthio)methylene)carbamate (22.63 g, 57.83 mmol) and NMP (anhydrous, 100 mL) were combined and stirred under $N_2$ until a homogeneous solution was obtained. When the first flask had reached 175° C., the contents of the second flask were poured into the dropping funnel and were added dropwise but rapidly to the hot NMP. After 30 min, the heat was turned off and the reaction cooled to 45° C. $H_2O$ (500 mL) was slowly added and the mixture was stirred at RT for 1 h. The solids were filtered, rinsed with $H_2O$ (300 mL) and dried under vacuum at 50° C. for ~18 h to afford the title compound (15.2 g, 73%) as an off-white solid. MS (ES) m/z=363 (M+1).

Preparation 19

6-Bromo-5-chloro-3-(ethylthio)-7,9-dihydrofuro[3,4-f]quinazolin-1-ol

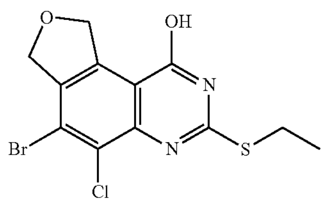 [SMILES: CCSc1nc(O)c2c3c(c(Br)c(Cl)c2n1)COC3]

Ethyl (((7-bromo-6-chloro-1,3-dihydroisobenzofuran-5-yl)amino)(ethylthio)methylene)carbamate was used in a manner analogous to the method of Preparation 18 to afford the title compound (11.4 g, 86%) as a white solid. MS (ES) n/z=361 (M+1).

Preparation 20

6-Bromo-3-(ethylthio)-5-fluoro-1-((2-(trimethylsilyl)ethoxy)methoxy)-7,9-dihydrofuro[3,4-f]quinazoline

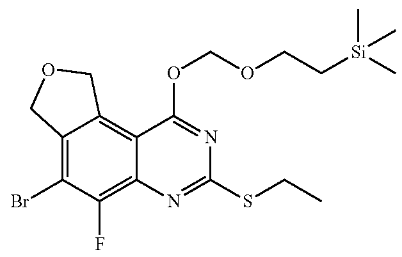 [SMILES: CCSc1nc(OCOCC[Si](C)(C)C)c2c3c(c(Br)c(F)c2n1)COC3]

A mixture of 6-bromo-3-(ethylthio)-5-fluoro-7,9-dihydrofuro[3,4-f]quinazolin-1-ol (30.1 g, 87.3 mmol) in DMF was heated to -70° C. to dissolve the solids, then cooled to 40° C. To the mixture was added diisopropylethylamine (30.4 mL, 175 mmol) and 2-(chloromethoxyethyl)trimethyl silane (23.2 mL, 131 mmol). The reaction mixture was stirred for 1 h at 40° C., then cooled to room temperature and diluted with water (1 L) and EtOAc (500 mL). The layers were separated and the organic layer was washed with brine (2×500 mL), dried over magnesium sulfate, filtered, and concentrated under reduced pressure to give the crude title compound (49.2 g, 85% purity) as a yellow oil. MS (ES) m/z=475 (M+1).

Preparation 1A

6-Bromo-3-(ethylthio)-5-fluoro-2-((2-(trimethylsilyl)ethoxy)methyl)-7,9-dihydrofuro[3,4-f]quinazolin-1(2H)-one

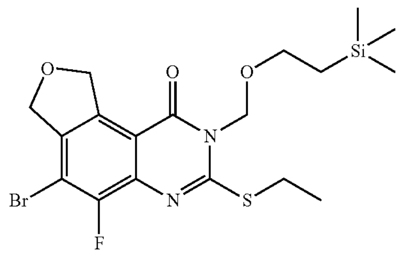

6-Bromo-3-(ethylthio)-5-fluoro-7,9-dihydrofuro[3,4-f]quinazolin-1-ol and 2-(chloromethoxyethyl)trimethyl silane were used in a manner analogous to the method of Preparation 20 to afford the title compound. MS (ES) m/z=475 (M+1).

Preparation 21

6-Bromo-5-chloro-3-(ethylthio)-1-((2-(trimethylsilyl)ethoxy)methoxy)-7,9-dihydrofuro[3,4-f]quinazoline

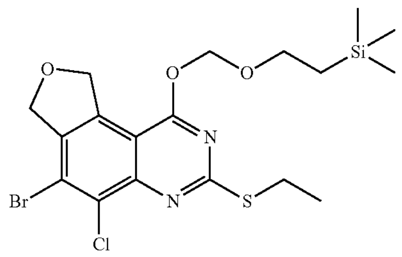 [SMILES: CCSc1nc(OCOCC[Si](C)(C)C)c2c3c(c(Br)c(Cl)c2n1)COC3]

6-Bromo-5-chloro-3-(ethylthio)-7,9-dihydrofuro[3,4-f]quinazolin-1-ol was used in a manner analogous to the method of Preparation 20 to afford the title compound (10.5 g, 96%) as a pink solid. MS (ES) m/z=491 (M+1).

Preparation 2A

6-Bromo-5-chloro-3-(ethylthio)-2-((2-(trimethylsilyl)ethoxy)methyl)-7,9-dihydrofuro[3,4-f]quinazolin-1(2H)-one

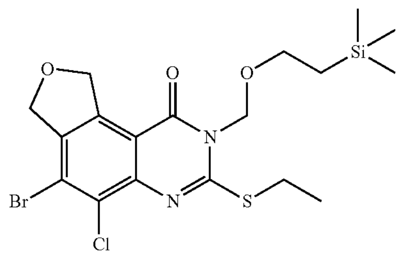 [SMILES: CCSc1nc2c(Cl)c(Br)c3c(c2c(=O)n1COCC[Si](C)(C)C)COC3]

6-Bromo-5-chloro-3-(ethylthio)-7,9-dihydrofuro[3,4-f]quinazolin-1-ol was used in a manner analogous to the method of Preparation 20 to afford the title compound. MS (ES) m/z=491 (M+1).

Preparation 22

6-Bromo-1-chloro-3-(ethylthio)-5-fluoro-7,9-dihydrofuro[3,4-f]quinazoline

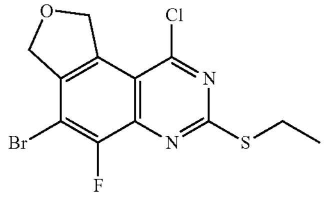

A 5 L 3-necked RBF, equipped with a dropping funnel, thermocouple and an overhead stirrer was charged with a solution of DMF (50 mL, 646 mmol, 4 eq.) in DCM (1,000 mL) and was placed in an ice/water bath and cooled to ~4° C. Oxalyl chloride (50.0 mL, 576 mmol, 4 eq.) was added dropwise via addition funnel over ~40 min. When the addition was complete, the reaction was stirred at ~4° C. for 15 min. Solid 6-bromo-3-(ethylthio)-5-fluoro-7,9-dihydrofuro[3,4-f]quinazolin-1-ol (50.4 g, 140 mmol) was added in several portions to the reaction mixture and the resulting suspension was stirred at –4° C. for 30 min. The ice bath was removed and the reaction was allowed to warm to RT and stir for 1 h. Then $H_2O$ (1 L) was added and the mixture was stirred for 15 min. The mixture was partitioned and the organic layer was washed with brine (1 L) and dried over anhydrous $Na_2SO_4$, filtered and concentrated. The residue was purified on silica, eluting with DCM/Hex (60% to 90%) to obtain the title compound (45.1 g, 89%) as a white solid. MS (ES) m/z=363 (M+1).

Preparation 23

6-Bromo-1,5-dichloro-3-(ethylthio)-7,9-dihydrofuro[3,4-f]quinazoline

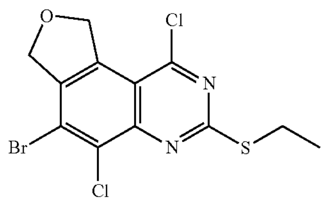 [SMILES: CCSc1nc(Cl)c2c3c(c(Br)c(Cl)c2n1)COC3]

6-Bromo-5-chloro-3-(ethylthio)-7,9-dihydrofuro[3,4-f]quinazolin-1-ol was used in a manner analogous to the method of Preparation 22 to afford the title compound (0.81 g, 77%) as a yellow solid. MS (ES) m/z=382 (M+1).

Preparation 24 tert-Butyl (4-(5-chloro-3-(ethylthio)-1-((2-(trimethylsilyl)ethoxy)methoxy)-7,9-dihydrofuro[3,4-f]quinazolin-6-yl)-7-fluorobenzo[d]thiazol-2-yl)carbamate

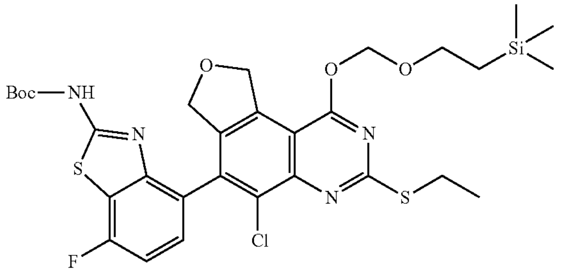 [SMILES: CCSc1nc(OCOCC[Si](C)(C)C)c2c3c(c(-c4ccc(F)c5sc(NC(=O)OC(C)(C)C)nc45)c(Cl)c2n1)COC3]

A mixture of 6-bromo-5-chloro-3-(ethylthio)-1-((2-(trimethylsilyl)ethoxy)methoxy)-7,9-dihydrofuro[3,4-f]quinazoline (2.00 g, 4.07 mmol), (2-((tert-butoxycarbonyl)amino)-7-fluorobenzo[d]thiazol-4-yl)boronic acid (1.52 g, 4.88 mmol), tripotassium phosphate (2.59 g, 12.2 mmol), and [1,1'-bis(diphenylphosphino)ferrocene]palladium(II) dichloride (0.298 g, 0.41 mmol) in 1,4-dioxane (10 mL) and water (0.4 mL) was stirred at 90° C. for 16 h, then concentrated under reduced pressure. The residue was purified on silica, eluting with 0-100% EtOAc in heptane to obtain the title compound (1.90 g, 69%) as a yellow solid. MS (ES) m/z=679 (M+1).

Preparation 3A tert-Butyl (4-(5-chloro-3-(ethylthio)-1-oxo-2-((2-(trimethylsilyl)ethoxy)methyl)-1,2,7,9-tetrahydrofuro[3,4-f]quinazolin-6-yl)-7-fluorobenzo[d]thiazol-2-yl)carbamate

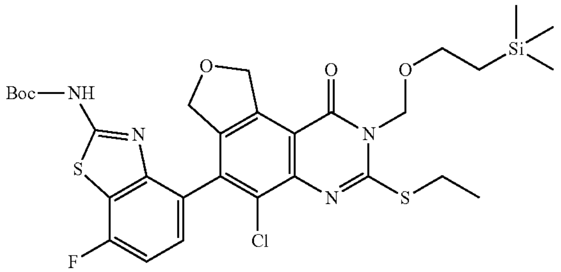 [SMILES: CCSc1nc2c(Cl)c(-c3ccc(F)c4sc(NC(=O)OC(C)(C)C)nc34)c3c(c2c(=O)n1COCC[Si](C)(C)C)COC3]

6-Bromo-5-chloro-3-(ethylthio)-2-((2-(trimethylsilyl)ethoxy)methyl)-7,9-dihydrofuro[3,4-f]quinazolin-1 (2H)-one was used in a manner analogous to the method of Preparation 24 to afford the title compound. MS (ES) m/z=679 (M+1).

Preparation 25 tert-Butyl (4-(5-chloro-3-(ethylthio)-1-hydroxy-7,9-dihydrofuro[3,4-f]quinazolin-6-yl)-7-fluorobenzo[d]thiazol-2-yl)carbamate

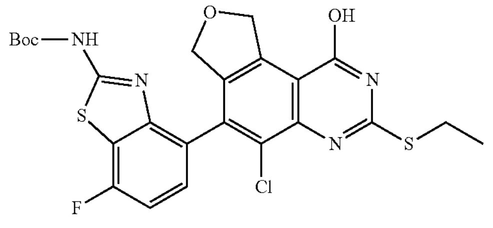

To a mixture of tert-butyl (4-(5-chloro-3-(ethylthio)-1-((2-(trimethylsilyl)ethoxy)methoxy)-7,9-dihydrofuro[3,4-f]quinazolin-6-yl)-7-fluorobenzo[d]thiazol-2-yl)carbamate (1.90 g, 2.80 mmol) and DMF (10 mL) was added cesium fluoride (2.97 g, 19.6 mmol). The mixture was stirred at 120° C. for 24 h, then cooled to room temperature and diluted with water (50 mL). The resulting solids were filtered and dried to obtain the title compound (1.28 g, 83%) as a yellow solid. MS (ES) m/z=549 (M+1).

Alternate Preparation 25 tert-Butyl (4-(5-chloro-3-(ethylthio)-1-hydroxy-7,9-dihydrofuro[3,4-f]quinazolin-6-yl)-7-fluorobenzo[d]thiazol-2-yl)carbamate

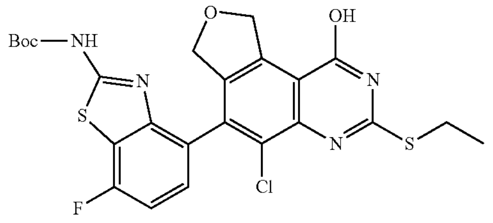 [SMILES: CCSc1nc(O)c2c3c(c(-c4ccc(F)c5sc(NC(=O)OC(C)(C)C)nc45)c(Cl)c2n1)COC3]

tert-Butyl (4-(5-chloro-3-(ethylthio)-1-oxo-2-((2-(trimethylsilyl)ethoxy)methyl)-1,2,7,9-tetrahydrofuro[3,4-f]quinazolin-6-yl)-7-fluorobenzo[d]thiazol-2-yl)carbamate was used in a manner analogous to the method of Preparation 25 from tert-butyl (4-(5-chloro-3-(ethylthio)-1-((2-(trimethylsilyl)ethoxy)methoxy)-7,9-dihydrofuro[3,4-f]quinazolin-6-yl)-7-fluorobenzo[d]thiazol-2-yl)carbamate to afford the title compound. MS (ES) m/z=549 (M+1).

Preparation 26 tert-Butyl (4-(1,5-dichloro-3-(ethylthio)-7,9-dihydrofuro[3,4-f]quinazolin-6-yl)-7-fluorobenzo[d]thiazol-2-yl)carbamate

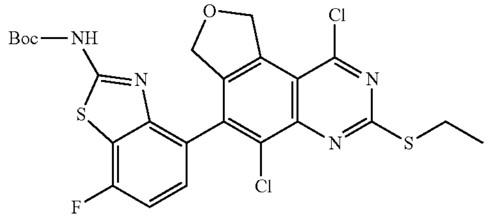 [SMILES: CCSc1nc(Cl)c2c3c(c(-c4ccc(F)c5sc(NC(=O)OC(C)(C)C)nc45)c(Cl)c2n1)COC3]

To a solution of tert-butyl (4-(5-chloro-3-(ethylthio)-1-hydroxy-7,9-dihydrofuro[3,4-f]quinazolin-6-yl)-7-fluorobenzo[d]thiazol-2-yl)carbamate (0.219 g, 0.40 mmol) in DCM (3 mL) was added chloromethylene(dimethyl)ammonium chloride (0.061 g, 0.48 mmol) portionwise. The mixture was stirred at room temperature for 2 h, diluted with water (100 mL), and extracted with DCM (200 mL). The organics were washed with brine (200 mL), dried over anhydrous $Na_2SO_4$, filtered, and concentrated under reduced pressure to give the title compound (0.23 g, crude) as a yellow solid. MS (ES) m/z=567 (M+1).

Preparation 27 tert-Butyl (2S,3S)-3-(isopropylamino)-2-methylpyrrolidine-1-carboxylate

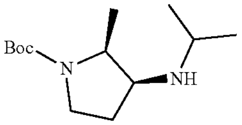 [SMILES: CC(C)N[C@H]1CCN(C(=O)OC(C)(C)C)[C@H]1C]

tert-Butyl (2S,3S)-3-amino-2-methylpyrrolidine-1-carboxylate (0.500 g, 2.50 mmol), acetone (0.275 mL, 3.74 mmol), and sodium triacetoxyborohydride (1.59 g, 7.49 mmol) were dissolved in methanol (6 mL). The mixture was heated at 50° C. After 18 h, the mixture was cooled, concentrated under reduced pressure, and diluted with saturated aqueous sodium bicarbonate (20 mL). The mixture was extracted with EtOAc (3×50 mL). The combined organic layers were washed with brine (25 mL), dried over anhydrous $Na_2SO_4$, filtered, and concentrated under reduced pressure to give the crude title compound (0.600 g) as a colorless oil. MS (ES) m/z=243 (M+1).

The following compounds in Table 2 were prepared in similar manner as described in Preparation 27. Different reductive amination conditions, such as sodium cyanoborohydride with sodium dihydrogen phosphate, may have been substituted. Various methods were used to purify the compounds, which would be apparent to one skilled in the art.

TABLE 2

| Preparation | Chemical Name | Structure | MS (ES) m/z (M + 1) |
|---|---|---|---|
| 28 | tert-Butyl (2S,3S)-3-(dimethylamino)-2-methylpyrrolidine-1-carboxylate | 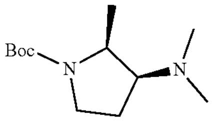 [SMILES: C[C@H]1[C@@H](N(C)C)CCN1C(=O)OC(C)(C)C] | 229 |
| 29 | tert-Butyl (2S,3S)-3-(isopropyl (methyl)amino)-2-methylpyrrolidine-1-carboxylate | 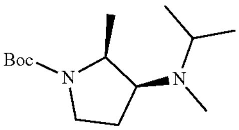 [SMILES: CC(C)N(C)[C@H]1CCN(C(=O)OC(C)(C)C)[C@H]1C] | 257 |
| 30 | tert-Butyl (2S,3S)-3-(diethylamino)-2-methylpyrrolidine-1-carboxylate | 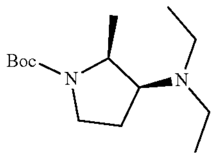 [SMILES: CCN(CC)[C@H]1CCN(C(=O)OC(C)(C)C)[C@H]1C] | 257 |
| 31 | tert-Butyl (2S,3S)-3-(ethylamino)-2-methylpyrrolidine-1-carboxylate | 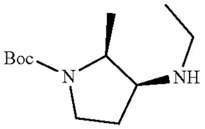 [SMILES: CCN[C@H]1CCN(C(=O)OC(C)(C)C)[C@H]1C] | 229 |
| 32 | tert-Butyl (2S,3S)-3-(ethyl(methyl) amino)-2-methylpyrrolidine-1-carboxylate | 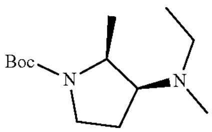 [SMILES: CCN(C)[C@H]1CCN(C(=O)OC(C)(C)C)[C@H]1C] | 243 |
| 4A | tert-butyl (3R,4S)-3-(isopropylamino)-4-methylpyrrolidine-1-carboxylate | 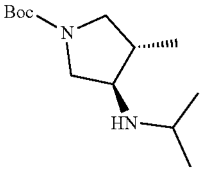 [SMILES: CC(C)N[C@H]1CN(C(=O)OC(C)(C)C)C[C@@H]1C] | 243 |
| 5A | tert-butyl (3R,4S)-3-(isopropyl(methyl) amino)-4-methylpyrrolidine-1-carboxylate | 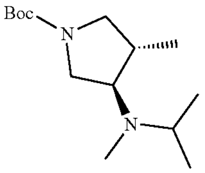 [SMILES: CC(C)N(C)[C@H]1CN(C(=O)OC(C)(C)C)C[C@@H]1C] | 257 |
| 6A [1] | tert-butyl (2S,3S)-3-((2-methoxyethyl) amino)-2-methylpyrrolidine-1-carboxylate | 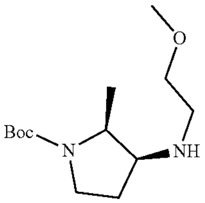 [SMILES: COCCN[C@H]1CCN(C(=O)OC(C)(C)C)[C@H]1C] | 259 |
| 7A | tert-butyl (2S, 3S)-3-((2-methoxyethyl) (methyl) amino)-2-methylpyrrolidine-1-carboxylate | 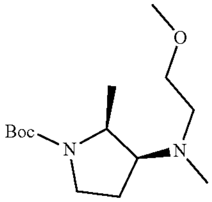 [SMILES: COCCN(C)[C@H]1CCN(C(=O)OC(C)(C)C)[C@H]1C] | 273 |

1 Generated in stepwise preparation of Preparation 7A; used in situ

Preparation 8A tert-Butyl (2S,3S)-3-(ethyl(methyl)amino)-2-methylpyrrolidine-1-carboxylate

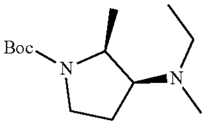 [SMILES: CCN(C)[C@H]1CCN(C(=O)OC(C)(C)C)[C@H]1C]

To a solution of tert-butyl (S)-2-methyl-3-oxopyrrolidine-1-carboxylate (1.00 g, 5.02 mmol), acetic acid (0.287 mL, 5.02 mmol), and N-methylethanamine (0.445 g, 7.53 mmol) in DCM (5 mL) was added sodium triacetoxyborohydride (1.70 g, 8.03 mmol) portionwise. The mixture was stirred at room temperature. After 22 h, the mixture was cooled to 0° C. and quenched with aqueous sodium bicarbonate. The two layers were separated. The aqueous layer was extracted with DCM. The combined organic layers were washed with brine, dried over anhydrous $Na_2SO_4$, filtered, and concentrated under reduced pressure. The residue was purified by reversed phase purification (C18 column), eluting with 0-100% acetonitrile in (0.1% formic acid in water), to give the title compound (1.32 g) as a colorless oil. MS (ES) m/z=243 (M+1).

Preparation 9A tert-Butyl (2S)-3-(azetidin-1-yl)-2-methylpyrrolidine-1-carboxylate Boc, N

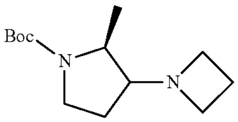 [SMILES: C[C@H]1C(N2CCC2)CCN1C(=O)OC(C)(C)C]

Azetidine was used in a manner analogous to the method of Preparation 8A to afford the title compound (0.59 g, 85%) as a yellow oil. MS (ES) m/z=241 (M+1).

Preparation 10A tert-Butyl (2'S,3'S)-2'-methyl-[1,3'-bipyrrolidine]-1'-carboxylate

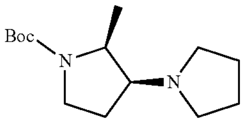 [SMILES: C[C@H]1[C@@H](N2CCCC2)CCN1C(=O)OC(C)(C)C]

Pyrrolidine was used in a manner analogous to the method of Preparation 8A to afford the title compound (0.53 g, 78%) as a yellow oil. MS (ES) n/z=255 (M+1).

Preparation 33 (2S,3S)—N-Isopropyl-2-methylpyrrolidin-3-amine dihydrochloride

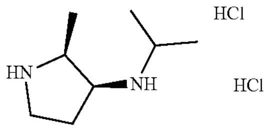

To a mixture of tert-butyl (2S,3S)-3-(isopropylamino)-2-methylpyrrolidine-1-carboxylate (0.600 g, 2.48 mmol) in DCM (3 mL) was added HCl (4M in 1,4-dioxane; 3 mL). The mixture was stirred at room temperature. After 6 h, the mixture was concentrated under reduced pressure to give the crude title compound (0.533 g) as a yellow solid. MS (ES) m/z=143 (M+1).

The following compounds in Table 3 were prepared in similar manner as described in Preparation 33. Different acidic conditions, such as trifluoroacetic acid, may have been substituted. Various methods were used to purify the compounds, which would be apparent to one skilled in the art.

TABLE 3

| Preparation | Chemical Name | Structure | MS (ES) m/z (M + 1) |
|---|---|---|---|
| 34 | (2S,3S)-N,N,2-Trimethylpyrrolidin-3-amine dihydrochloride | 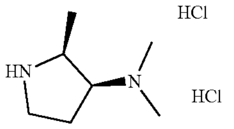 | 129 |
| 35 | (2S,3S)-N-Isopropyl-N,2-dimethylpyrrolidin-3-amine dihydrochloride | 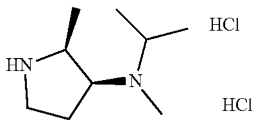 | 157 |
| 36 | (2S,3S)-N-Isopropyl-N,2-dimethylpyrrolidin-3-amine | 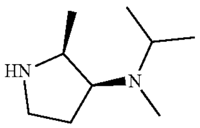 | 157 |
| 37 | (2S,3S)-N,N-Diethyl-2-methylpyrrolidin-3-amine | 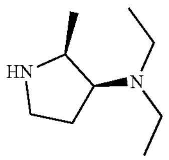 | 157 |
| 38 | (2S,3S)-N-Ethyl-N,2-dimethylpyrrolidin-3-amine dihydrochloride | 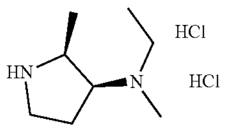 | 143 |
| 11A | (3R,4S)-N-Isopropyl-N,4-dimethylpyrrolidin-3-amine dihydrochloride | 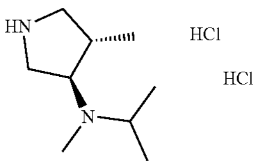 | 157 |
| 12A | (2S)-3-(Azetidin-1-yl)-2-methylpyrrolidine | 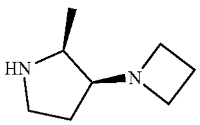 | 141 |
| 13A | (2'S,3'S)-2'-Methyl-1,3'-bipyrrolidine | 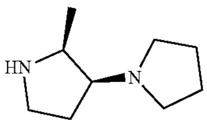 | 155 |

TABLE 3-continued

| Preparation | Chemical Name | Structure | MS (ES) m/z (M + 1) |
|---|---|---|---|
| 14A | (2S,3S)-N-(2-methoxyethyl)-N,2-dimethylpyrrolidin-3-amine dihydrochloride | 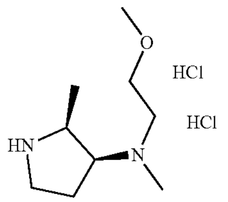 | 173 |

Preparation 39

(6S)-3-Amino-1,6-dimethylpiperidin-2-one

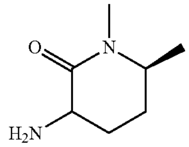

(S)-1,6-Dimethylpiperidin-2-one. To a solution of (S)-6-methylpiperidin-2-one (0.500 g, 4.42 mmol) in THF (5 mL) was added sodium hydride (60 wt % in mineral oil; 0.212 g, 5.30 mmol). The mixture was stirred at room temperature for 30 min, then cooled to 0° C. A solution of iodomethane (0.41 mL, 6.63 mmol) in THF (0.3 mL) was added dropwise and the mixture was stirred at 0° C. for 5 min, then warmed to room temperature and stirred overnight. The mixture was diluted with water (5 mL) and extracted with EtOAc and DCM. The combined organics were dried over anhydrous $Na_2SO_4$, filtered, and concentrated under reduced pressure to give crude (S)-1,6-dimethylpiperidin-2-one as a white solid. MS (ES) m/z=128 (M+1).

(6S)-3-Chloro-1,6-dimethylpiperidin-2-one. A solution of (S)-1,6-dimethylpiperidin-2-one (0.600 g, 4.72 mmol) in THF (2 mL) was cooled to −78° C. Lithium diisopropylamide (2.0M in THF/heptane/ethylbenzene; 3.07 mL, 6.13 mmol) was added. The mixture was stirred at −78° C. for 20 min, then a solution of tosyl chloride (2.70 g, 14.2 mmol) in THF (0.5 mL) was slowly added. The mixture was stirred at −78° C. for 90 min. The mixture was diluted with water and extracted with DCM. The organics were dried over anhydrous $Na_2SO_4$ and purified on silica, eluting with 0-40% MeOH in DCM to obtain crude (6S)-3-chloro-1,6-dimethylpiperidin-2-one as a brown oil. MS (ES) m/z=162 (M+1).

(6S)-3-Amino-1,6-dimethylpiperidin-2-one. A solution of (6S)-3-chloro-1,6-dimethylpiperidin-2-one (0.250 g, 1.55 mmol) in acetonitrile (5 mL) and ammonium hydroxide (5 mL) was heated under microwave irradiation at 80° C. for 22 h. The mixture was concentrated under reduced pressure to give the title compound (0.220 g, crude) as a brown oil. MS (ES) m/z=143 (M+1).

Preparation 40

(6R)-3-Amino-1,6-dimethylpiperidin-2-one

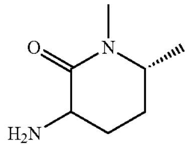

(R)-6-methylpiperidin-2-one was used in a manner analogous to the method of Preparation 39 to afford the title compound (0.220 g, crude) as a brown oil. MS (ES) m/z=143 (M+1).

Preparation 41

(R)-3-((6-Bromo-3-(ethylthio)-5-fluoro-7,9-dihydrofuro[3,4-f]quinazolin-1-yl)amino)-1-methylpiperidin-2-one

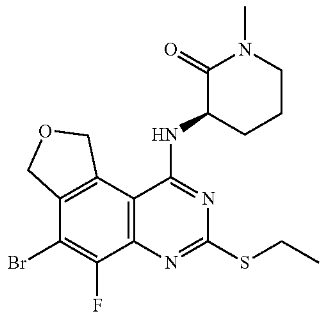

To a mixture of 6-bromo-1-chloro-3-(ethylthio)-5-fluoro-7,9-dihydrofuro[3,4-f]quinazoline (10.5 g, 28.9 mmol) and (R)-3-amino-1-methylpiperidin-2-one hydrochloride (4.75 g, 28.9 mmol) in acetonitrile (100 mL) was added triethylamine (28.3 mL, 202 mmol). The mixture was stirred at room temperature. After 2 h, the mixture was diluted with water (600 mL) and filtered. The solids were washed with acetonitrile (2×80 mL) and dried under vacuum to obtain the title compound (9.04 g, 69%) as a white solid. MS (ES) m/z=457 (M+1).

The following compounds in Table 4 were prepared in similar manner as described in Preparation 41. Various methods were used to purify the compounds, which would be apparent to one skilled in the art.

TABLE 4

| Preparation | Chemical Name | Structure | MS (ES) m/z (M + 1) |
|---|---|---|---|
| 42 | (R)-3-((6-Bromo-5-chloro-3-(ethylthio)-7,9-dihydrofuro[3,4-f]quinazolin-1-yl)amino)-1-methylpiperidin-2-one | 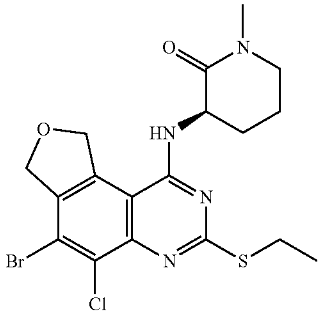 [SMILES: CCSc1nc(N[C@@H]2CCCN(C)C2=O)c2c3c(c(Br)c(Cl)c2n1)COC3] | 471 |
| 43 | (6R)-3-((6-Bromo-3-(ethylthio)-5-fluoro-7,9-dihydrofuro[3,4-f]quinazolin-1-yl)amino)-1,6-dimethylpiperidin-2-one | 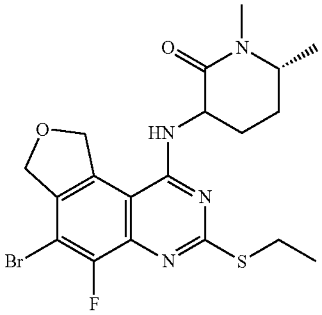 [SMILES: CCSc1nc(NC2CC[C@@H](C)N(C)C2=O)c2c3c(c(Br)c(F)c2n1)COC3] | 469 |
| 44 | (6S)-3-((6-Bromo-3-(ethylthio)-5-fluoro-7,9-dihydrofuro[3,4-f]quinazolin-1-yl)amino)-1,6-dimethylpiperidin-2-one | 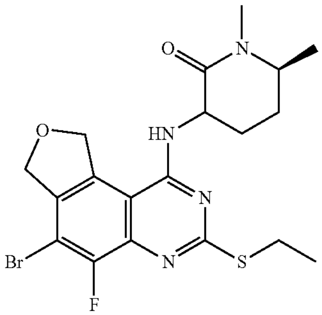 [SMILES: CCSc1nc(NC2CC[C@H](C)N(C)C2=O)c2c3c(c(Br)c(F)c2n1)COC3] | 469 |
| 45 | tert-Butyl (4-(5-chloro-1-(((6S)-1,6-dimethyl-2-oxopiperidin-3-yl)amino)-3-(ethylthio)-7,9-dihydrofuro[3,4-f]quinazolin-6-yl)-7-fluorobenzo[d]thiazol-2-yl)carbamate | 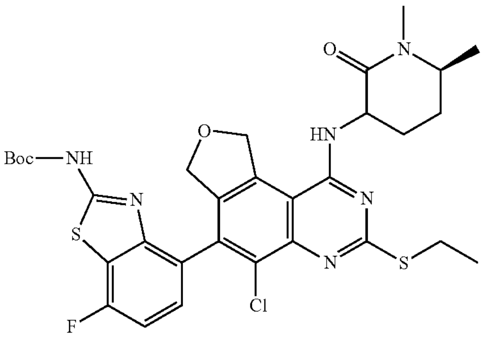 [SMILES: CCSc1nc(NC2CC[C@H](C)N(C)C2=O)c2c3c(c(-c4ccc(F)c5sc(NC(=O)OC(C)(C)C)nc45)c(Cl)c2n1)COC3] | 673 |

TABLE 4-continued

| Preparation | Chemical Name | Structure | MS (ES) m/z (M + 1) |
| --- | --- | --- | --- |
| 15A | tert-butyl (4-(5-chloro-3-(ethylthio)-1-(((R)-1-methyl-2-oxopiperidin-3-yl)amino)-7,9-dihydrofuro[3,4-f]quinazolin-6-yl)-7-fluorobenzo[d]thiazol-2-yl)carbamate | 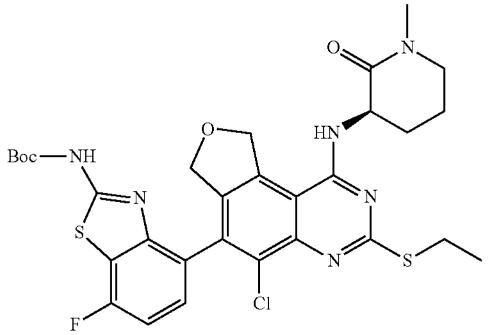 [SMILES: CCSc1nc(N[C@@H]2CCCN(C)C2=O)c2c3c(c(-c4ccc(F)c5sc(NC(=O)OC(C)(C)C)nc45)c(Cl)c2n1)COC3] | 659 |
| 16A | (6R)-3-((6-bromo-5-chloro-3-(ethylthio)-7,9-dihydrofuro[3,4-f]quinazolin-1-yl)amino)-1,6-dimethylpiperidin-2-one | 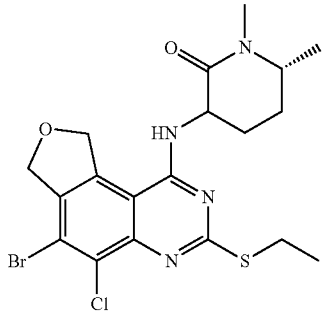 [SMILES: CCSc1nc(NC2CC[C@@H](C)N(C)C2=O)c2c3c(c(Br)c(Cl)c2n1)COC3] | 485 |

Preparation 46 tert-Butyl (4-(5-chloro-3-(ethylthio)-1-(((R)-1-methyl-2-oxopiperidin-3-yl)amino)-7,9-dihydrofuro[3,4-f]quinazolin-6-yl)-5,7-difluorobenzo[d]thiazol-2-yl)carbamate

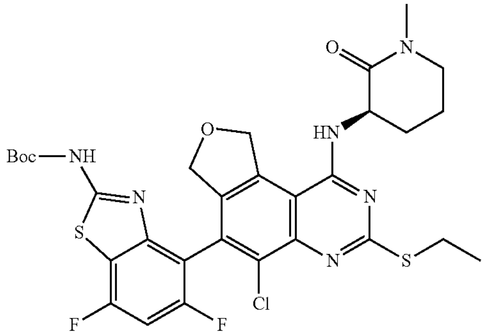 [SMILES: CCSc1nc(N[C@@H]2CCCN(C)C2=O)c2c3c(c(-c4c(F)cc(F)c5sc(NC(=O)OC(C)(C)C)nc45)c(Cl)c2n1)COC3]

To a solution of (R)-3-((6-bromo-5-chloro-3-(ethylthio)-7,9-dihydrofuro[3,4-f]quinazolin-1-yl)amino)-1-methylpiperidin-2-one (4.80 g, 10.2 mmol) and (2-((tert-butoxycarbonyl)amino)-5,7-difluorobenzo[d]thiazol-4-yl)boronic acid (2.69 g, 8.14 mmol) in 1,4-dioxane (400 mL) and water (80 mL) was added dipotassium phosphate (5.32 g, 30.5 mmol), 2-dicyclohexylphosphino-2',4',6'-triisopropylbiphenyl (0.97 g, 2.04 mmol), and XPhos Pd(crotyl)Cl (CAS 1798782-02-1; 1.37 g, 2.04 mmol) portionwise under nitrogen. The mixture was stirred at 80° C. for 1 h, then concentrated under reduced pressure. The residue was diluted with water (250 mL) and extracted with EtOAc (400 mL). The organics were washed with brine (2×250 mL), dried over anhydrous $Na_2SO_4$, filtered, and concentrated under reduced pressure. The crude material was purified on silica, eluting with 50-67% EtOAc in petroleum ether to obtain the title compound (2.3 g, 33%) as a yellow solid. MS (ES) m/z=677 (M+1).

The following compounds in Table 5 were prepared in similar manner as described in Preparations 24 or 46. Different coupling conditions, such as base, ligands or palladium sources may have been substituted. Various methods were used to purify the compounds, which would be apparent to one skilled in the art.

TABLE 5

| Preparation | Chemical Name | Structure | MS (ES) m/z (M + 1) |
|---|---|---|---|
| 47 | tert-Butyl (4-(1-(((6R)-1,6-dimethyl-2-oxopiperidin-3-yl)amino)-3-(ethylthio)-5-fluoro-7,9-dihydrofuro[3,4-f]quinazolin-6-yl)-7-fluorobenzo[d]thiazol-2-yl)carbamate | 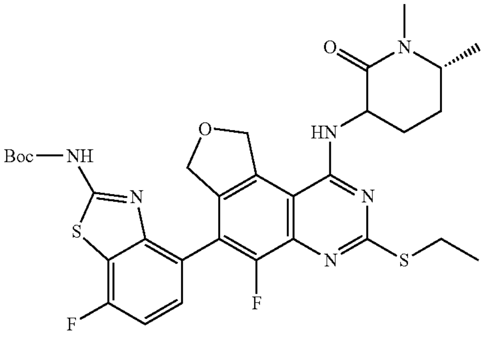 [SMILES: CCSc1nc(NC2CC[C@@H](C)N(C)C2=O)c2c3c(c(-c4ccc(F)c5sc(NC(=O)OC(C)(C)C)nc45)c(F)c2n1)COC3] | 657 |
| 48 | tert-Butyl (4-(1-(((6S)-1,6-dimethyl-2-oxopiperidin-3-yl)amino)-3-(ethylthio)-5-fluoro-7,9-dihydrofuro[3,4-f]quinazolin-6-yl)-7-fluorobenzo[d]thiazol-2-yl)carbamate | 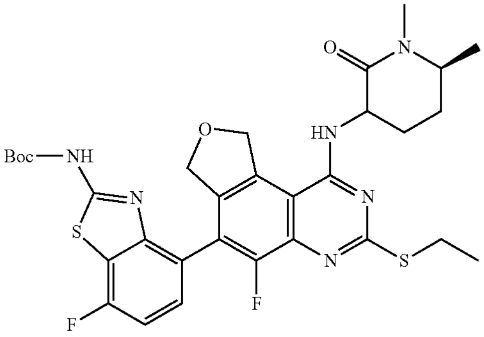 [SMILES: CCSc1nc(NC2CC[C@H](C)N(C)C2=O)c2c3c(c(-c4ccc(F)c5sc(NC(=O)OC(C)(C)C)nc45)c(F)c2n1)COC3] | 657 |
| 49 | tert-Butyl (4-(3-(ethylthio)-5-fluoro-1-(((R)-1-methyl-2-oxopiperidin-3-yl)amino)-7,9-dihydrofuro[3,4-f]quinazolin-6-yl)-7-fluorobenzo[d]thiazol-2-yl)carbamate | 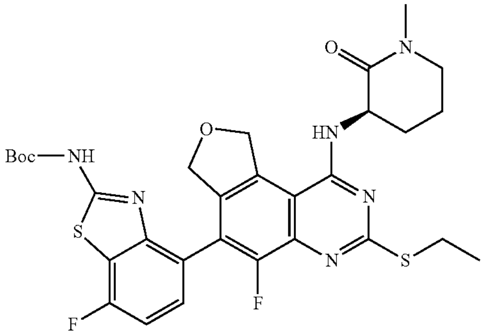 | 643 |
| 50 | tert-Butyl (4-(5-chloro-3-(ethylthio)-1-(((R)-1-methyl-2-oxopiperidin-3-yl)amino)-7,9-dihydrofuro[3,4-f]quinazolin-6-y1)-5-fluorobenzo[d]thiazol-2-yl)carbamate | 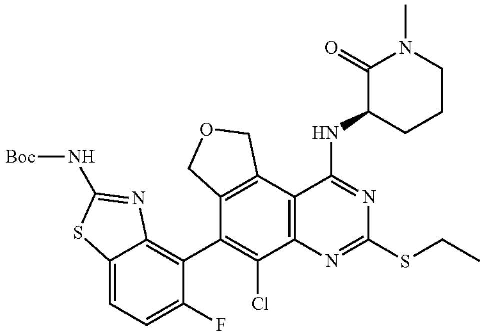 [SMILES: CCSc1nc(N[C@@H]2CCCN(C)C2=O)c2c3c(c(-c4c(F)ccc5sc(NC(=O)OC(C)(C)C)nc45)c(Cl)c2n1)COC3] | 659 |

TABLE 5-continued

| Preparation | Chemical Name | Structure | MS (ES) m/z (M + 1) |
|---|---|---|---|
| 17A | tert-butyl (4-(3-(ethylthio)-5-fluoro-1-(((R)-1-methyl-2-oxopiperidin-3-yl)amino)-7,9-dihydrofuro[3,4-f]quinazolin-6-yl)-7-methylbenzo[d]thiazol-2-yl)carbamate | 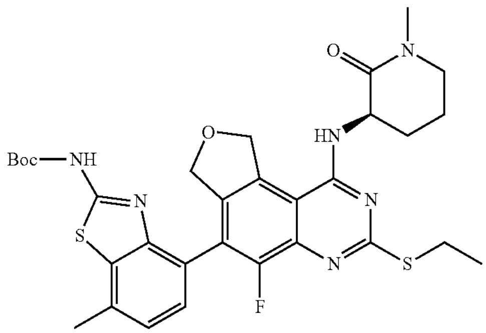 [SMILES: CCSc1nc(N[C@@H]2CCCN(C)C2=O)c2c3c(c(-c4ccc(C)c5sc(NC(=O)OC(C)(C)C)nc45)c(F)c2n1)COC3] | 639 |

Preparation 51 tert-Butyl (4-(5-chloro-3-(ethylthio)-1-(((R)-1-methyl-2-oxopiperidin-3-yl)amino)-7,9-dihydrofuro[3,4-f]quinazolin-6-yl)-7-fluorothiazolo[4,5-c]pyridin-2-yl)carbamate

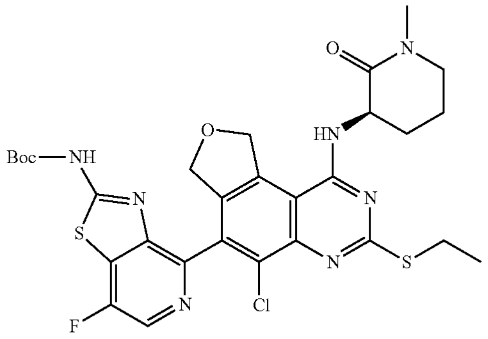 [SMILES: CCSc1nc(N[C@@H]2CCCN(C)C2=O)c2c3c(c(-c4ncc(F)c5sc(NC(=O)OC(C)(C)C)nc45)c(Cl)c2n1)COC3]

(R)-3-((5-Chloro-6-(5,5-dimethyl-1,3,2-dioxaborinan-2-yl)-3-(ethylthio)-7,9-dihydrofuro[3,4-f]quinazolin-1-yl)amino)-1-methylpiperidin-2-one. A mixture of (R)-3-((6-bromo-5-chloro-3-(ethylthio)-7,9-dihydrofuro[3,4-f]quinazolin-1-yl)amino)-1-methylpiperidin-2-one (92% purity; 14.95 g, 29.15 mmol), 5,5,5',5'-tetramethyl-2,2'-bi(1,3,2-dioxaborinane) (13.17 g, 58.30 mmol), potassium acetate (8.58 g, 87.46 mmol), and Pd-117 (CAS 205319-06-8; 1.25 g, 1.75 mmol) in 1,4-dioxane (150 mL) was degassed (direct nitrogen sparge) for 10 min. The mixture was stirred at 90° C. for 4 h, then cooled and diluted with water (250 mL) and 2-methyltetrahydrofuran (150 mL). The layers were separated. The organics were washed with brine (150 mL), dried over magnesium sulfate, filtered, and concentrated under reduced pressure. The crude material was purified on silica, eluting with 0-8% MeOH in DCM to obtain (R)-3-((5-chloro-6-(5,5-dimethyl-1,3,2-dioxaborinan-2-yl)-3-(ethylthio)-7,9-dihydrofuro[3,4-f]quinazolin-1-yl)amino)-1-methylpiperidin-2-one (86% purity; 14.2 g, 83%) as a yellow solid. MS (ES) m/z=437 (M+1, boronic acid).

tert-Butyl (4-(5-chloro-3-(ethylthio)-1-(((R)-1-methyl-2-oxopiperidin-3-yl)amino)-7,9-dihydrofuro[3,4-f]quinazolin-6-yl)-7-fluorothiazolo[4,5-c]pyridin-2-yl)carbamate. A mixture of tert-butyl (4-chloro-7-fluorothiazolo[4,5-c]pyridin-2-yl)carbamate (4.00 g, 12.9 mmol), dipotassium phosphate (6.74 g, 38.7 mmol) in water (38.7 mL), 2-dicyclohexylphosphino-2',4',6'-triisopropylbiphenyl (0.62 g, 1.29 mmol), and XPhos Pd(crotyl)Cl (CAS 1798782-02-1; 1.04 g, 1.55 mmol) in 1,4-dioxane (120 mL) was degassed (direct nitrogen sparge) for 5 min. The mixture was stirred at 85° C. and (R)-3-((5-chloro-6-(5,5-dimethyl-1,3,2-dioxaborinan-2-yl)-3-(ethylthio)-7,9-dihydrofuro[3,4-f]quinazolin-1-yl)amino)-1-methylpiperidin-2-one (81 wt %; 11.3 g, 18.1 mmol) was added in four portions, every 8 min. The mixture was stirred at 85° C. for 2.5 h, then more XPhos Pd(crotyl)Cl (CAS 1798782-02-1; 0.35 g, 0.52 mmol) was added. After 3 h, the mixture was cooled and poured into water (600 mL). The mixture was filtered and the solids were washed with water (2×50 mL) and dried under vacuum. The solids were purified on silica, eluting with 30-100% EtOAc in cyclohexane. Clean fractions were combined and partially concentrated under reduced pressure. The resulting solids were filtered to obtain the title compound (3.59 g, 42%). MS (ES) m/z=660 (M+1).

Preparation 52 tert-Butyl (4-(5-chloro-3-(ethylsulfonyl)-1-(((R)-1-methyl-2-oxopiperidin-3-yl)amino)-7,9-dihydrofuro[3,4-f]quinazolin-6-yl)-5,7-difluorobenzo[d]thiazol-2-yl)carbamate

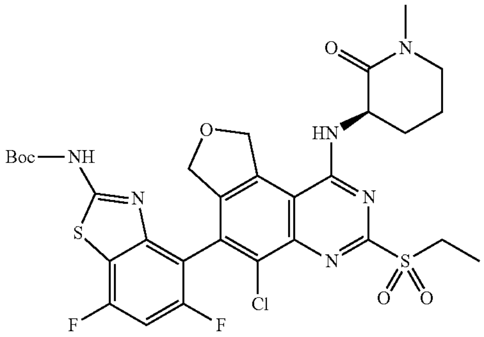 [SMILES: CCS(=O)(=O)c1nc(N[C@@H]2CCCN(C)C2=O)c2c3c(c(-c4c(F)cc(F)c5sc(NC(=O)OC(C)(C)C)nc45)c(Cl)c2n1)COC3]

To a solution of tert-butyl (4-(5-chloro-3-(ethylthio)-1-(((R)-1-methyl-2-oxopiperidin-3-yl)amino)-7,9-dihydrofuro[3,4-f]quinazolin-6-yl)-5,7-difluorobenzo[d]thiazol-2-yl)carbamate (2.3 g, 3.4 mmol) in THF (100 mL) was added mCPBA (2.07 g, 10.2 mmol) portionwise at 0° C. The mixture was stirred at room temperature under nitrogen for 2 h, then cooled to 0° C. The mixture was diluted with ice water (30 mL) and saturated aqueous sodium sulfite (200 mL), then extracted with EtOAc (300 mL). The organics were dried over anhydrous $Na_2SO_4$, filtered, and concentrated under reduced pressure to obtain the title compound (2.3 g) as a yellow solid. MS (ES) m/z=709 (M+1).

The following compounds in Table 6 were prepared in similar manner as described in Preparation 52. Various methods were used to purify the compounds, which would be apparent to one skilled in the art.

TABLE 6

| Preparation | Chemical Name | Structure | MS (ES) m/z (M + 1) |
|---|---|---|---|
| 53 | (R)-3-((6-Bromo-3-(ethylsulfonyl)-5-fluoro-7,9-dihydrofuro[3,4-f]quinazolin-1-yl)amino)-1-methylpiperidin-2-one | 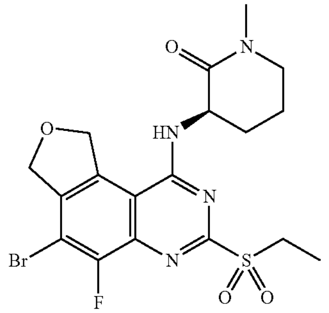 [SMILES: CCS(=O)(=O)c1nc(N[C@@H]2CCCN(C)C2=O)c2c3c(c(Br)c(F)c2n1)COC3] | 487 |
| 54 | (R)-3-((6-Bromo-5-chloro-3-(ethylsulfonyl)-7,9-dihydrofuro[3,4-f]quinazolin-1-yl)amino)-1-methylpiperidin-2-one | 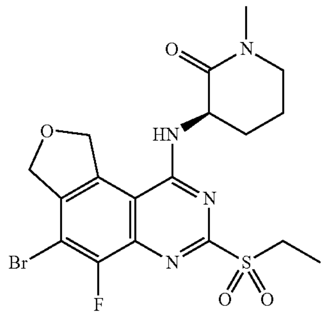 [SMILES: CCS(=O)(=O)c1nc(N[C@@H]2CCCN(C)C2=O)c2c3c(c(Br)c(F)c2n1)COC3] | 503 |
| 55 | tert-Butyl (4-(1-(((6R)-1,6-dimethyl-2-oxopiperidin-3-yl)amino)-3-(ethylsulfonyl)-5-fluoro-7,9-dihydrofuro[3,4-f]quinazolin-6-yl)-7-fluorobenzo[d]thiazol-2-yl)carbamate | 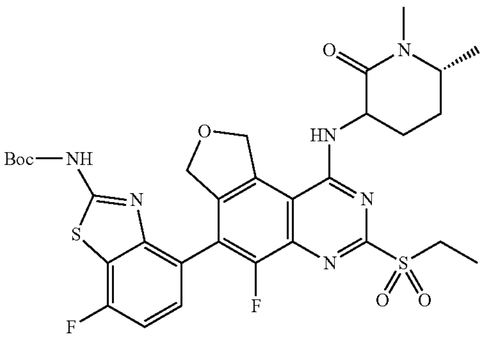 [SMILES: CCS(=O)(=O)c1nc(NC2CC[C@@H](C)N(C)C2=O)c2c3c(c(-c4ccc(F)c5sc(NC(=O)OC(C)(C)C)nc45)c(F)c2n1)COC3] | 689 |
| 56 | tert-Butyl (4-(1-(((6S)-1,6-dimethyl-2-oxopiperidin-3-yl)amino)-3-(ethylsulfonyl)-5-fluoro-7,9-dihydrofuro[3,4-f]quinazolin-6-yl)-7-fluorobenzo[d]thiazol-2-yl)carbamate | 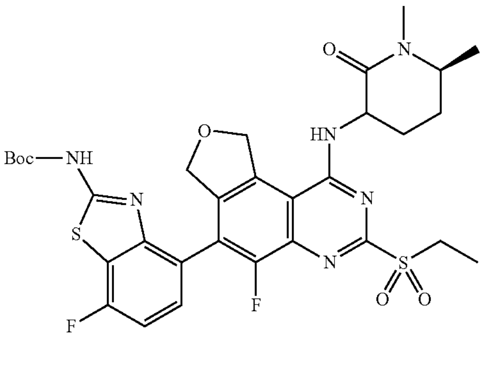 [SMILES: CCS(=O)(=O)c1nc(NC2CC[C@H](C)N(C)C2=O)c2c3c(c(-c4ccc(F)c5sc(NC(=O)OC(C)(C)C)nc45)c(F)c2n1)COC3] | 689 |

TABLE 6-continued

| Preparation | Chemical Name | Structure | MS (ES) m/z (M + 1) |
|---|---|---|---|
| 57 | tert-Butyl (4-(3-(ethylsulfonyl)-5-fluoro-1-(((R)-1-methyl-2-oxopiperidin-3-yl)amino)-7,9-dihydrofuro[3,4-f]quinazolin-6-yl)-7-fluorobenzo[d]thiazol-2-yl)carbamate | 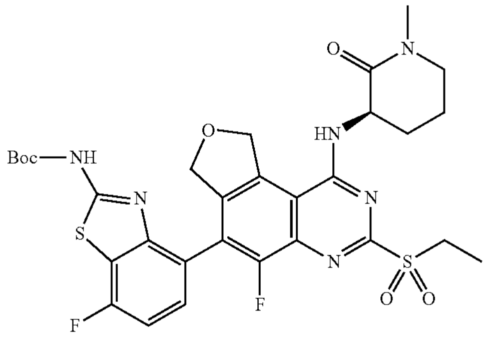 | 675 |
| 58 | tert-Butyl (4-(5-chloro-1-(((6S)-1,6-dimethyl-2-oxopiperidin-3-yl)amino)-3-(ethylsulfonyl)-7,9-dihydrofuro[3,4-f]quinazolin-6-yl)-7-fluorobenzo[d]thiazol-2-yl)carbamate | 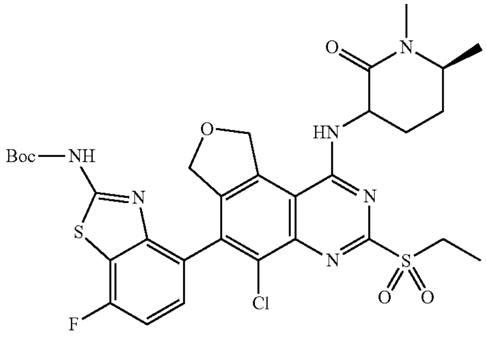 [SMILES: CCS(=O)(=O)c1nc(NC2CC[C@H](C)N(C)C2=O)c2c3c(c(-c4ccc(F)c5sc(NC(=O)OC(C)(C)C)nc45)c(Cl)c2n1)COC3] | 705 |
| 59 | tert-Butyl (4-(5-chloro-3-(ethylsulfonyl)-1-(((R)-1-methyl-2-oxopiperidin-3-yl)amino)-7,9-dihydrofuro[3,4-f]quinazolin-6-yl)-7-fluorothiazolo[4,5-c]pyridin-2-yl)carbamate | 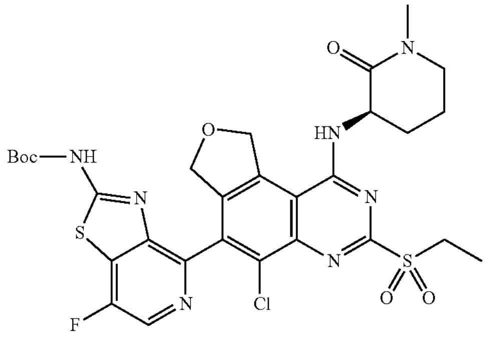 | 692 |
| 60 | tert-Butyl (4-(5-chloro-3-(ethylsulfonyl)-1-(((R)-1-methyl-2-oxopiperidin-3-yl)amino)-7,9-dihydrofuro[3,4-f]quinazolin-6-yl)-5-fluorobenzo[d]thiazol-2-yl)carbamate | 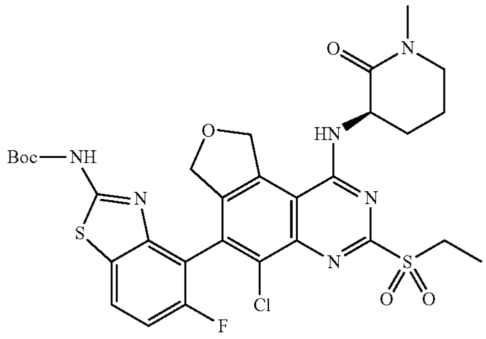 | 691 |

TABLE 6-continued

| Preparation | Chemical Name | Structure | MS (ES) m/z (M + 1) |
|---|---|---|---|
| 18A | tert-butyl (4-(5-chloro-3-(ethylsulfonyl)-1-(((R)-1-methyl-2-oxopiperidin-3-yl)amino)-7,9-dihydrofuro[3,4-f]quinazolin-6-yl)-7-fluorobenzo[d]thiazol-2-yl)carbamate | 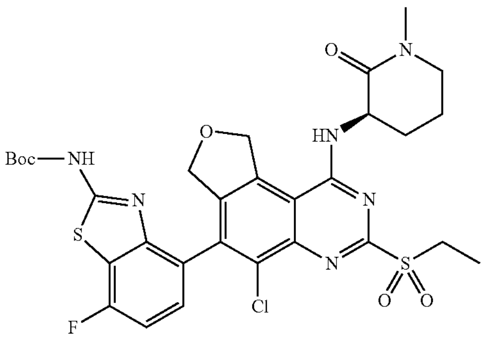 [SMILES: CCS(=O)(=O)c1nc(N[C@@H]2CCCN(C)C2=O)c2c3c(c(-c4ccc(F)c5sc(NC(=O)OC(C)(C)C)nc45)c(Cl)c2n1)COC3] | 691 |
| 19A | (6R)-3-((6-bromo-5-chloro-3-(ethylsulfonyl)-7,9-dihydrofuro[3,4-f]quinazolin-1-yl)amino)-1,6-dimethylpiperidin-2-one | 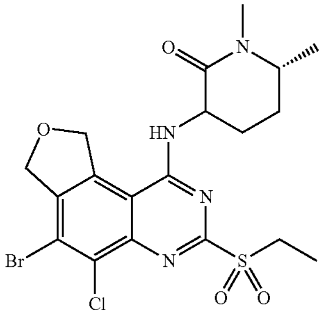 [SMILES: CCS(=O)(=O)c1nc(NC2CC[C@@H](C)N(C)C2=O)c2c3c(c(Br)c(Cl)c2n1)COC3] | 517 |
| 20A | (3R)-3-((6-(2-amino-7-methylbenzo[d]thiazol-4-yl)-3-(ethylsulfonyl)-5-fluoro-7,9-dihydrofuro[3,4-f]quinazolin-1-yl)amino)-1-methylpiperidin-2-one | 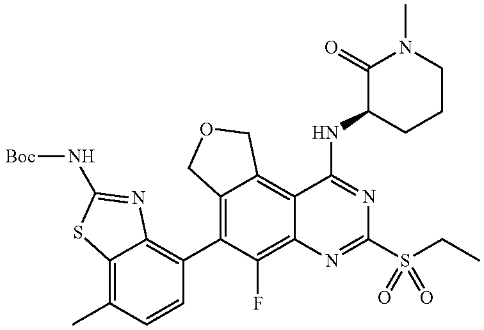 [SMILES: CCS(=O)(=O)c1nc(N[C@@H]2CCCN(C)C2=O)c2c3c(c(-c4ccc(C)c5sc(NC(=O)OC(C)(C)C)nc45)c(F)c2n1)COC3] | 671 |

Preparation 61 tert-Butyl (4-(5-chloro-3-((2S,3S)-3-(isopropyl (methyl)amino)-2-methylpyrrolidin-1-yl)-1-(((R)-1-methyl-2-oxopiperidin-3-yl)amino)-7,9-dihydrofuro [3,4-f]quinazolin-6-yl)-5,7-difluorobenzo[d]thiazol-2-yl)carbamate

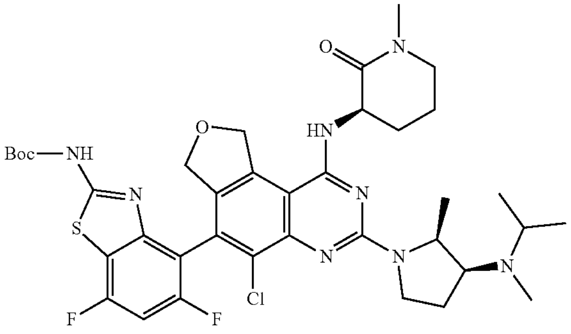 [SMILES: CC(C)N(C)[C@H]1CCN(c2nc(N[C@@H]3CCCN(C)C3=O)c3c4c(c(-c5c(F)cc(F)c6sc(NC(=O)OC(C)(C)C)nc56)c(Cl)c3n2)COC4)[C@H]1C]

To a solution of tert-butyl (4-(5-chloro-3-(ethylsulfonyl)-1-(((R)-1-methyl-2-oxopiperidin-3-yl)amino)-7,9-dihydro-furo[3,4-f]quinazolin-6-yl)-5,7-difluorobenzo[d]thiazol-2-yl)carbamate (0.400 g, 0.564 mmol) and (2S,3S)—N-isopropyl-N,2-dimethylpyrrolidin-3-amine (1.32 g, 8.46 mmol) in THF (80 mL) was added triethylamine (2.85 g, 28.2 mmol) dropwise at room temperature under nitrogen. The mixture was stirred at 80° C. for 30 h, then diluted with water (150 mL) and extracted with EtOAc (200 mL). The organics were washed with brine (150 mL), dried over anhydrous $Na_2SO_4$, filtered, and concentrated under reduced pressure. The crude material was purified on silica, eluting with 15-25% (30% MeOH in EtOAc) in DCM to obtain the title compound (0.32 g, 74%) as a yellow solid. MS (ES) m/z=771 (M+1).

The following compounds in Table 7 were prepared in similar manner as described in Preparation 61. Different bases, such as sodium hydride, may have been used. Various methods were used to purify the compounds, which would be apparent to one skilled in the art.

TABLE 7

| Preparation | Chemical Name | Structure | MS (ES) m/z (M + 1) |
|---|---|---|---|
| 62 | (R)-3-((6-Bromo-3-((2S,3S)-3-(dimethylamino)-2-methylpyrrolidin-1-yl)-5-fluoro-7,9-dihydrofuro[3,4-f]quinazolin-1-yl)amino)-1-methylpiperidin-2-one | 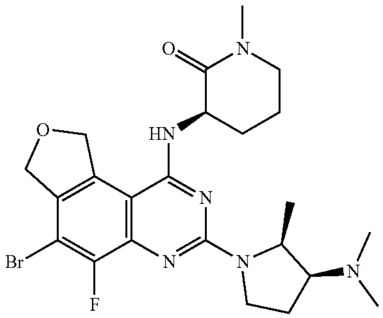 [SMILES: C[C@H]1[C@@H](N(C)C)CCN1c1nc(N[C@@H]2CCCN(C)C2=O)c2c3c(c(Br)c(F)c2n1)COC3] | 523 |
| 63 | (R)-3-((6-Bromo-3-((2S,3S)-3-(ethyl(methyl)amino)-2-methylpyrrolidin-1-yl)-5-fluoro-7,9-dihydrofuro[3,4-f]quinazolin-1-yl)amino)-1-methylpiperidin-2-one | 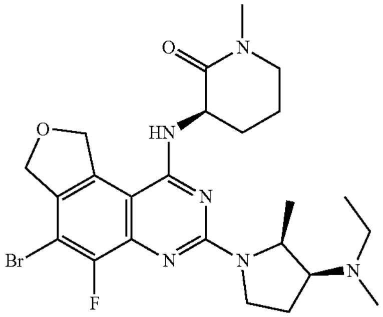 [SMILES: CCN(C)[C@H]1CCN(c2nc(N[C@@H]3CCCN(C)C3=O)c3c4c(c(Br)c(F)c3n2)COC4)[C@H]1C] | 535 |

TABLE 7-continued

| Preparation | Chemical Name | Structure | MS (ES) m/z (M + 1) |
| --- | --- | --- | --- |
| 64 | (R)-3-((6-Bromo-5-chloro-3-((2S,3S)-3-(dimethylamino)-2-methylpyrrolidin-1-yl)-7,9-dihydrofuro[3,4-f]quinazolin-1-yl)amino)-1-methylpiperidin-2-one | 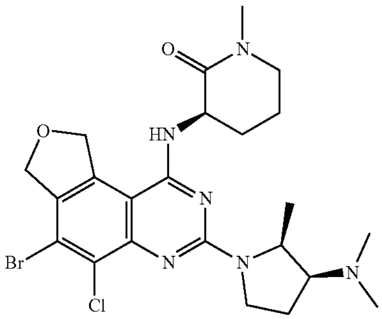 [SMILES: C[C@H]1[C@@H](N(C)C)CCN1c1nc(N[C@@H]2CCCN(C)C2=O)c2c3c(c(Br)c(Cl)c2n1)COC3] | 537 |
| 65 | tert-Butyl (4-(5-chloro-3-(((2S,4R)-4-fluoro-1-methylpyrrolidin-2-yl)methoxy)-1-(((R)-1-methyl-2-oxopiperidin-3-yl)amino)-7,9-dihydrofuro[3,4-f]quinazolin-6-yl)-5,7-difluorobenzo[d]thiazol-2-yl)carbamate | 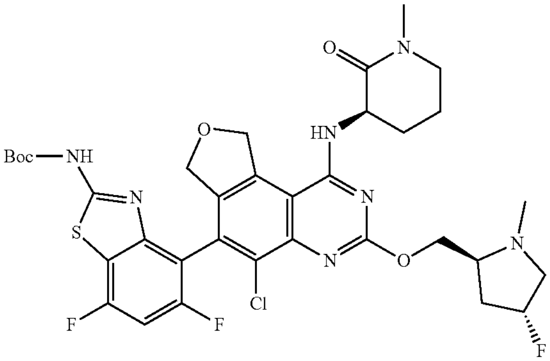 [SMILES: CN1CCC[C@@H](Nc2nc(OC[C@@H]3C[C@@H](F)CN3C)nc3c(Cl)c(-c4c(F)cc(F)c5sc(NC(=O)OC(C)(C)C)nc45)c4c(c23)COC4)C1=O] | 748 |
| 66 | tert-Butyl (4-(1-(((6R)-1,6-dimethyl-2-oxopiperidin-3-yl)amino)-3-((2S,3S)-3-(dimethylamino)-2-methylpyrrolidin-1-yl)-5-fluoro-7,9-dihydrofuro[3,4-f]quinazolin-6-yl)-7-fluorobenzo[d]thiazol-2-yl)carbamate | 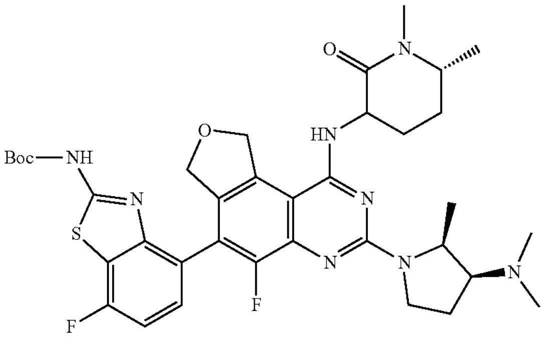 [SMILES: C[C@@H]1CCC(Nc2nc(N3CC[C@H](N(C)C)[C@@H]3C)nc3c(F)c(-c4ccc(F)c5sc(NC(=O)OC(C)(C)C)nc45)c4c(c23)COC4)C(=O)N1C] | 723 |
| 67 | tert-Butyl (4-(1-(((6S)-1,6-dimethyl-2-oxopiperidin-3-yl)amino)-3-((2S,3S)-3-(dimethylamino)-2-methylpyrrolidin-1-yl)-5-fluoro-7,9-dihydrofuro[3,4-f]quinazolin-6-yl)-7-fluorobenzo[d]thiazol-2-yl)carbamate | 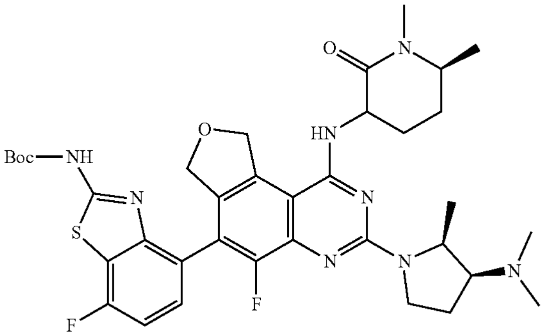 [SMILES: C[C@H]1CCC(Nc2nc(N3CC[C@H](N(C)C)[C@@H]3C)nc3c(F)c(-c4ccc(F)c5sc(NC(=O)OC(C)(C)C)nc45)c4c(c23)COC4)C(=O)N1C] | 723 |

TABLE 7-continued

| Preparation | Chemical Name | Structure | MS (ES) m/z (M + 1) |
|---|---|---|---|
| 68 | tert-Butyl (7-fluoro-4-(5-fluoro-3-(((2S,4R)-4-fluoro-1-methylpyrrolidin-2-yl)methoxy)-1-(((R)-1-methyl-2-oxopiperidin-3-yl)amino)-7,9-dihydrofuro[3,4-f]quinazolin-6-yl)benzo[d]thiazol-2-yl)carbamate | 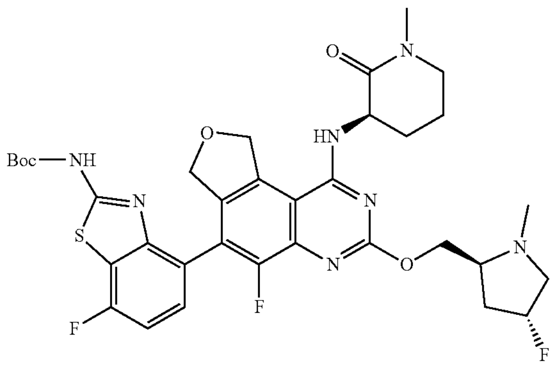 [SMILES: CN1CCC[C@@H](Nc2nc(OC[C@@H]3C[C@@H](F)CN3C)nc3c(F)c(-c4ccc(F)c5sc(NC(=O)OC(C)(C)C)nc45)c4c(c23)COC4)C1=O] | 714 |
| 69 | tert-Butyl (7-fluoro-4-(5-fluoro-3-(((2R,4R)-4-fluoro-1-methylpyrrolidin-2-yl)methoxy)-1-(((R)-1-methyl-2-oxopiperidin-3-yl)amino)-7,9-dihydrofuro[3,4-f]quinazolin-6-yl)benzo[d]thiazol-2-yl)carbamate | 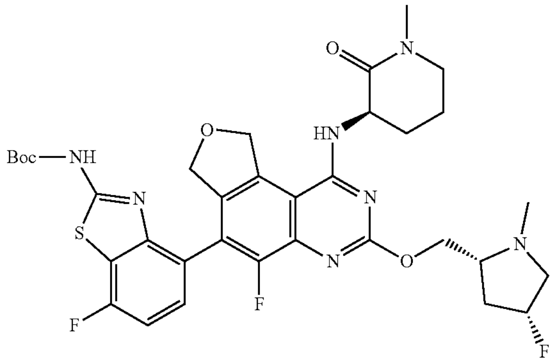 [SMILES: CN1CCC[C@@H](Nc2nc(OC[C@H]3C[C@@H](F)CN3C)nc3c(F)c(-c4ccc(F)c5sc(NC(=O)OC(C)(C)C)nc45)c4c(c23)COC4)C1=O] | 714 |
| 70 | tert-Butyl (4-(3-((2S,3S)-3-(diethylamino)-2-methylpyrrolidin-1-yl)-5-fluoro-1-(((R)-1-methyl-2-oxopiperidin-3-yl)amino)-7,9-dihydrofuro[3,4-f]quinazolin-6-yl)-7-fluorobenzo[d]thiazol-2-yl)carbamate | 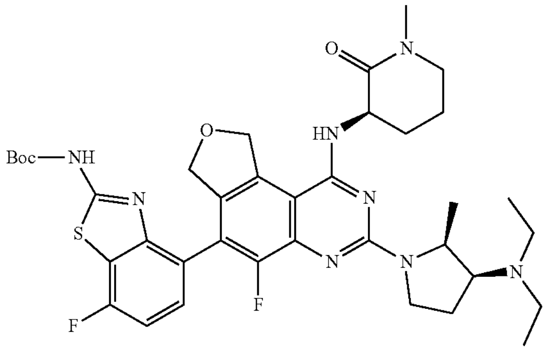 [SMILES: CCN(CC)[C@H]1CCN(c2nc(N[C@@H]3CCCN(C)C3=O)c3c4c(c(-c5ccc(F)c6sc(NC(=O)OC(C)(C)C)nc56)c(F)c3n2)COC4)[C@H]1C] | 737 |
| 71 | (R)-3-((6-Bromo-5-chloro-3-((2S,3S)-3-(isopropylamino)-2-methylpyrrolidin-1-yl)-7,9-dihydrofuro[3,4-f]quinazolin-1-yl)amino)-1-methylpiperidin-2-one | 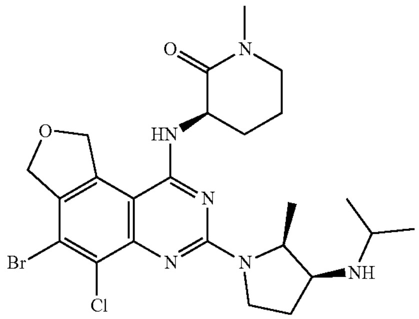 [SMILES: CC(C)N[C@H]1CCN(c2nc(N[C@@H]3CCCN(C)C3=O)c3c4c(c(Br)c(Cl)c3n2)COC4)[C@H]1C] | 551 |

TABLE 7-continued

| Preparation | Chemical Name | Structure | MS (ES) m/z (M + 1) |
| --- | --- | --- | --- |
| 72 | tert-Butyl (4-(5-chloro-1-(((6S)-1,6-dimethyl-2-oxopiperidin-3-yl)amino)-3-((S)-3-(dimethylamino)pyrrolidin-1-yl)-7,9-dihydrofuro[3,4-f]quinazolin-6-yl)-7-fluorobenzo[d]thiazol-2-yl)carbamate | 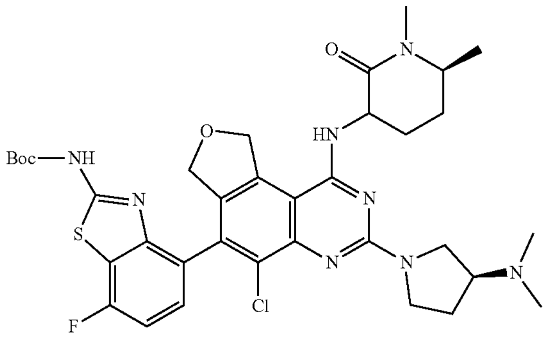 [SMILES: C[C@H]1CCC(Nc2nc(N3CC[C@H](N(C)C)C3)nc3c(Cl)c(-c4ccc(F)c5sc(NC(=O)OC(C)(C)C)nc45)c4c(c23)COC4)C(=O)N1C] | 725 |
| 73 | tert-Butyl (4-(5-chloro-3-((2S,3S)-3-(ethyl(methyl)amino)-2-methylpyrrolidin-1-yl)-1-(((R)-1-methyl-2-oxopiperidin-3-yl)amino)-7,9-dihydrofuro[3,4-f]quinazolin-6-yl)-7-fluorothiazolo[4,5-c]pyridin-2-yl)carbamate | 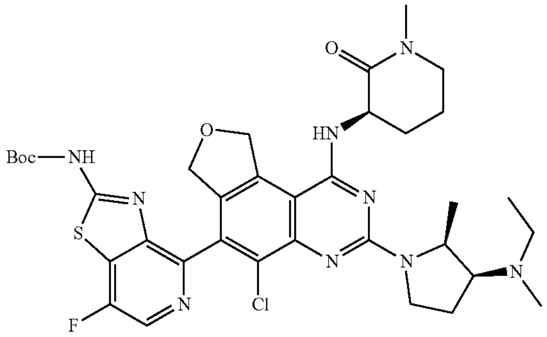 [SMILES: CCN(C)[C@H]1CCN(c2nc(N[C@@H]3CCCN(C)C3=O)c3c4c(c(-c5ncc(F)c6sc(NC(=O)OC(C)(C)C)nc56)c(Cl)c3n2)COC4)[C@H]1C] | 740 |
| 74 | tert-Butyl (4-(5-chloro-3-((2S,3S)-3-(isopropyl(methyl)amino)-2-methylpyrrolidin-1-yl)-1-(((R)-1-methyl-2-oxopiperidin-3-yl)amino)-7,9-dihydrofuro[3,4-f]quinazolin-6-yl)-7-fluorothiazolo[4,5-c]pyridin-2-yl)carbamate | 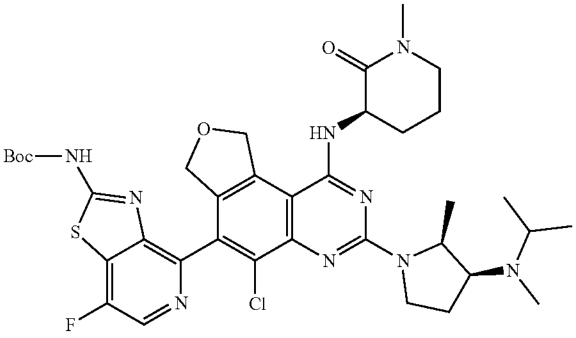 [SMILES: CC(C)N(C)[C@H]1CCN(c2nc(N[C@@H]3CCCN(C)C3=O)c3c4c(c(-c5ncc(F)c6sc(NC(=O)OC(C)(C)C)nc56)c(Cl)c3n2)COC4)[C@H]1C] | 754 |
| 75 | tert-Butyl (4-(5-chloro-3-((2S,3S)-3-(dimethylamino)-2-methylpyrrolidin-1-yl)-1-(((R)-1-methyl-2-oxopiperidin-3-yl)amino)-7,9-dihydrofuro[3,4-f]quinazolin-6-yl)-5-fluorobenzo[d]thiazol-2-yl)carbamate | 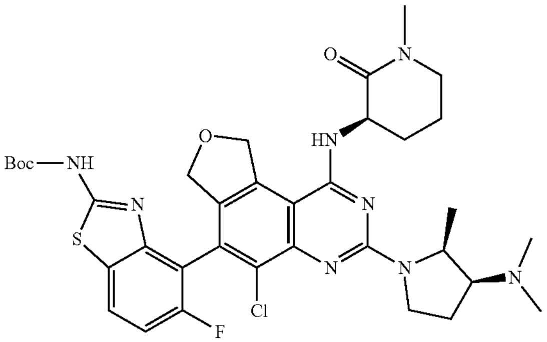 [SMILES: C[C@H]1[C@@H](N(C)C)CCN1c1nc(N[C@@H]2CCCN(C)C2=O)c2c3c(c(-c4c(F)ccc5sc(NC(=O)OC(C)(C)C)nc45)c(Cl)c2n1)COC3] | 725 |

TABLE 7-continued

| Preparation | Chemical Name | Structure | MS (ES) m/z (M + 1) |
|---|---|---|---|
| 21A | tert-butyl (4-(5-chloro-3-(((2S,4R)-4-methoxy-1-methylpyrrolidin-2-yl)methoxy)-1-(((R)-1-methyl-2-oxopiperidin-3-yl)amino)-7,9- dihydrofuro[3,4-f]quinazolin-6-y1)-5,7-difluorobenzo[d]thiazol-2-yl)carbamate | 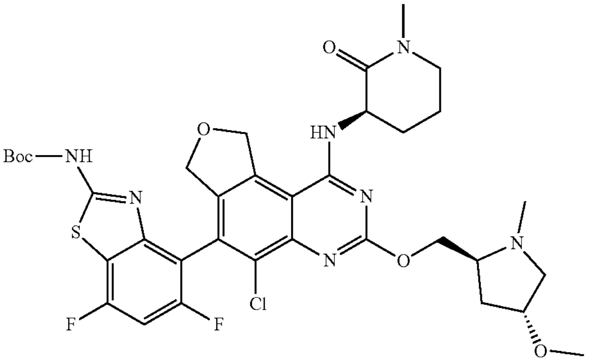 [SMILES: CO[C@@H]1C[C@@H](COc2nc(N[C@@H]3CCCN(C)C3=O)c3c4c(c(-c5c(F)cc(F)c6sc(NC(=O)OC(C)(C)C)nc56)c(Cl)c3n2)COC4)N(C)C1] | 760 |
| 22A | tert-butyl (4-(5-chloro-3-((S)-3-(diethylamino)pyrrolidin-1-y1)-1-(((R)-1-methyl-2-oxopiperidin-3-yl)amino)-7,9-dihydrofuro[3,4-f]quinazolin-6-yl)-5,7-difluorobenzo[d]thiazol-2-yl)carbamate | 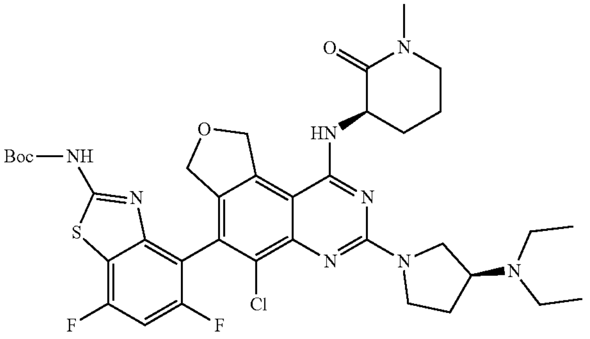 [SMILES: CCN(CC)[C@H]1CCN(c2nc(N[C@@H]3CCCN(C)C3=O)c3c4c(c(-c5c(F)cc(F)c6sc(NC(=O)OC(C)(C)C)nc56)c(Cl)c3n2)COC4)C1] | 757 |
| 23A | tert-butyl (7-fluoro-4-(5-fluoro-3-((2S,3S)-3-(isopropyl(methyl)amino)-2-methylpyrrolidin-1-y1)-1-(((R)-1-methyl-2-oxopiperidin-3-yl)amino)-7,9-dihydrofuro[3,4-f]quinazolin-6-yl)benzo[d]thiazol-2-yl)carbamate | 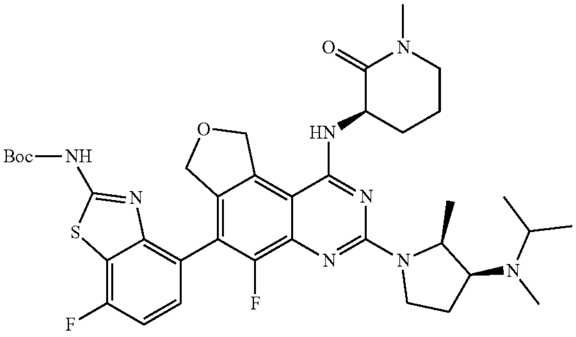 [SMILES: CC(C)N(C)[C@H]1CCN(c2nc(N[C@@H]3CCCN(C)C3=O)c3c4c(c(-c5ccc(F)c6sc(NC(=O)OC(C)(C)C)nc56)c(F)c3n2)COC4)[C@H]1C] | 737 |
| 24A | tert-butyl (7-fluoro-4-(5-fluoro-3-((3R,4S)-3-(isopropyl(methyl)amino)-4-methylpyrrolidin-1-yl)-1-(((R)-1-methyl-2-oxopiperidin-3-yl)amino)-7,9-dihydrofuro[3,4-f]quinazolin-6-yl)benzo[d]thiazol-2-yl)carbamate | 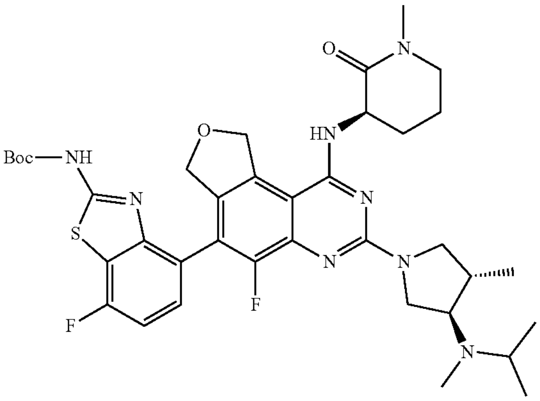 [SMILES: CC(C)N(C)[C@H]1CN(c2nc(N[C@@H]3CCCN(C)C3=O)c3c4c(c(-c5ccc(F)c6sc(NC(=O)OC(C)(C)C)nc56)c(F)c3n2)COC4)C[C@@H]1C] | 737 |

TABLE 7-continued

| Preparation | Chemical Name | Structure | MS (ES) m/z (M + 1) |
|---|---|---|---|
| 25A | tert-butyl (4-(3-(3-(ethyl(methyl)amino)-3-methylpyrrolidin-1-yl)-5-fluoro-1-(((R)-1-methyl-2-oxopiperidin-3-yl)amino)-7,9-dihydrofuro[3,4-f]quinazolin-6-yl)-7-fluorobenzo[d]thiazol-2-yl)carbamate | 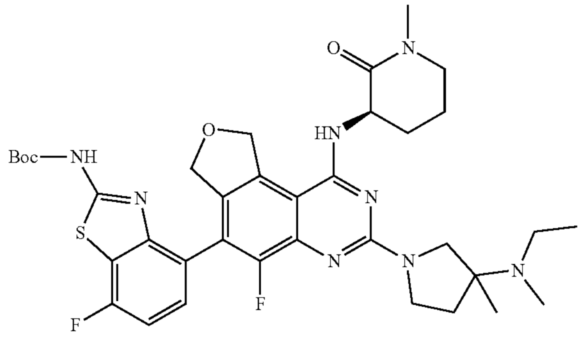 [SMILES: CCN(C)C1(C)CCN(c2nc(N[C@@H]3CCCN(C)C3=O)c3c4c(c(-c5ccc(F)c6sc(NC(=O)OC(C)(C)C)nc56)c(F)c3n2)COC4)C1] | 723 |
| 26A | tert-butyl (7-fluoro-4-(5-fluoro-3-(((2R,4S)-4-fluoro-1-methylpyrrolidin-2-yl)methoxy)-1-(((R)-1-methyl-2-oxopiperidin-3-yl)amino)-7,9-dihydrofuro[3,4-f]quinazolin-6-yl)benzo[d]thiazol-2-yl)carbamate | 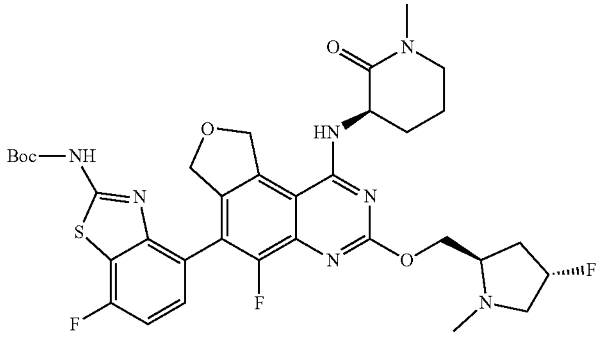 [SMILES: CN1CCC[C@@H](Nc2nc(OC[C@H]3C[C@H](F)CN3C)nc3c(F)c(-c4ccc(F)c5sc(NC(=O)OC(C)(C)C)nc45)c4c(c23)COC4)C1=O] | 714 |
| 27A | tert-butyl (7-fluoro-4-(5-fluoro-1-(((R)-1-methyl-2-oxopiperidin-3-yl)amino)-3-((2'S,3'S)-2'-methyl-[1,3'-bipyrrolidin]-1'-yl)-7,9-dihydrofuro[3,4-f]quinazolin-6-yl)benzo[d]thiazol-2-yl)carbamate | 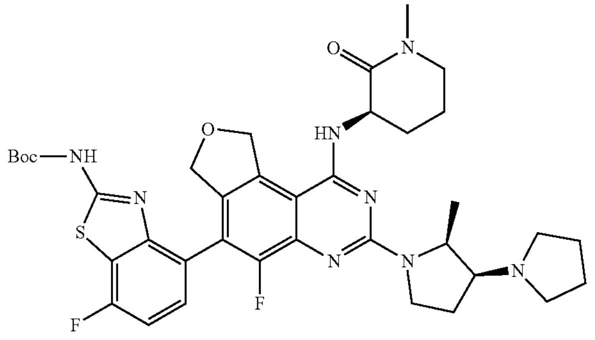 [SMILES: C[C@H]1[C@@H](N2CCCC2)CCN1c1nc(N[C@@H]2CCCN(C)C2=O)c2c3c(c(-c4ccc(F)c5sc(NC(=O)OC(C)(C)C)nc45)c(F)c2n1)COC3] | 735 |
| 28A | tert-butyl (4-(3-((2S,3S)-3-(azetidin-1-yl)-2-methylpyrrolidin-1-yl)-5-fluoro-1-(((R)-1-methyl-2-oxopiperidin-3-yl)amino)-7,9-dihydrofuro[3,4-f]quinazolin-6-yl)-7-fluorobenzo[d]thiazol-2-yl)carbamate | 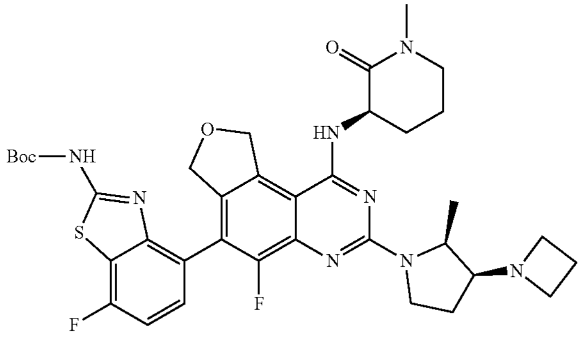 [SMILES: C[C@H]1[C@@H](N2CCC2)CCN1c1nc(N[C@@H]2CCCN(C)C2=O)c2c3c(c(-c4ccc(F)c5sc(NC(=O)OC(C)(C)C)nc45)c(F)c2n1)COC3] | 721 |

TABLE 7-continued

| Preparation | Chemical Name | Structure | MS (ES) m/z (M + 1) |
|---|---|---|---|
| 29A | tert-butyl (4-(5-chloro-3-((S)-3-(dimethylamino)pyrrolidin-1-yl)-1-(((R)-1-methyl-2-oxopiperidin-3-yl)amino)-7,9-dihydrofuro[3,4-f]quinazolin-6-yl)-7-fluorobenzo[d]thiazol-2-yl)carbamate | 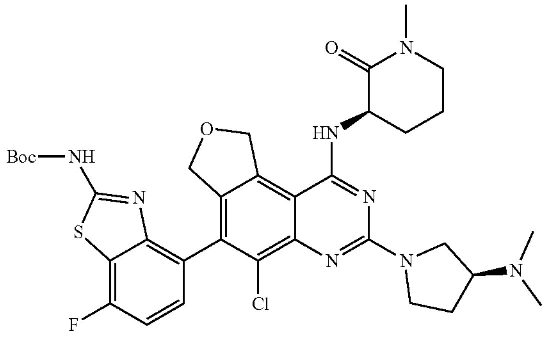 [SMILES: CN1CCC[C@@H](Nc2nc(N3CC[C@H](N(C)C)C3)nc3c(Cl)c(-c4ccc(F)c5sc(NC(=O)OC(C)(C)C)nc45)c4c(c23)COC4)C1=O] | 711 |
| 30A [1] | (6R)-3-((6-bromo-5-chloro-3-((2S,3S)-3-(dimethylamino)-2-methylpyrrolidin-1-yl)-7,9-dihydrofuro[3,4-f]quinazolin-1-yl)amino)-1,6-dimethylpiperidin-2-one, Isomer 1 | 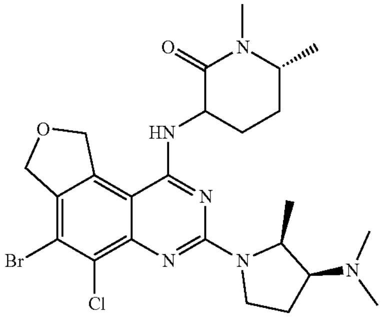 [SMILES: C[C@@H]1CCC(Nc2nc(N3CC[C@H](N(C)C)[C@@H]3C)nc3c(Cl)c(Br)c4c(c23)COC4)C(=O)N1C] | 551 |
| 31A [1] | (6R)-3-((6-bromo-5-chloro-3-((2S,3S)-3-(dimethylamino)-2-methylpyrrolidin-1-yl)-7,9-dihydrofuro[3,4-f]quinazolin-1-yl)amino)-1,6-dimethylpiperidin-2-one, Isomer 2 | 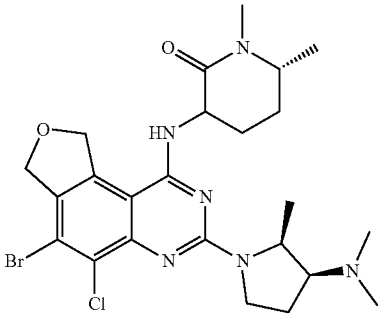 [SMILES: C[C@@H]1CCC(Nc2nc(N3CC[C@H](N(C)C)[C@@H]3C)nc3c(Cl)c(Br)c4c(c23)COC4)C(=O)N1C] | 551 |
| 32A | (R)-3-((6-bromo-5-chloro-3-((2S,3S)-3-((2-methoxyethyl)(methyl)amino)-2-methylpyrrolidin-1-yl)-7,9-dihydrofuro[3,4-f]quinazolin-1-yl)amino)-1-methylpiperidin-2-one | 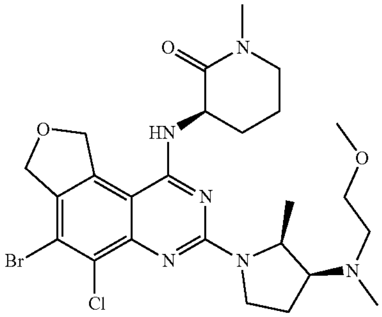 [SMILES: COCCN(C)[C@H]1CCN(c2nc(N[C@@H]3CCCN(C)C3=O)c3c4c(c(Br)c(Cl)c3n2)COC4)[C@H]1C] | 581 |

TABLE 7-continued

| Preparation | Chemical Name | Structure | MS (ES) m/z (M + 1) |
| --- | --- | --- | --- |
| 33A | tert-butyl (4-(5-chloro-3-(((2S,4R)-4-fluoro-1-methylpyrrolidin-2-yl)methoxy)-1-(((R)-1- methyl-2-oxopiperidin-3-yl)amino)-7,9- dihydrofuro[3,4-f]quinazolin-6-yl)-5-fluorobenzo[d]thiazol-2-yl)carbamate | 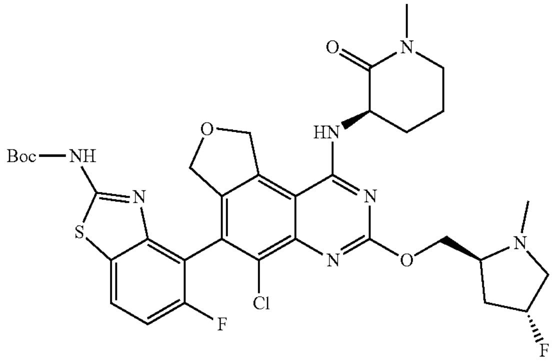 [SMILES: CN1CCC[C@@H](Nc2nc(OC[C@@H]3C[C@@H](F)CN3C)nc3c(Cl)c(-c4c(F)ccc5sc(NC(=O)OC(C)(C)C)nc45)c4c(c23)COC4)C1=O] | 730 |
| 34A | tert-butyl (4-(5-chloro-3-((2S,3S)-3-(isopropyl(methyl)amino)-2-methylpyrrolidin-1-yl)-1-(((R)-1-methyl-2-oxopiperidin-3-yl)amino)-7,9-dihydrofuro[3,4-f]quinazolin-6-yl)-5-fluorobenzo[d]thiazol-2-yl)carbamate | 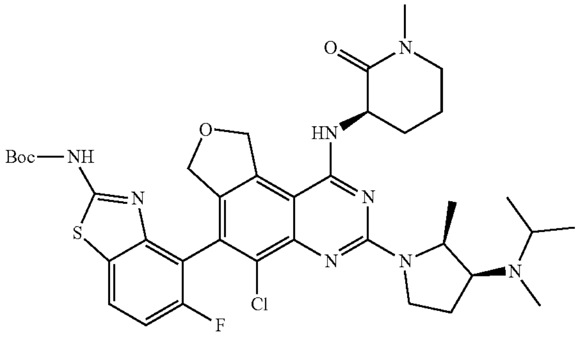 [SMILES: CC(C)N(C)[C@H]1CCN(c2nc(N[C@@H]3CCCN(C)C3=O)c3c4c(c(-c5c(F)ccc6sc(NC(=O)OC(C)(C)C)nc56)c(Cl)c3n2)COC4)[C@H]1C] | 753 |
| 35A | tert-butyl (4-(3-((2S,3S)-3-(azetidin-1-yl)-2-methylpyrrolidin-1-yl)-5-chloro-1-(((R)-1-methyl-2-oxopiperidin-3-yl)amino)-7,9-dihydrofuro[3,4-f]quinazolin-6-yl)-5-fluorobenzo[d]thiazol-2-yl)carbamate | 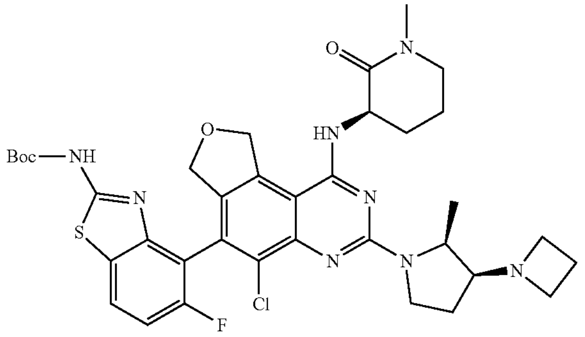 [SMILES: C[C@H]1[C@@H](N2CCC2)CCN1c1nc(N[C@@H]2CCCN(C)C2=O)c2c3c(c(-c4c(F)ccc5sc(NC(=O)OC(C)(C)C)nc45)c(Cl)c2n1)COC3] | 737 |
| 36A | tert-butyl (4-(5-chloro-3-((2S,3S)-3-(ethyl(methyl)amino)-2-methylpyrrolidin-1-yl)-1-(((R)-1-methyl-2-oxopiperidin-3-yl)amino)-7,9-dihydrofuro[3,4-f]quinazolin-6-yl)-5-fluorobenzo[d]thiazol-2-yl)carbamate | 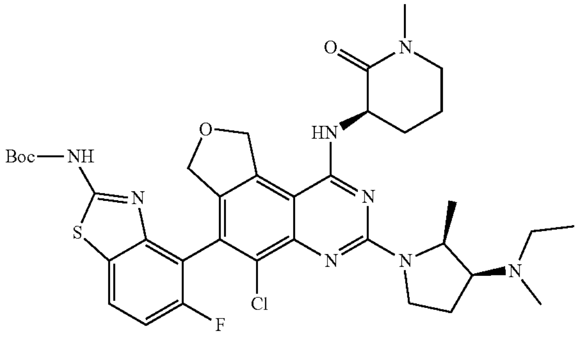 [SMILES: CCN(C)[C@H]1CCN(c2nc(N[C@@H]3CCCN(C)C3=O)c3c4c(c(-c5c(F)ccc6sc(NC(=O)OC(C)(C)C)nc56)c(Cl)c3n2)COC4)[C@H]1C] | 739 |

TABLE 7-continued

| Preparation | Chemical Name | Structure | MS (ES) m/z (M + 1) |
|---|---|---|---|
| 37A | tert-butyl (4-(3-((2S,3S)-3-(dimethylamino)-2-methylpyrrolidin-1-yl)-5-fluoro-1-(((R)-1-methyl-2-oxopiperidin-3-yl)amino)-7,9-dihydrofuro[3,4-f]quinazolin-6-yl)-7-methylbenzo[d]thiazol-2-yl)carbamate | 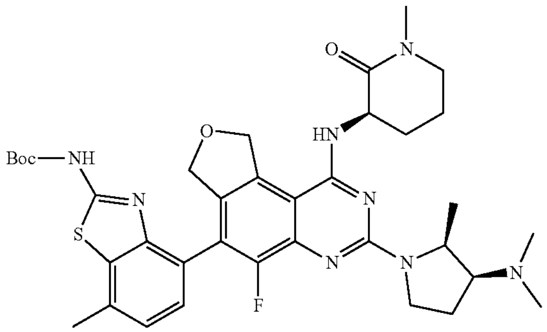 [SMILES: Cc1ccc(-c2c3c(c4c(N[C@@H]5CCCN(C)C5=O)nc(N5CC[C@H](N(C)C)[C@@H]5C)nc4c2F)COC3)c2nc(NC(=O)OC(C)(C)C)sc12] | 705 |
| 38A | (R)-3-((6-bromo-5-chloro-3-((2S,3S)-3-(isopropylamino)-2-methylpyrrolidin-1-yl)-7,9-dihydrofuro[3,4-f]quinazolin-1-yl)amino)-1-methylpiperidin-2-one | 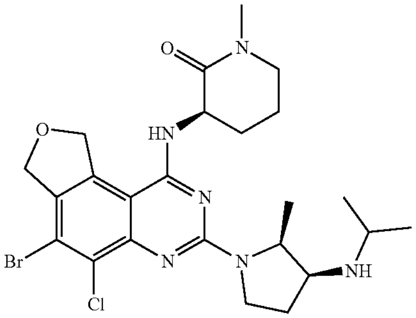 [SMILES: CC(C)N[C@H]1CCN(c2nc(N[C@@H]3CCCN(C)C3=O)c3c4c(c(Br)c(Cl)c3n2)COC4)[C@H]1C] | 521 |

[1] Prep-Chiral-HPLC; Phenomenex Lux Cellulose-4, 30 x 150 mm, 10-100% ethanol in heptane, 42.5 mL/min The following compounds in Table 8 were prepared in similar manner as described in Preparations 24 or 46. Different coupling conditions, such as base, ligands or palladium sources may have been substituted. Various methods were used to purify the compounds, which would be apparent to one skilled in the art.

TABLE 8

| Preparation | Chemical Name | Structure | MS (ES) m/z (M + 1) |
|---|---|---|---|
| 76 | tert-Butyl (4-(3-((2S,3S)-3-(dimethylamino)-2-methylpyrrolidin-1-yl)-5-fluoro-1-(((R)-1-methyl-2-oxopiperidin-3-yl)amino)-7,9-dihydrofuro[3,4-f]quinazolin-6-yl)-5,7-difluorobenzo[d]thiazol-2-yl)carbamate | 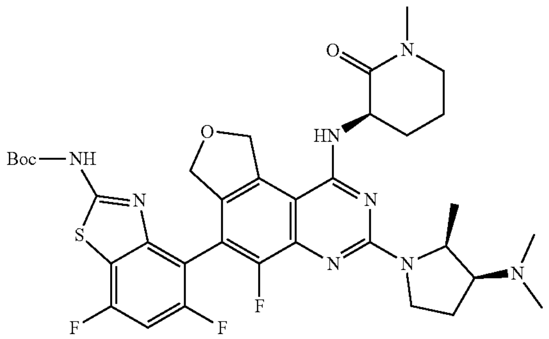 [SMILES: C[C@H]1[C@@H](N(C)C)CCN1c1nc(N[C@@H]2CCCN(C)C2=O)c2c3c(c(-c4c(F)cc(F)c5sc(NC(=O)OC(C)(C)C)nc45)c(F)c2n1)COC3] | 727 |

TABLE 8-continued

| Preparation | Chemical Name | Structure | MS (ES) m/z (M + 1) |
|---|---|---|---|
| 77 | tert-Butyl (4-(3-((2S,3S)-3-(ethyl(methyl)amino)-2-methylpyrrolidin-1-yl)-5-fluoro-1-(((R)-1-methyl-2-oxopiperidin-3-yl)amino)-7,9-dihydrofuro[3,4-f]quinazolin-6-yl)-5,7-difluorobenzo[d]thiazol-2-yl)carbamate | 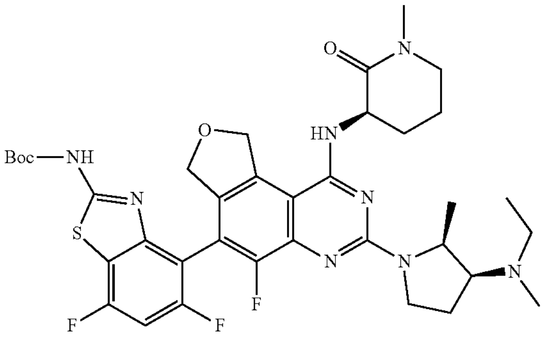 [SMILES: CCN(C)[C@H]1CCN(c2nc(N[C@@H]3CCCN(C)C3=O)c3c4c(c(-c5c(F)cc(F)c6sc(NC(=O)OC(C)(C)C)nc56)c(F)c3n2)COC4)[C@H]1C] | 741 |
| 78 | tert-Butyl (4-(5-chloro-3-((2S,3S)-3-(dimethylamino)-2-methylpyrrolidin-1-yl)-1-(((R)-1-methyl-2-oxopiperidin-3-yl)amino)-7,9-dihydrofuro[3,4-f]quinazolin-6-yl)-5,7-difluorobenzo[d]thiazol-2-yl)carbamate | 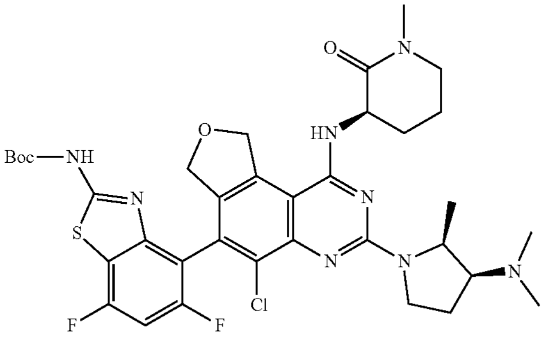 | 743 |
| 79 | tert-Butyl (4-(3-((2S,3S)-3-(dimethylamino)-2-methylpyrrolidin-1-yl)-5-fluoro-1-(((R)-1-methyl-2-oxopiperidin-3-yl)amino)-7,9-dihydrofuro[3,4-f]quinazolin-6-yl)-7-fluorobenzo[d]thiazol-2-yl)carbamate | 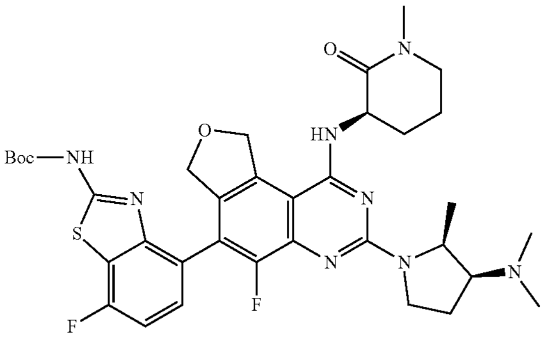 | 709 |
| 80 | tert-Butyl (4-(3-((2S,3S)-3-(ethyl(methyl)amino)-2-methylpyrrolidin-1-yl)-5-fluoro-1-(((R)-1-methyl-2-oxopiperidin-3-yl)amino)-7,9-dihydrofuro[3,4-f]quinazolin-6-yl)-7-fluorobenzo[d]thiazol-2-yl)carbamate | 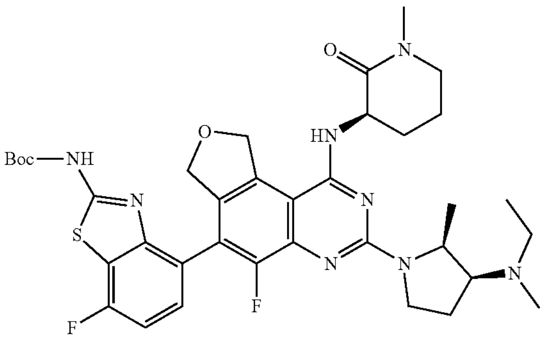 [SMILES: CCN(C)[C@H]1CCN(c2nc(N[C@@H]3CCCN(C)C3=O)c3c4c(c(-c5ccc(F)c6sc(NC(=O)OC(C)(C)C)nc56)c(F)c3n2)COC4)[C@H]1C] | 723 |

TABLE 8-continued

| Preparation | Chemical Name | Structure | MS (ES) m/z (M + 1) |
|---|---|---|---|
| 81 | tert-Butyl (4-(5-chloro-3-((2S,3S)-3-(dimethylamino)-2-methylpyrrolidin-1-yl)-1-(((R)-1-methyl-2-oxopiperidin-3-yl)amino)-7,9-dihydrofuro[3,4-f]quinazolin-6-yl)-7-fluorobenzo[d]thiazol-2-yl)carbamate | 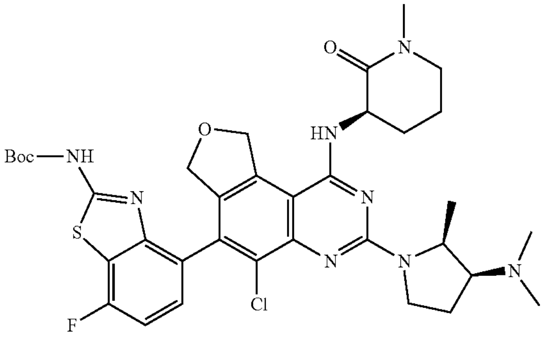 | 725 |
| 82 | tert-Butyl (4-(5-chloro-3-((2S,3S)-3-(isopropylamino)-2-methylpyrrolidin-1-yl)-1-(((R)-1-methyl-2-oxopiperidin-3-yl)amino)-7,9-dihydrofuro[3,4-f]quinazolin-6-yl)-7-fluorobenzo[d]thiazol-2-yl)carbamate | 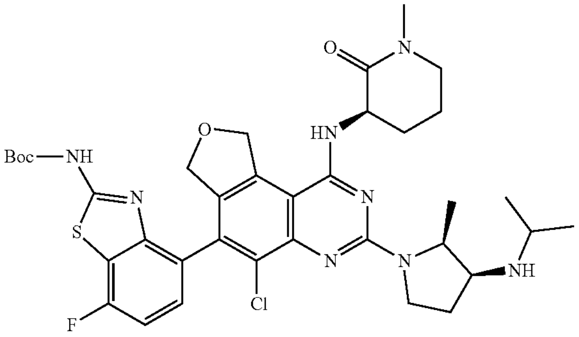 [SMILES: CC(C)N[C@H]1CCN(c2nc(N[C@@H]3CCCN(C)C3=O)c3c4c(c(-c5ccc(F)c6sc(NC(=O)OC(C)(C)C)nc56)c(Cl)c3n2)COC4)[C@H]1C] | 739 |
| 39A | tert-butyl (4-(3-((2S,3S)-3-(dimethylamino)-2-methylpyrrolidin-1-yl)-5-fluoro-1-(((R)-1-methyl-2-oxopiperidin-3-yl)amino)-7,9-dihydrofuro[3,4-f]quinazolin-6-yl)benzo[d]thiazol-2-yl)carbamate | 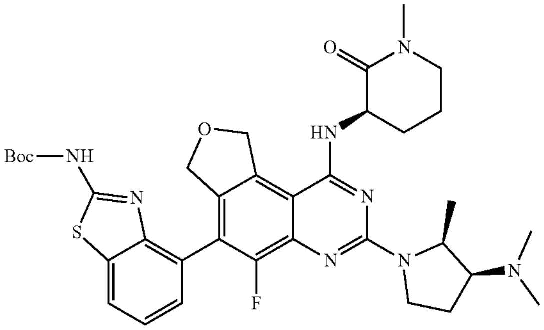 [SMILES: C[C@H]1[C@@H](N(C)C)CCN1c1nc(N[C@@H]2CCCN(C)C2=O)c2c3c(c(-c4cccc5sc(NC(=O)OC(C)(C)C)nc45)c(F)c2n1)COC3] | 691 |
| 40A | tert-butyl (4-(5-chloro-3-((2S,3S)-3-(isopropylamino)-2-methylpyrrolidin-1-yl)-1-(((R)-1-methyl-2-oxopiperidin-3-yl)amino)-7,9-dihydrofuro[3,4-f]quinazolin-6-yl)benzo[d]thiazol-2-yl)carbamate | 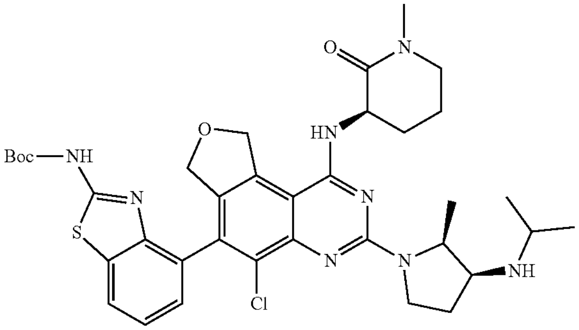 [SMILES: CC(C)N[C@H]1CCN(c2nc(N[C@@H]3CCCN(C)C3=O)c3c4c(c(-c5cccc6sc(NC(=O)OC(C)(C)C)nc56)c(Cl)c3n2)COC4)[C@H]1C] | 721 |

The following compounds in Table 9 were prepared in similar manner as described in Preparation 51. Different coupling conditions, such as base, ligands or palladium sources may have been substituted. Various methods were used to purify the compounds, which would be apparent to one skilled in the art.

TABLE 9

| Preparation | Chemical Name | Structure | MS (ES) m/z (M + 1) |
|---|---|---|---|
| 83 | tert-Butyl (4-(5-chloro-3-((2S,3S)-3-(dimethylamino)-2-methylpyrrolidin-1-yl)-1-(((R)-1-methyl-2-oxopiperidin-3-yl)amino)-7,9-dihydrofuro[3,4-f]quinazolin-6-yl)-7-fluorothiazolo[4,5-c]pyridin-2-yl)carbamate | 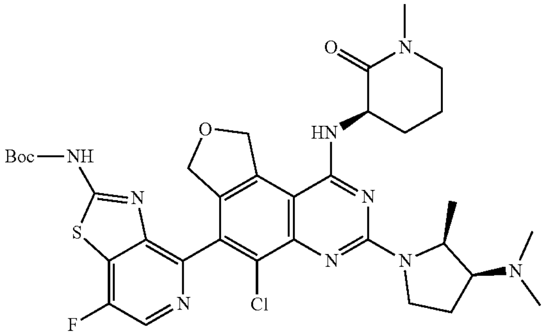 [SMILES: C[C@H]1[C@@H](N(C)C)CCN1c1nc(N[C@@H]2CCCN(C)C2=O)c2c3c(c(-c4ncc(F)c5sc(NC(=O)OC(C)(C)C)nc45)c(Cl)c2n1)COC3] | 726 |
| 84 | tert-Butyl (7-chloro-4-(3-((2S,3S)-3-(dimethylamino)-2-methylpyrrolidin-1-yl)-5-fluoro-1-(((R)-1-methyl-2-oxopiperidin-3-yl)amino)-7,9-dihydrofuro[3,4-f]quinazolin-6-yl)benzo[d]thiazol-2-yl)carbamate | 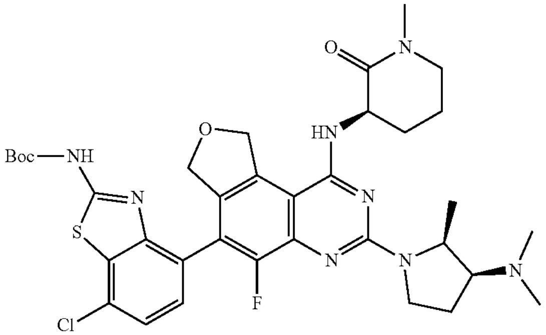 [SMILES: C[C@H]1[C@@H](N(C)C)CCN1c1nc(N[C@@H]2CCCN(C)C2=O)c2c3c(c(-c4ccc(Cl)c5sc(NC(=O)OC(C)(C)C)nc45)c(F)c2n1)COC3] | 725 |
| 41A[1] | tert-butyl (4-(5-chloro-1-(((6R)-1,6-dimethyl-2-oxopiperidin-3-yl)amino)-3-((2S,3S)-3-(dimethylamino)-2-methylpyrrolidin-1-yl)-7,9-dihydrofuro[3,4-f]quinazolin-6-yl)-7-fluorothiazolo[4,5-c]pyridin-2-yl)carbamate | 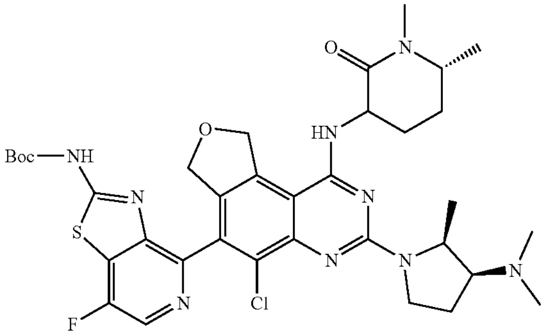 [SMILES: C[C@@H]1CCC(Nc2nc(N3CC[C@H](N(C)C)[C@@H]3C)nc3c(Cl)c(-c4ncc(F)c5sc(NC(=O)OC(C)(C)C)nc45)c4c(c23)COC4)C(=O)N1C] | 740 |
| 42A | tert-butyl (4-(5-chloro-3-((2S,3S)-3-((2-methoxyethyl)(methyl)amino)-2-methylpyrrolidin-1-yl)-1-(((R)-1-methyl-2-oxopiperidin-3-yl)amino)-7,9-dihydrofuro[3,4-f]quinazolin-6-yl)-7-fluorothiazolo[4,5-c]pyridin-2-yl)carbamate | 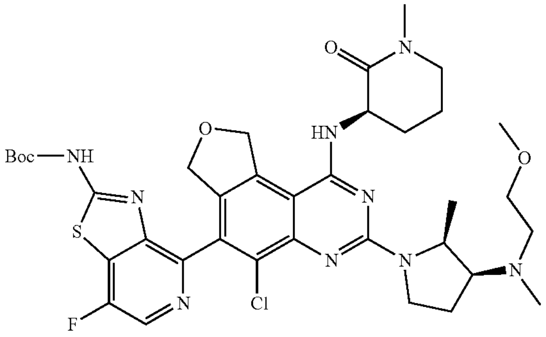 [SMILES: COCCN(C)[C@H]1CCN(c2nc(N[C@@H]3CCCN(C)C3=O)c3c4c(c(-c5ncc(F)c6sc(NC(=O)OC(C)(C)C)nc56)c(Cl)c3n2)COC4)[C@H]1C] | 770 |

TABLE 9-continued

| Preparation | Chemical Name | Structure | MS (ES) m/z (M + 1) |
|---|---|---|---|
| 43A | tert-butyl (4-(5-chloro-3-((2S,3S)-3-(dimethylamino)-2-methylpyrrolidin-1-yl)-1-(((R)-1-methyl-2-oxopiperidin-3-yl)amino)-7,9-dihydrofuro[3,4-f]quinazolin-6-yl)-6-fluorobenzo[d]thiazol-2-yl)carbamate | 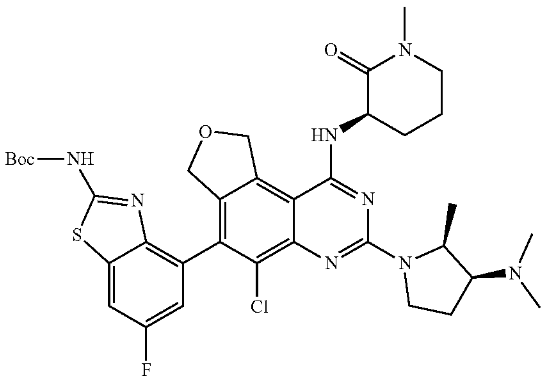 [SMILES: C[C@H]1[C@@H](N(C)C)CCN1c1nc(N[C@@H]2CCCN(C)C2=O)c2c3c(c(-c4cc(F)cc5sc(NC(=O)OC(C)(C)C)nc45)c(Cl)c2n1)COC3] | 725 |
| 44A | tert-butyl (4-(5-chloro-3-((2S,3S)-3-(dimethylamino)-2-methylpyrrolidin-1-yl)-1-(((R)-1-methyl-2-oxopiperidin-3-yl)amino)-7,9-dihydrofuro[3,4-f]quinazolin-6-yl)benzo[d]oxazol-2-yl)carbamate | 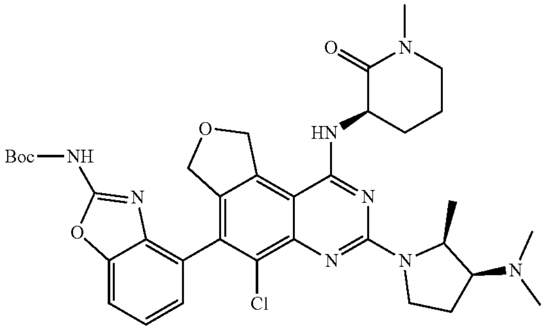 [SMILES: C[C@H]1[C@@H](N(C)C)CCN1c1nc(N[C@@H]2CCCN(C)C2=O)c2c3c(c(-c4cccc5oc(NC(=O)OC(C)(C)C)nc45)c(Cl)c2n1)COC3] | 591 |

[1]Clean isomer at the 3-position of the piperidinone, chiral purification from Preparation 31A

Example 1

(3R)-3-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-1-methylpiperidin-2-one

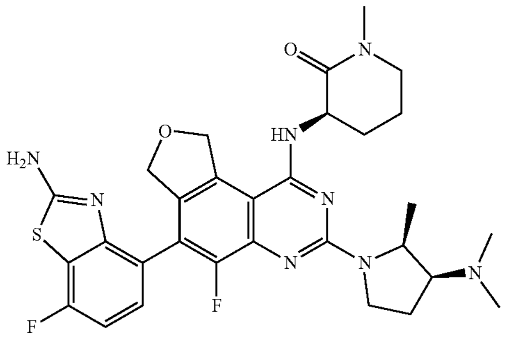

tert-Butyl (4-(3-((2S,3S)-3-(dimethylamino)-2-methylpyrrolidin-1-yl)-5-fluoro-1—(((R)-1-methyl-2-oxopiperidin-3-yl)amino)-7,9-dihydrofuro[3,4-f]quinazolin-6-yl)-7-fluorobenzo[d]thiazol-2-yl)carbamate (0.040 g, 0.056 mmol) was added to a mixture of chloroform (0.5 mL) and trifluoroacetic acid (0.5 mL). The mixture was stirred at room temperature. After 1 h, the mixture was purified by reversed phase purification, eluting with 10-100% acetonitrile in (95:5 10 mM aqueous ammonium bicarbonate: methanol), to give the title compound (0.036 g, 100%). MS (ES) m/z=609 (M+1).

The following compounds in Table 10 were prepared in similar manner as described in Example 1. Different neutral or acidic conditions, such as hexafluoroisopropanol, or HCl in 1,4-dioxane, may have been substituted. Various methods were used to purify the compounds, which would be apparent to one skilled in the art. Isomer separation methods may be found as footnotes.

TABLE 10

| Example | Chemical Name | Structure | MS (ES) m/z (M + 1) |
|---|---|---|---|
| 2[1] | (3R)-3-((6-(2-Amino-5,7-difluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-1-methylpiperidin-2-one, Atropisomer 1 | 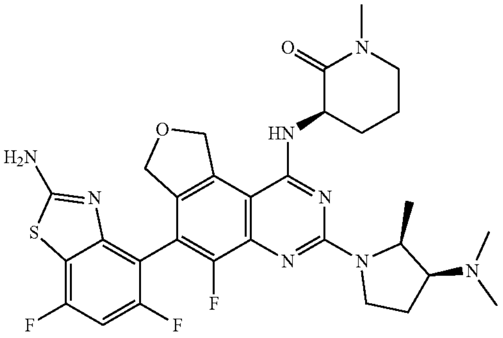 | 627 |
| 3[1] | (3R)-3-((6-(2-Amino-5,7-difluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-1-methylpiperidin-2-one, Atropisomer 2 | 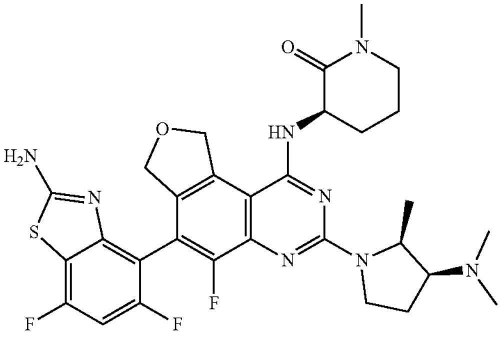 [SMILES: C[C@H]1[C@@H](N(C)C)CCN1c1nc(N[C@@H]2CCCN(C)C2=O)c2c3c(c(-c4c(F)cc(F)c5sc(N)nc45)c(F)c2n1)COC3] | 627 |
| 4[2] | (3R)-3-((6-(2-Amino-5,7-difluorobenzo[d]thiazol-4-yl)-3-((2S,3S)-3-(ethyl(methyl)amino)-2-methylpyrrolidin-1-yl)-5-fluoro-7,9-dihydrofuro[3,4-f]quinazolin-1-yl)amino)-1-methylpiperidin-2-one, Atropisomer 1 | 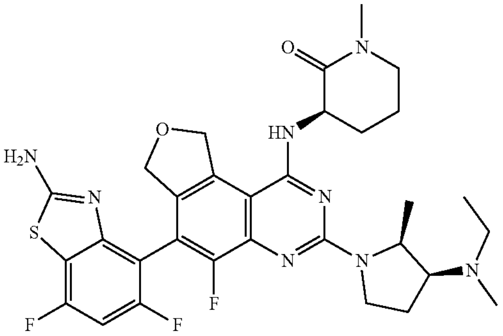 [SMILES: CCN(C)[C@H]1CCN(c2nc(N[C@@H]3CCCN(C)C3=O)c3c4c(c(-c5c(F)cc(F)c6sc(N)nc56)c(F)c3n2)COC4)[C@H]1C] | 641 |
| 5[2] | (3R)-3-((6-(2-Amino-5,7-difluorobenzo[d]thiazol-4-yl)-3-((2S,3S)-3-(ethyl(methyl)amino)-2-methylpyrrolidin-1-yl)-5-fluoro-7,9-dihydrofuro[3,4-f]quinazolin-1-yl)amino)-1-methylpiperidin-2-one, Atropisomer 2 | 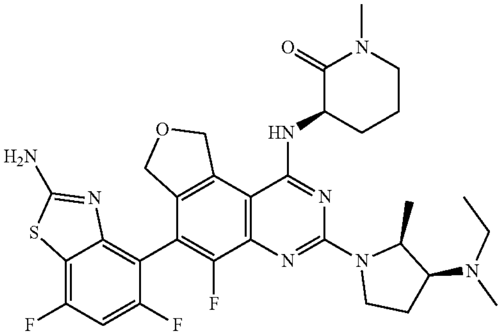 [SMILES: CCN(C)[C@H]1CCN(c2nc(N[C@@H]3CCCN(C)C3=O)c3c4c(c(-c5c(F)cc(F)c6sc(N)nc56)c(F)c3n2)COC4)[C@H]1C] | 641 |

TABLE 10-continued

| Example | Chemical Name | Structure | MS (ES) m/z (M + 1) |
|---|---|---|---|
| 6[3] | (3R)-3-((6-(2-Amino-5,7-difluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-1-methylpiperidin-2-one, Atropisomer 1 | 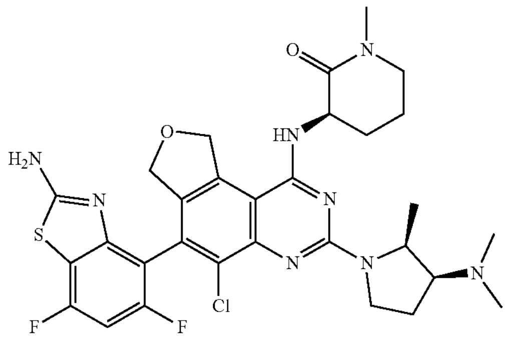 [SMILES: C[C@H]1[C@@H](N(C)C)CCN1c1nc(N[C@@H]2CCCN(C)C2=O)c2c3c(c(-c4c(F)cc(F)c5sc(N)nc45)c(Cl)c2n1)COC3] | 643 |
| 7[3] | (3R)-3-((6-(2-Amino-5,7-difluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-1-methylpiperidin-2-one, Atropisomer 2 | 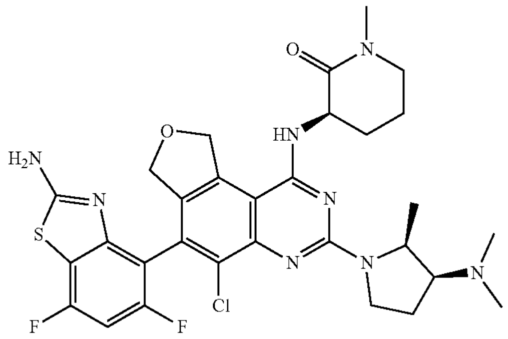 [SMILES: C[C@H]1[C@@H](N(C)C)CCN1c1nc(N[C@@H]2CCCN(C)C2=O)c2c3c(c(-c4c(F)cc(F)c5sc(N)nc45)c(Cl)c2n1)COC3] | 643 |
| 8[4] | (3R)-3-((6-(2-Amino-5,7-difluorobenzo[d]thiazol-4-yl)-5-chloro-3-((2S,3S)-3-(isopropyl(methyl)amino)-2-methylpyrrolidin-1-yl)-7,9-dihydrofuro[3,4-f]quinazolin-1-yl)amino)-1-methylpiperidin-2-one, Atropisomer 1 | 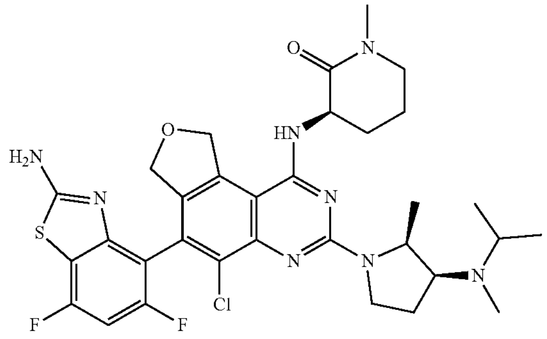 [SMILES: CC(C)N(C)[C@H]1CCN(c2nc(N[C@@H]3CCCN(C)C3=O)c3c4c(c(-c5c(F)cc(F)c6sc(N)nc56)c(Cl)c3n2)COC4)[C@H]1C] | 671 |
| 9[4] | (3R)-3-((6-(2-Amino-5,7-difluorobenzo[d]thiazol-4-yl)-5-chloro-3-((2S,3S)-3-(isopropyl(methyl)amino)-2-methylpyrrolidin-1-yl)-7,9-dihydrofuro[3,4-f]quinazolin-1-yl)amino)-1-methylpiperidin-2-one, Atropisomer 2 | 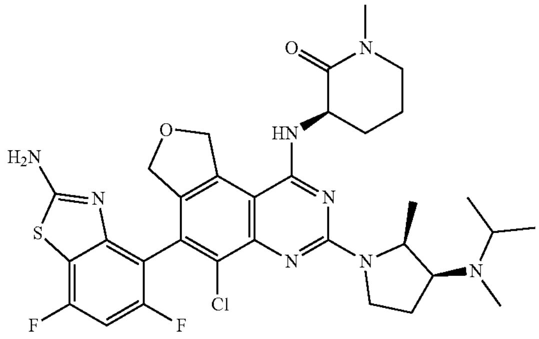 [SMILES: CC(C)N(C)[C@H]1CCN(c2nc(N[C@@H]3CCCN(C)C3=O)c3c4c(c(-c5c(F)cc(F)c6sc(N)nc56)c(Cl)c3n2)COC4)[C@H]1C] | 671 |

TABLE 10-continued

| Example | Chemical Name | Structure | MS (ES) m/z (M + 1) |
|---|---|---|---|
| 10[5] | (3R)-3-((6-(2-Amino-5,7-difluorobenzo[d]thiazol-4-yl)-5-chloro-3-(((2S,4R)-4-fluoro-1-methylpyrrolidin-2-yl)methoxy)-7,9-dihydrofuro[3,4-f]quinazolin-1-yl)amino)-1-methylpiperidin-2-one, Atropisomer 1 | 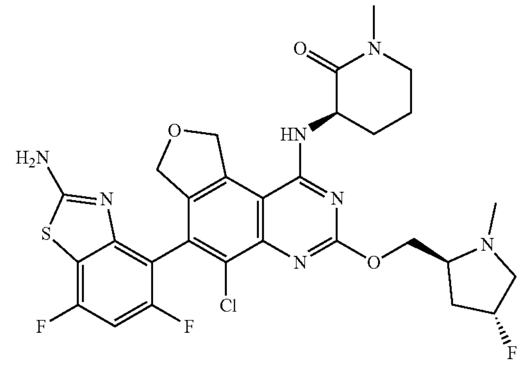 [SMILES: CN1CCC[C@@H](Nc2nc(OC[C@@H]3C[C@@H](F)CN3C)nc3c(Cl)c(-c4c(F)cc(F)c5sc(N)nc45)c4c(c23)COC4)C1=O] | 648 |
| 11[5] | (3R)-3-((6-(2-Amino-5,7-difluorobenzo[d]thiazol-4-yl)-5-chloro-3-(((2S,4R)-4-fluoro-1-methylpyrrolidin-2-yl)methoxy)-7,9-dihydrofuro[3,4-f]quinazolin-1-yl)amino)-1-methylpiperidin-2-one, Atropisomer 2 | 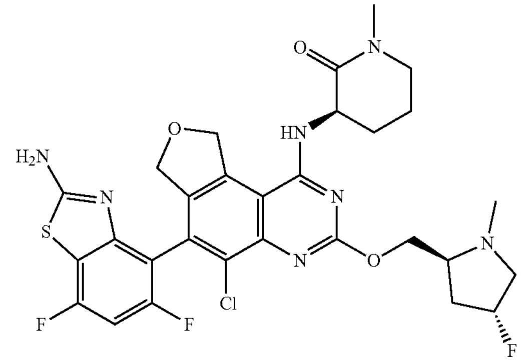 [SMILES: CN1CCC[C@@H](Nc2nc(OC[C@@H]3C[C@@H](F)CN3C)nc3c(Cl)c(-c4c(F)cc(F)c5sc(N)nc45)c4c(c23)COC4)C1=O] | 648 |
| 12[6] | (6R)-3-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-1,6-dimethylpiperidin-2-one, Enantiomer 1 | 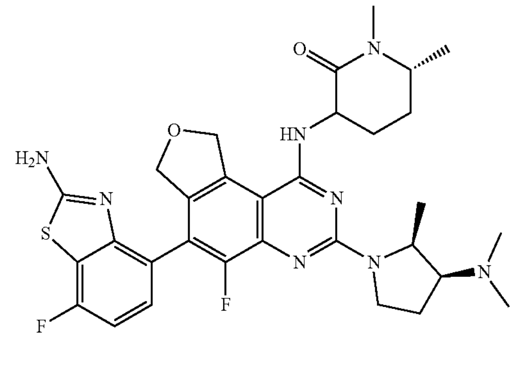 [SMILES: C[C@@H]1CCC(Nc2nc(N3CC[C@H](N(C)C)[C@@H]3C)nc3c(F)c(-c4ccc(F)c5sc(N)nc45)c4c(c23)COC4)C(=O)N1C] | 623 |
| 13[6] | (6R)-3-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-1,6-dimethylpiperidin-2-one, Enantiomer 2 | 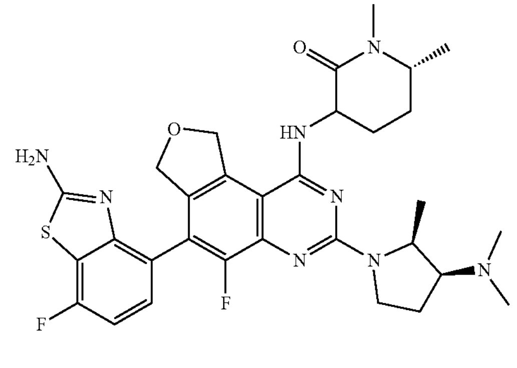 [SMILES: C[C@@H]1CCC(Nc2nc(N3CC[C@H](N(C)C)[C@@H]3C)nc3c(F)c(-c4ccc(F)c5sc(N)nc45)c4c(c23)COC4)C(=O)N1C] | 623 |

TABLE 10-continued

| Example | Chemical Name | Structure | MS (ES) m/z (M + 1) |
|---|---|---|---|
| 14[7] | (6S)-3-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-1,6-dimethylpiperidin-2-one, Enantiomer 1 | 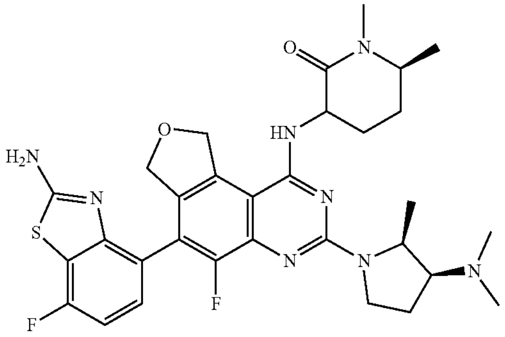 [SMILES: C[C@H]1CCC(Nc2nc(N3CC[C@H](N(C)C)[C@@H]3C)nc3c(F)c(-c4ccc(F)c5sc(N)nc45)c4c(c23)COC4)C(=O)N1C] | 623 |
| 15[7] | (6S)-3-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-1,6-dimethylpiperidin-2-one, Enantiomer 2 | 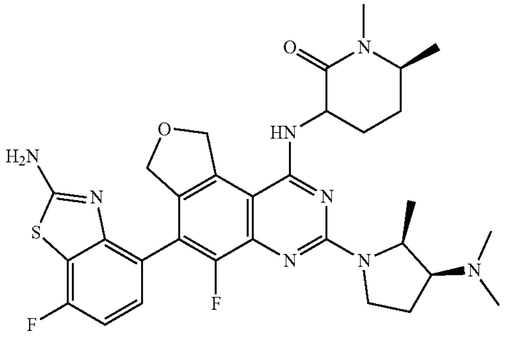 [SMILES: C[C@H]1CCC(Nc2nc(N3CC[C@H](N(C)C)[C@@H]3C)nc3c(F)c(-c4ccc(F)c5sc(N)nc45)c4c(c23)COC4)C(=O)N1C] | 623 |
| 16 | (3R)-3-((6-(2-Amino-7-fluorobenzo[d]thiazol-4-yl)-3-((2S,3S)-3-(ethyl(methyl)amino)-2-methylpyrrolidin-1-yl)-5-fluoro-7,9-dihydrofuro[3,4-f]quinazolin-1-yl)amino)-1-methylpiperidin-2-one | 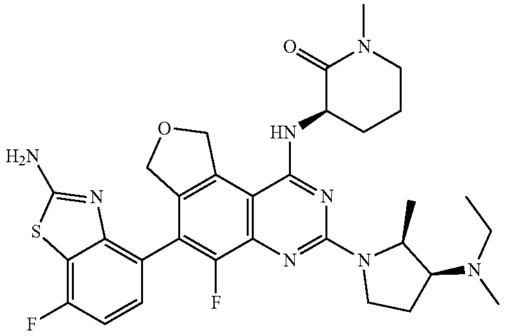 [SMILES: CCN(C)[C@H]1CCN(c2nc(N[C@@H]3CCCN(C)C3=O)c3c4c(c(-c5ccc(F)c6sc(N)nc56)c(F)c3n2)COC4)[C@H]1C] | 623 |
| 17 | (3R)-3-((6-(2-Amino-7-fluorobenzo[d]thiazol-4-yl)-5-fluoro-3-(((2S,4R)-4-fluoro-1-methylpyrrolidin-2-yl)methoxy)-7,9-dihydrofuro[3,4-f]quinazolin-1-yl)amino)-1-methylpiperidin-2-one | 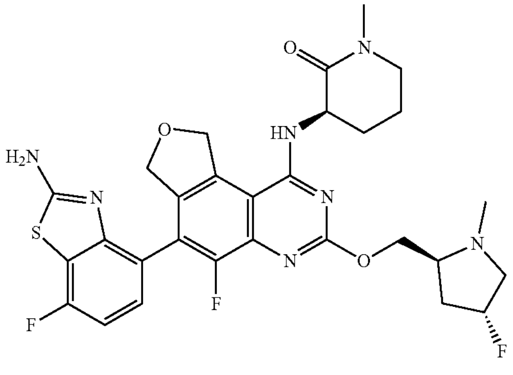 [SMILES: CN1CCC[C@@H](Nc2nc(OC[C@@H]3C[C@@H](F)CN3C)nc3c(F)c(-c4ccc(F)c5sc(N)nc45)c4c(c23)COC4)C1=O] | 614 |

TABLE 10-continued

| Example | Chemical Name | Structure | MS (ES) m/z (M + 1) |
|---|---|---|---|
| 18 | (3R)-3-((6-(2-Amino-7-fluorobenzo[d]thiazol-4-yl)-5-fluoro-3-(((2R,4R)-4-fluoro-1-methylpyrrolidin-2-yl)methoxy)-7,9-dihydrofuro[3,4-f]quinazolin-1-yl)amino)-1-methylpiperidin-2-one | 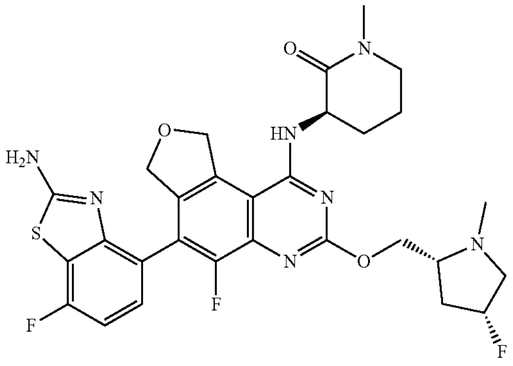 [SMILES: CN1CCC[C@@H](Nc2nc(OC[C@H]3C[C@@H](F)CN3C)nc3c(F)c(-c4ccc(F)c5sc(N)nc45)c4c(c23)COC4)C1=O] | 614 |
| 19 | (3R)-3-((6-(2-Amino-7-fluorobenzo[d]thiazol-4-yl)-3-((2S,3S)-3-(diethylamino)-2-methylpyrrolidin-1-yl)-5-fluoro-7,9-dihydrofuro[3,4-f]quinazolin-1-yl)amino)-1-methylpiperidin-2-one | 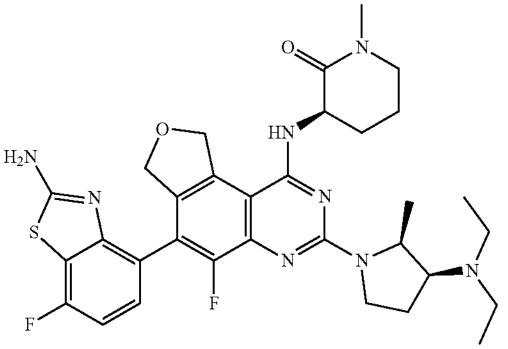 [SMILES: CCN(CC)[C@H]1CCN(c2nc(N[C@@H]3CCCN(C)C3=O)c3c4c(c(-c5ccc(F)c6sc(N)nc56)c(F)c3n2)COC4)[C@H]1C] | 637 |
| 20[8] | (3R)-3-((6-(2-Amino-7-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-1-methylpiperidin-2-one, Atropisomer 1 | 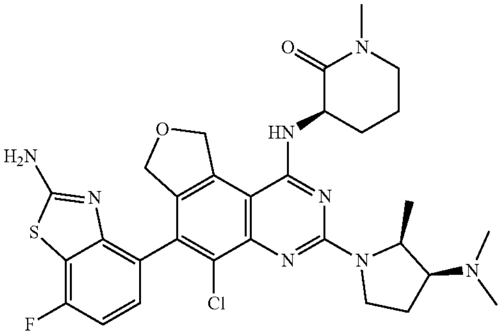 [SMILES: C[C@H]1[C@@H](N(C)C)CCN1c1nc(N[C@@H]2CCCN(C)C2=O)c2c3c(c(-c4ccc(F)c5sc(N)nc45)c(Cl)c2n1)COC3] | 625 |
| 21[8] | (3R)-3-((6-(2-Amino-7-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-1-methylpiperidin-2-one, Atropisomer 2 | 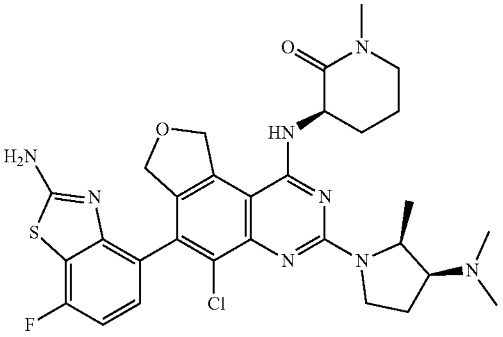 [SMILES: C[C@H]1[C@@H](N(C)C)CCN1c1nc(N[C@@H]2CCCN(C)C2=O)c2c3c(c(-c4ccc(F)c5sc(N)nc45)c(Cl)c2n1)COC3] | 625 |

TABLE 10-continued

| Example | Chemical Name | Structure | MS (ES) m/z (M + 1) |
| --- | --- | --- | --- |
| 22[9] | (3R)-3-((6-(2-Amino-7-fluorobenzo[d]thiazol-4-yl)-5-chloro-3-((2S,3S)-3-(isopropylamino)-2-methylpyrrolidin-1-yl)-7,9-dihydrofuro[3,4-f]quinazolin-1-yl)amino)-1-methylpiperidin-2-one, Atropisomer 1 | 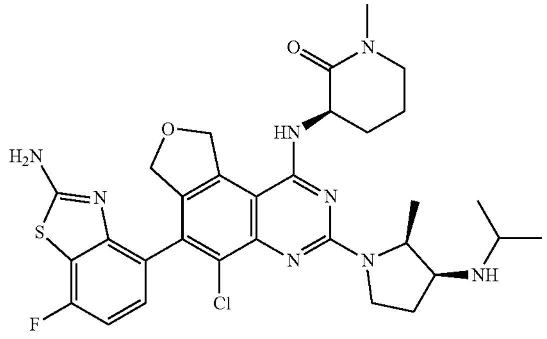 [SMILES: CC(C)N[C@H]1CCN(c2nc(N[C@@H]3CCCN(C)C3=O)c3c4c(c(-c5ccc(F)c6sc(N)nc56)c(Cl)c3n2)COC4)[C@H]1C] | 639 |
| 23[9] | (3R)-3-((6-(2-Amino-7-fluorobenzo[d]thiazol-4-yl)-5-chloro-3-((2S,3S)-3-(isopropylamino)-2-methylpyrrolidin-1-yl)-7,9-dihydrofuro[3,4-f]quinazolin-1-yl)amino)-1-methylpiperidin-2-one, Atropisomer 2 | 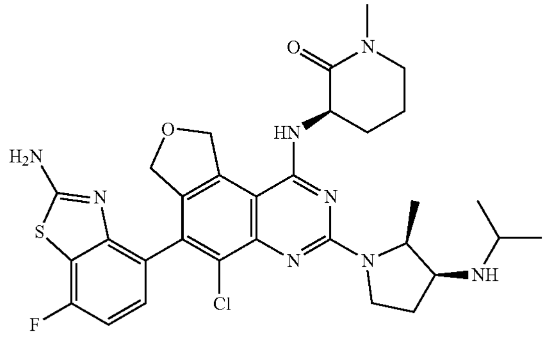 [SMILES: CC(C)N[C@H]1CCN(c2nc(N[C@@H]3CCCN(C)C3=O)c3c4c(c(-c5ccc(F)c6sc(N)nc56)c(Cl)c3n2)COC4)[C@H]1C] | 639 |
| 24[10] | (6S)-3-((6-(2-Amino-7-fluorobenzo[d]thiazol-4-yl)-5-chloro-3-((S)-3-(dimethylamino)pyrrolidin-1-yl)-7,9-dihydrofuro[3,4-f]quinazolin-1-yl)amino)-1,6-dimethylpiperidin-2-one, Diastereomer 1 | 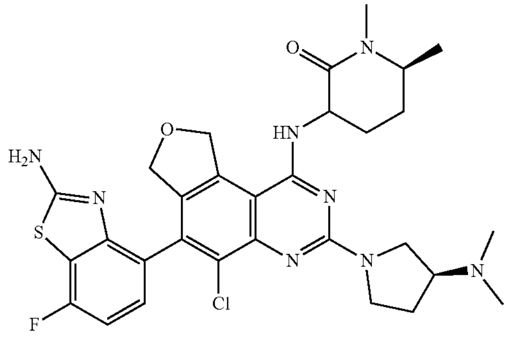 [SMILES: C[C@H]1CCC(Nc2nc(N3CC[C@H](N(C)C)C3)nc3c(Cl)c(-c4ccc(F)c5sc(N)nc45)c4c(c23)COC4)C(=O)N1C] | 625 |
| 25[10] | (6S)-3-((6-(2-Amino-7-fluorobenzo[d]thiazol-4-yl)-5-chloro-3-((S)-3-(dimethylamino)pyrrolidin-1-yl)-7,9-dihydrofuro[3,4-f]quinazolin-1-yl)amino)-1,6-dimethylpiperidin-2-one, Diastereomer 2 | 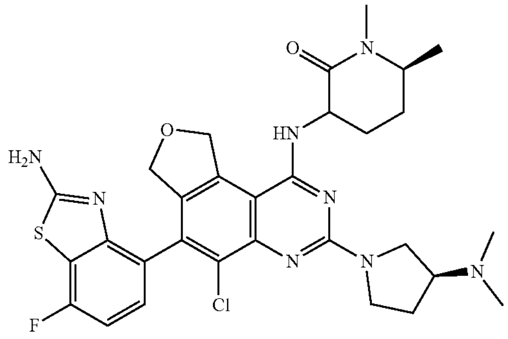 [SMILES: C[C@H]1CCC(Nc2nc(N3CC[C@H](N(C)C)C3)nc3c(Cl)c(-c4ccc(F)c5sc(N)nc45)c4c(c23)COC4)C(=O)N1C] | 625 |

TABLE 10-continued

| Example | Chemical Name | Structure | MS (ES) m/z (M + 1) |
|---|---|---|---|
| 26[10] | (6S)-3-((6-(2-Amino-7-fluorobenzo[d]thiazol-4-yl)-5-chloro-3-((S)-3-(dimethylamino)pyrrolidin-1-yl)-7,9-dihydrofuro[3,4-f]quinazolin-1-yl)amino)-1,6-dimethylpiperidin-2-one, Diastereomer 3 | 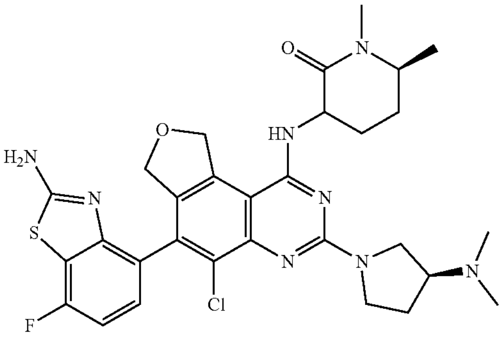 [SMILES: C[C@H]1CCC(Nc2nc(N3CC[C@H](N(C)C)C3)nc3c(Cl)c(-c4ccc(F)c5sc(N)nc45)c4c(c23)COC4)C(=O)N1C] | 625 |
| 27[10] | (6S)-3-((6-(2-Amino-7-fluorobenzo[d]thiazol-4-yl)-5-chloro-3-((S)-3-(dimethylamino)pyrrolidin-1-yl)-7,9-dihydrofuro[3,4-f]quinazolin-1-yl)amino)-1,6-dimethylpiperidin-2-one, Diastereomer 4 | 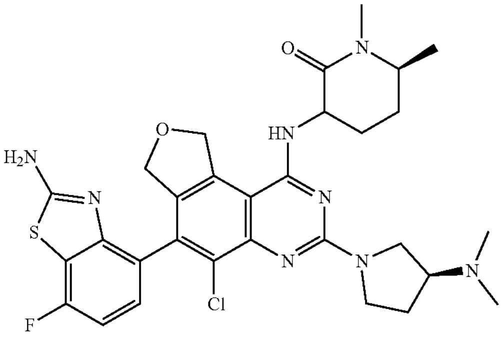 [SMILES: C[C@H]1CCC(Nc2nc(N3CC[C@H](N(C)C)C3)nc3c(Cl)c(-c4ccc(F)c5sc(N)nc45)c4c(c23)COC4)C(=O)N1C] | 625 |
| 28 | (3R)-3-((6-(2-Amino-7-fluorothiazolo[4,5-c]pyridin-4-yl)-5-chloro-3-((2S,3S)-3-(dimethylamino)-2-methylpyrrolidin-1-yl)-7,9-dihydrofuro[3,4-f]quinazolin-1-yl)amino)-1-methylpiperidin-2-one | 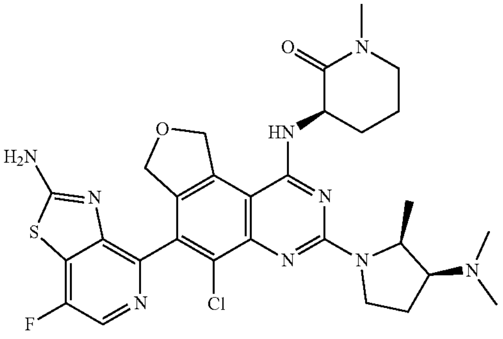 [SMILES: C[C@H]1[C@@H](N(C)C)CCN1c1nc(N[C@@H]2CCCN(C)C2=O)c2c3c(c(-c4ncc(F)c5sc(N)nc45)c(Cl)c2n1)COC3] | 626 |
| 29 | (3R)-3-((6-(2-Amino-7-fluorothiazolo[4,5-c]pyridin-4-yl)-5-chloro-3-((2S,3S)-3-(ethyl(methyl)amino)-2-methylpyrrolidin-1-yl)-7,9-dihydrofuro[3,4-f]quinazolin-1-yl)amino)-1-methylpiperidin-2-one | 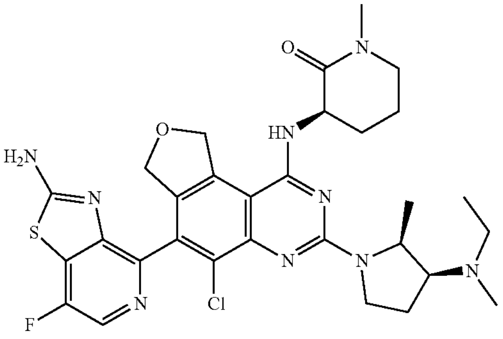 [SMILES: CCN(C)[C@H]1CCN(c2nc(N[C@@H]3CCCN(C)C3=O)c3c4c(c(-c5ncc(F)c6sc(N)nc56)c(Cl)c3n2)COC4)[C@H]1C] | 640 |

TABLE 10-continued

| Example | Chemical Name | Structure | MS (ES) m/z (M + 1) |
|---|---|---|---|
| 30 | (3R)-3-((6-(2-Amino-7-fluorothiazolo[4,5-c]pyridin-4-yl)-5-chloro-3-((2S,3S)-3-(isopropyl(methyl)amino)-2-methylpyrrolidin-1-yl)-7,9-dihydrofuro[3,4-f]quinazolin-1-yl)amino)-1-methylpiperidin-2-one | 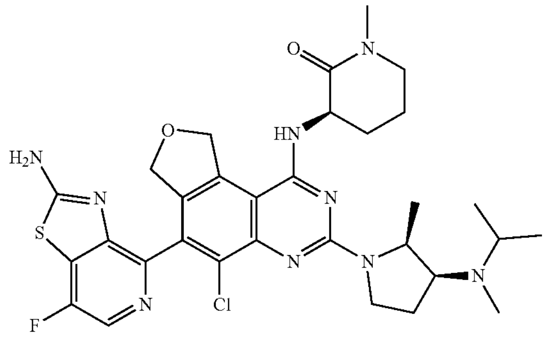 [SMILES: CC(C)N(C)[C@H]1CCN(c2nc(N[C@@H]3CCCN(C)C3=O)c3c4c(c(-c5ncc(F)c6sc(N)nc56)c(Cl)c3n2)COC4)[C@H]1C] | 654 |
| 31[11] | (3R)-3-((6-(2-Amino-5-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-1-methylpiperidin-2-one, Atropisomer 1 | 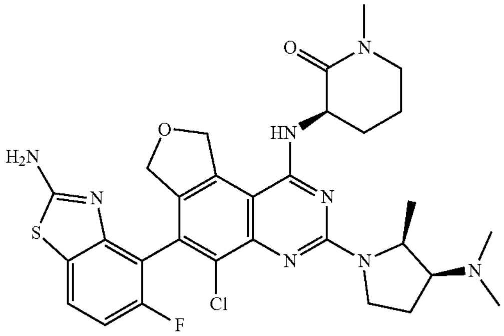 [SMILES: C[C@H]1[C@@H](N(C)C)CCN1c1nc(N[C@@H]2CCCN(C)C2=O)c2c3c(c(-c4c(F)ccc5sc(N)nc45)c(Cl)c2n1)COC3] | 625 |
| 32[11] | (3R)-3-((6-(2-Amino-5-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-1-methylpiperidin-2-one, Atropisomer 2 | 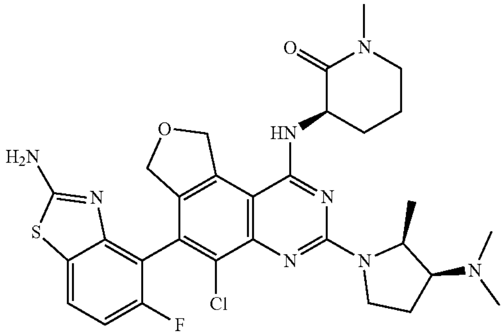 [SMILES: C[C@H]1[C@@H](N(C)C)CCN1c1nc(N[C@@H]2CCCN(C)C2=O)c2c3c(c(-c4c(F)ccc5sc(N)nc45)c(Cl)c2n1)COC3] | 625 |
| 33 | (3R)-3-((6-(2-Amino-7-chlorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-1-methylpiperidin-2-one | 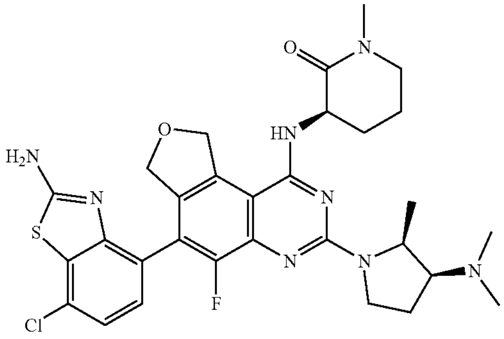 [SMILES: C[C@H]1[C@@H](N(C)C)CCN1c1nc(N[C@@H]2CCCN(C)C2=O)c2c3c(c(-c4ccc(Cl)c5sc(N)nc45)c(F)c2n1)COC3] | 625 |

TABLE 10-continued

| Example | Chemical Name | Structure | MS (ES) m/z (M + 1) |
|---|---|---|---|
| 34[12] | (3R)-3-((6-(2-Amino-5,7-difluorobenzo[d]thiazol-4-yl)-5-chloro-3-(((2S,4R)-4-methoxy-1-methylpyrrolidin-2-yl)methoxy)-7,9-dihydrofuro[3,4-f]quinazolin-1-yl)amino)-1-methylpiperidin-2-one, Atropisomer 1 | 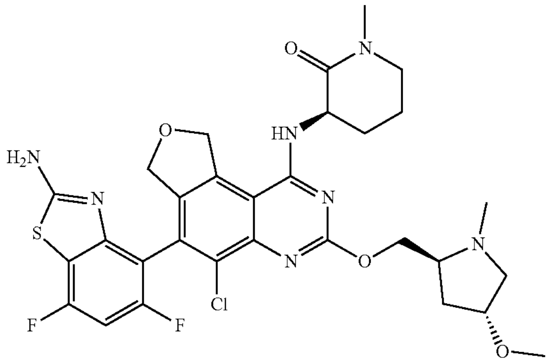 [SMILES: CO[C@@H]1C[C@@H](COc2nc(N[C@@H]3CCCN(C)C3=O)c3c4c(c(-c5c(F)cc(F)c6sc(N)nc56)c(Cl)c3n2)COC4)N(C)C1] | 660 |
| 35[12] | (3R)-3-((6-(2-Amino-5,7-difluorobenzo[d]thiazol-4-yl)-5-chloro-3-(((2S,4R)-4-methoxy-1-methylpyrrolidin-2-yl)methoxy)-7,9-dihydrofuro[3,4-f]quinazolin-1-yl)amino)-1-methylpiperidin-2-one, Atropisomer 2 | 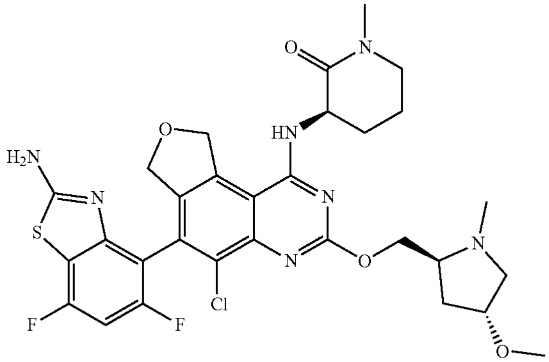 [SMILES: CO[C@@H]1C[C@@H](COc2nc(N[C@@H]3CCCN(C)C3=O)c3c4c(c(-c5c(F)cc(F)c6sc(N)nc56)c(Cl)c3n2)COC4)N(C)C1] | 660 |
| 36[13] | (3R)-3-((6-(2-Amino-5,7-difluorobenzo[d]thiazol-4-yl)-5-chloro-3-((S)-3-(diethylamino)pyrrolidin-1-yl)-7,9-dihydrofuro[3,4-f]quinazolin-1-yl)amino)-1-methylpiperidin-2-one, Atropisomer 1 | 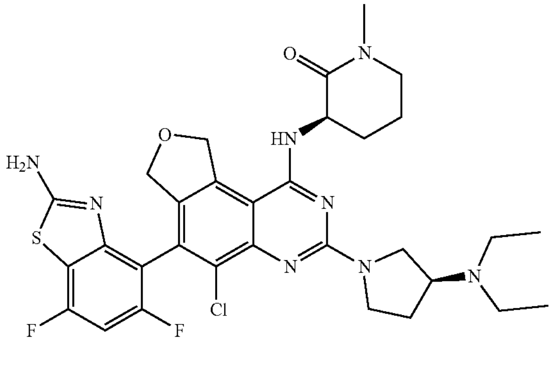 [SMILES: CCN(CC)[C@H]1CCN(c2nc(N[C@@H]3CCCN(C)C3=O)c3c4c(c(-c5c(F)cc(F)c6sc(N)nc56)c(Cl)c3n2)COC4)C1] | 657 |
| 37[13] | (3R)-3-((6-(2-Amino-5,7-difluorobenzo[d]thiazol-4-yl)-5-chloro-3-((S)-3-(diethylamino)pyrrolidin-1-yl)-7,9-dihydrofuro[3,4-f]quinazolin-1-yl)amino)-1-methylpiperidin-2-one, Atropisomer 2 | 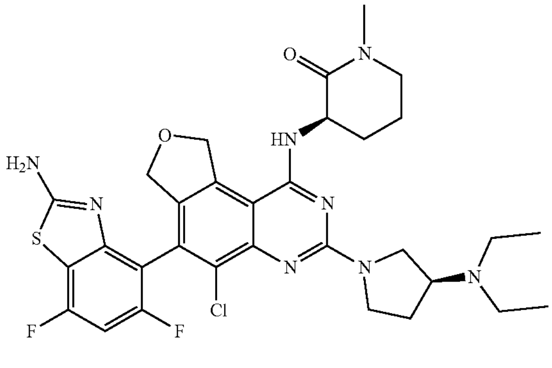 [SMILES: CCN(CC)[C@H]1CCN(c2nc(N[C@@H]3CCCN(C)C3=O)c3c4c(c(-c5c(F)cc(F)c6sc(N)nc56)c(Cl)c3n2)COC4)C1] | 657 |

TABLE 10-continued

| Example | Chemical Name | Structure | MS (ES) m/z (M + 1) |
|---|---|---|---|
| 38 | (3R)-3-((6-(2-Amino-7-fluorobenzo[d]thiazol-4-yl)-5-fluoro-3-((2S,3S)-3-(isopropyl(methyl)amino)-2-methylpyrrolidin-1-yl)-7,9-dihydrofuro[3,4-f]quinazolin-1-yl)amino)-1-methylpiperidin-2-one | 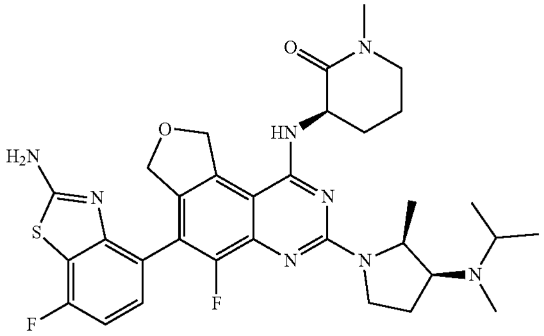 [SMILES: CC(C)N(C)[C@H]1CCN(c2nc(N[C@@H]3CCCN(C)C3=O)c3c4c(c(-c5ccc(F)c6sc(N)nc56)c(F)c3n2)COC4)[C@H]1C] | 637 |
| 39 | (3R)-3-((6-(2-Amino-7-fluorobenzo[d]thiazol-4-yl)-5-fluoro-3-((3R,4S)-3-(isopropyl(methyl)amino)-4-methylpyrrolidin-1-yl)-7,9-dihydrofuro[3,4-f]quinazolin-1-yl)amino)-1-methylpiperidin-2-one | 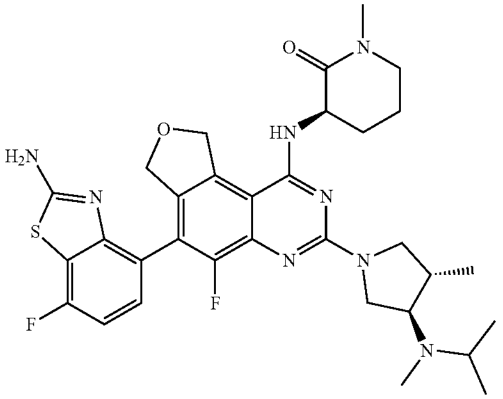 [SMILES: CC(C)N(C)[C@H]1CN(c2nc(N[C@@H]3CCCN(C)C3=O)c3c4c(c(-c5ccc(F)c6sc(N)nc56)c(F)c3n2)COC4)C[C@@H]1C] | 637 |
| 40[14] | (3R)-3-((6-(2-Amino-7-fluorobenzo[d]thiazol-4-yl)-3-(3-(ethyl(methyl)amino)-3-methylpyrrolidin-1-yl)-5-fluoro-7,9-dihydrofuro[3,4-f]quinazolin-1-yl)amino)-1-methylpiperidin-2-one, Isomer 1 | 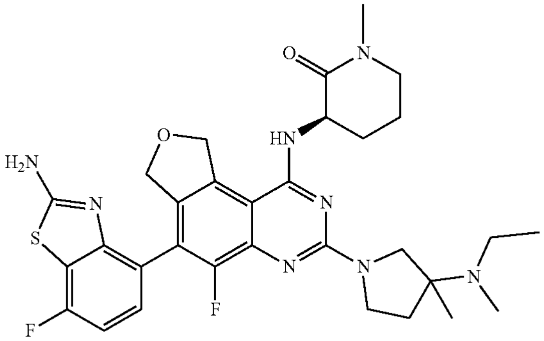 [SMILES: CCN(C)C1(C)CCN(c2nc(N[C@@H]3CCCN(C)C3=O)c3c4c(c(-c5ccc(F)c6sc(N)nc56)c(F)c3n2)COC4)C1] | 623 |
| 41[14] | (3R)-3-((6-(2-Amino-7-fluorobenzo[d]thiazol-4-yl)-3-(3-(ethyl(methyl)amino)-3-methylpyrrolidin-1-yl)-5-fluoro-7,9-dihydrofuro[3,4-f]quinazolin-1-yl)amino)-1-methylpiperidin-2-one, Isomer 2 | 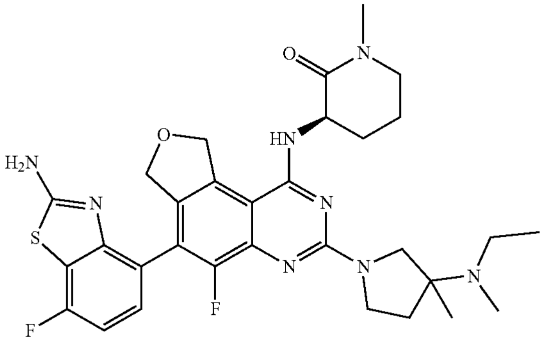 [SMILES: CCN(C)C1(C)CCN(c2nc(N[C@@H]3CCCN(C)C3=O)c3c4c(c(-c5ccc(F)c6sc(N)nc56)c(F)c3n2)COC4)C1] | 623 |

TABLE 10-continued

| Example | Chemical Name | Structure | MS (ES) m/z (M + 1) |
| --- | --- | --- | --- |
| 42 | (3R)-3-((6-(2-Amino-7-fluorobenzo[d]thiazol-4-yl)-5-fluoro-3-(((2R,4S)-4-fluoro-1-methylpyrrolidin-2-yl)methoxy)-7,9-dihydrofuro[3,4-f]quinazolin-1-yl)amino)-1-methylpiperidin-2-one | 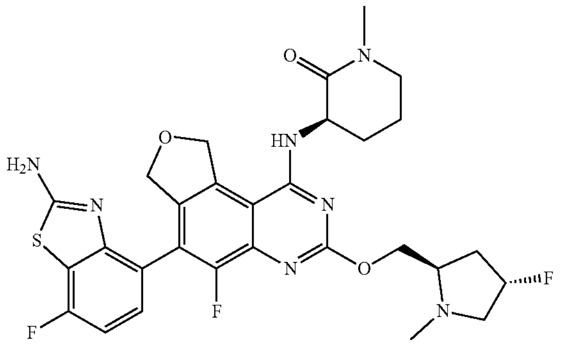 [SMILES: CN1CCC[C@@H](Nc2nc(OC[C@H]3C[C@H](F)CN3C)nc3c(F)c(-c4ccc(F)c5sc(N)nc45)c4c(c23)COC4)C1=O] | 613 |
| 43 | (3R)-3-((6-(2-Amino-7-fluorobenzo[d]thiazol-4-yl)-5-fluoro-3-((2'S,3'S)-2'-methyl-[1,3'-bipyrrolidin]-1'-yl)-7,9-dihydrofuro[3,4-f]quinazolin-1-yl)amino)-1-methylpiperidin-2-one | 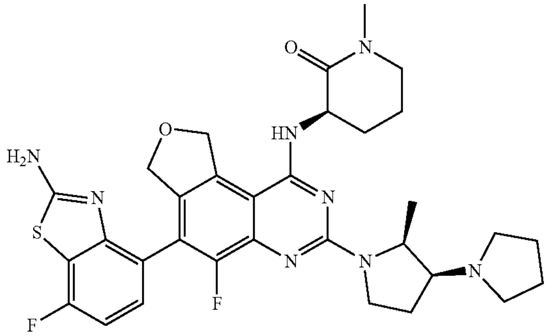 [SMILES: C[C@H]1[C@@H](N2CCCC2)CCN1c1nc(N[C@@H]2CCCN(C)C2=O)c2c3c(c(-c4ccc(F)c5sc(N)nc45)c(F)c2n1)COC3] | 635 |
| 44 | (3R)-3-((6-(2-Amino-7-fluorobenzo[d]thiazol-4-yl)-3-((2S,3S)-3-(azetidin-1-yl)-2-methylpyrrolidin-1-yl)-5-fluoro-7,9-dihydrofuro[3,4-f]quinazolin-1-yl)amino)-1-methylpiperidin-2-one | 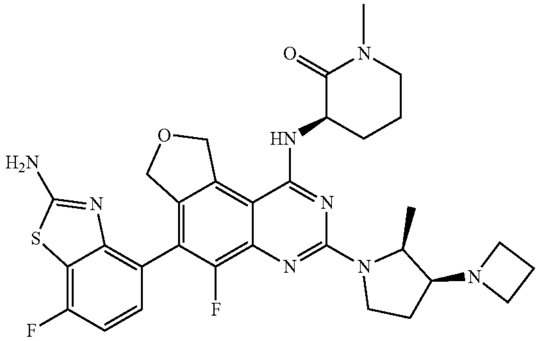 [SMILES: C[C@H]1[C@@H](N2CCC2)CCN1c1nc(N[C@@H]2CCCN(C)C2=O)c2c3c(c(-c4ccc(F)c5sc(N)nc45)c(F)c2n1)COC3] | 621 |
| 45[15] | (3R)-3-((6-(2-Amino-7-fluorobenzo[d]thiazol-4-yl)-5-chloro-3-((S)-3-(dimethylamino)pyrrolidin-1-yl)-7,9-dihydrofuro[3,4-f]quinazolin-1-yl)amino)-1-methylpiperidin-2-one, Atropisomer 1 | 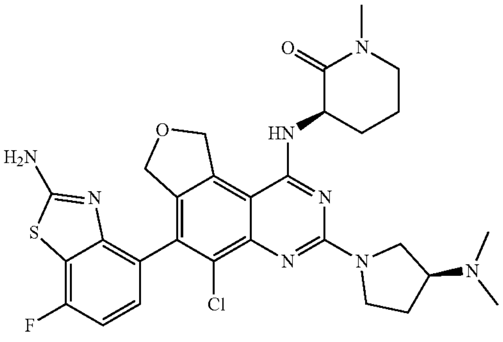 [SMILES: CN1CCC[C@@H](Nc2nc(N3CC[C@H](N(C)C)C3)nc3c(Cl)c(-c4ccc(F)c5sc(N)nc45)c4c(c23)COC4)C1=O] | 611 |

TABLE 10-continued

| Example | Chemical Name | Structure | MS (ES) m/z (M + 1) |
|---|---|---|---|
| 46[15] | (3R)-3-((6-(2-Amino-7-fluorobenzo[d]thiazol-4-yl)-5-chloro-3-((S)-3-(dimethylamino)pyrrolidin-1-yl)-7,9-dihydrofuro[3,4-f]quinazolin-1-yl)amino)-1-methylpiperidin-2-one, Atropisomer 2 | 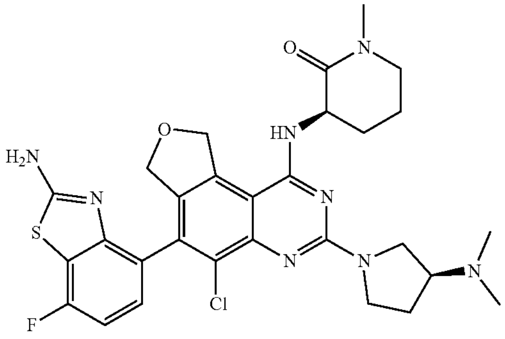 [SMILES: CN1CCC[C@@H](Nc2nc(N3CC[C@H](N(C)C)C3)nc3c(Cl)c(-c4ccc(F)c5sc(N)nc45)c4c(c23)COC4)C1=O] | 611 |
| 47[16] | (6R)-3-((6-(2-Amino-7-fluorothiazolo[4,5-c]pyridin-4-yl)-5-chloro-3-((2S,3S)-3-(dimethylamino)-2-methylpyrrolidin-1-yl)-7,9-dihydrofuro[3,4-f]quinazolin-1-yl)amino)-1,6-dimethylpiperidin-2-one | 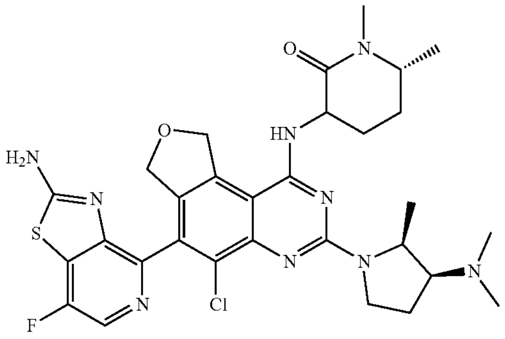 [SMILES: C[C@@H]1CCC(Nc2nc(N3CC[C@H](N(C)C)[C@@H]3C)nc3c(Cl)c(-c4ncc(F)c5sc(N)nc45)c4c(c23)COC4)C(=O)N1C] | 640 |
| 48 | (3R)-3-((6-(2-Amino-7-fluorothiazolo[4,5-c]pyridin-4-yl)-5-chloro-3-((2S,3S)-3-((2-methoxyethyl)(methyl)amino)-2-methylpyrrolidin-1-yl)-7,9-dihydrofuro[3,4-f]quinazolin-1-yl)amino)-1-methylpiperidin-2-one | 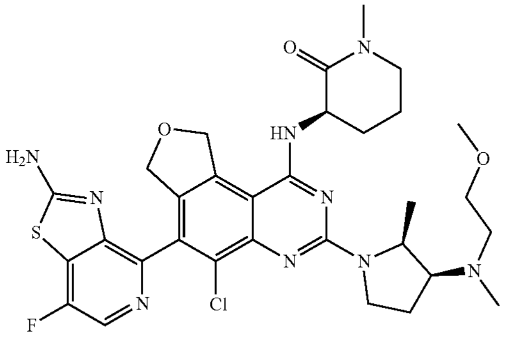 [SMILES: COCCN(C)[C@H]1CCN(c2nc(N[C@@H]3CCCN(C)C3=O)c3c4c(c(-c5ncc(F)c6sc(N)nc56)c(Cl)c3n2)COC4)[C@H]1C] | 670 |
| 49[17] | (3R)-3-((6-(2-Amino-5-fluorobenzo[d]thiazol-4-yl)-5-chloro-3-(((2S,4R)-4-fluoro-1-methylpyrrolidin-2-yl)methoxy)-7,9-dihydrofuro[3,4-f]quinazolin-1-yl)amino)-1-methylpiperidin-2-one, Atropisomer 1 | 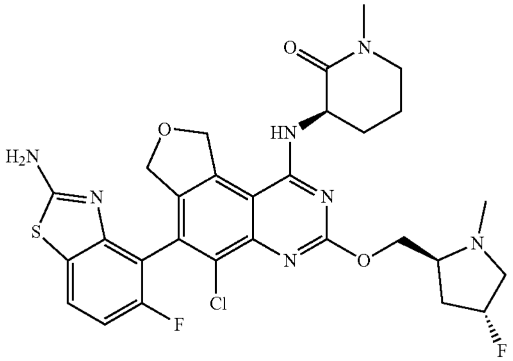 [SMILES: CN1CCC[C@@H](Nc2nc(OC[C@@H]3C[C@@H](F)CN3C)nc3c(Cl)c(-c4c(F)ccc5sc(N)nc45)c4c(c23)COC4)C1=O] | 630 |

TABLE 10-continued

| Example | Chemical Name | Structure | MS (ES) m/z (M + 1) |
|---|---|---|---|
| 50[17] | (3R)-3-((6-(2-Amino-5-fluorobenzo[d]thiazol-4-yl)-5-chloro-3-(((2S,4R)-4-fluoro-1-methylpyrrolidin-2-yl)methoxy)-7,9-dihydrofuro[3,4-f]quinazolin-1-yl)amino)-1-methylpiperidin-2-one, Atropisomer 2 | 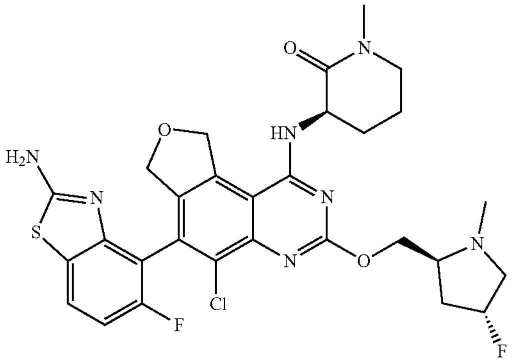 [SMILES: CN1CCC[C@@H](Nc2nc(OC[C@@H]3C[C@@H](F)CN3C)nc3c(Cl)c(-c4c(F)ccc5sc(N)nc45)c4c(c23)COC4)C1=O] | 630 |
| 51[18] | (3R)-3-((6-(2-Amino-5-fluorobenzo[d]thiazol-4-yl)-5-chloro-3-((2S,3S)-3-(isopropyl(methyl)amino)-2-methylpyrrolidin-1-yl)-7,9-dihydrofuro[3,4-f]quinazolin-1-yl)amino)-1-methylpiperidin-2-one, Atropisomer 1 | 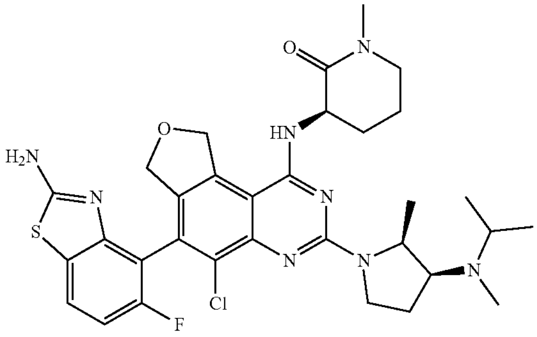 [SMILES: CC(C)N(C)[C@H]1CCN(c2nc(N[C@@H]3CCCN(C)C3=O)c3c4c(c(-c5c(F)ccc6sc(N)nc56)c(Cl)c3n2)COC4)[C@H]1C] | 653 |
| 52[18] | (3R)-3-((6-(2-Amino-5-fluorobenzo[d]thiazol-4-yl)-5-chloro-3-((2S,3S)-3-(isopropyl(methyl)amino)-2-methylpyrrolidin-1-yl)-7,9-dihydrofuro[3,4-f]quinazolin-1-yl)amino)-1-methylpiperidin-2-one, Atropisomer 2 | 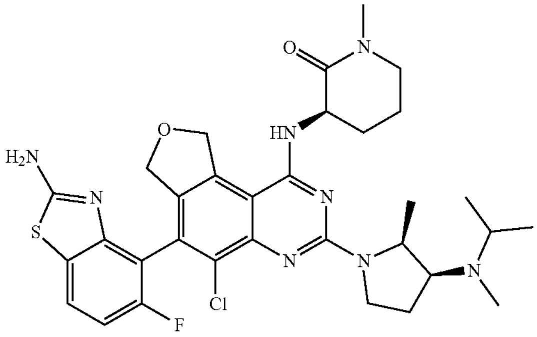 [SMILES: CC(C)N(C)[C@H]1CCN(c2nc(N[C@@H]3CCCN(C)C3=O)c3c4c(c(-c5c(F)ccc6sc(N)nc56)c(Cl)c3n2)COC4)[C@H]1C] | 653 |
| 53[19] | (3R)-3-((6-(2-Amino-5-fluorobenzo[d]thiazol-4-yl)-3-((2S,3S)-3-(azetidin-1-yl)-2-methylpyrrolidin-1-yl)-5-chloro-7,9-dihydrofuro[3,4-f]quinazolin-1-yl)amino)-1-methylpiperidin-2-one, Atropisomer 1 | 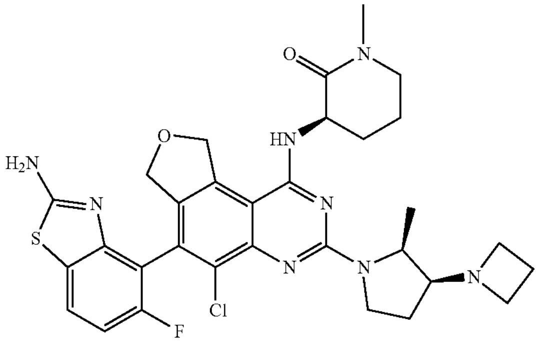 [SMILES: C[C@H]1[C@@H](N2CCC2)CCN1c1nc(N[C@@H]2CCCN(C)C2=O)c2c3c(c(-c4c(F)ccc5sc(N)nc45)c(Cl)c2n1)COC3] | 637 |

TABLE 10-continued

| Example | Chemical Name | Structure | MS (ES) m/z (M + 1) |
| --- | --- | --- | --- |
| 54[19] | (3R)-3-((6-(2-Amino-5-fluorobenzo[d]thiazol-4-yl)-3-((2S,3S)-3-(azetidin-1-yl)-2-methylpyrrolidin-1-yl)-5-chloro-7,9-dihydrofuro[3,4-f]quinazolin-1-yl)amino)-1-methylpiperidin-2-one, Atropisomer 2 | 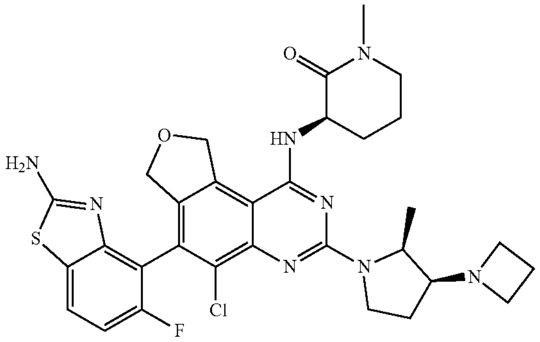 [SMILES: C[C@H]1[C@@H](N2CCC2)CCN1c1nc(N[C@@H]2CCCN(C)C2=O)c2c3c(c(-c4c(F)ccc5sc(N)nc45)c(Cl)c2n1)COC3] | 637 |
| 55[20] | (3R)-3-((6-(2-Amino-5-fluorobenzo[d]thiazol-4-yl)-5-chloro-3-((2S,3S)-3-(ethyl(methyl)amino)-2-methylpyrrolidin-1-yl)-7,9-dihydrofuro[3,4-f]quinazolin-1-yl)amino)-1-methylpiperidin-2-one, Atropisomer 1 | 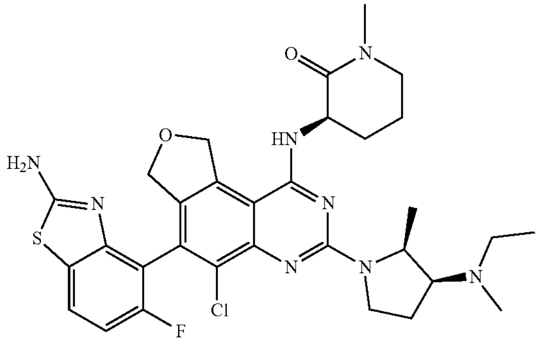 [SMILES: CCN(C)[C@H]1CCN(c2nc(N[C@@H]3CCCN(C)C3=O)c3c4c(c(-c5c(F)ccc6sc(N)nc56)c(Cl)c3n2)COC4)[C@H]1C] | 639 |
| 56[20] | (3R)-3-((6-(2-Amino-5-fluorobenzo[d]thiazol-4-yl)-5-chloro-3-((2S,3S)-3-(ethyl(methyl)amino)-2-methylpyrrolidin-1-yl)-7,9-dihydrofuro[3,4-f]quinazolin-1-yl)amino)-1-methylpiperidin-2-one, Atropisomer 2 | 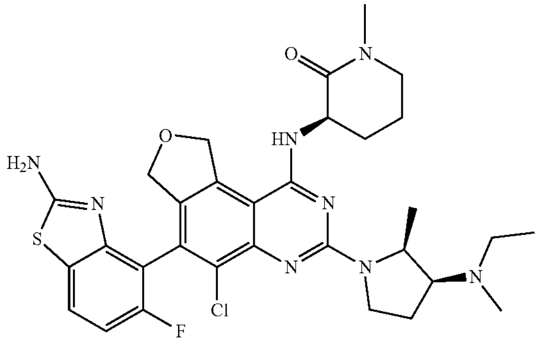 [SMILES: CCN(C)[C@H]1CCN(c2nc(N[C@@H]3CCCN(C)C3=O)c3c4c(c(-c5c(F)ccc6sc(N)nc56)c(Cl)c3n2)COC4)[C@H]1C] | 639 |
| 57 | (3R)-3-((6-(2-Amino-7-methylbenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-1-methylpiperidin-2-one | 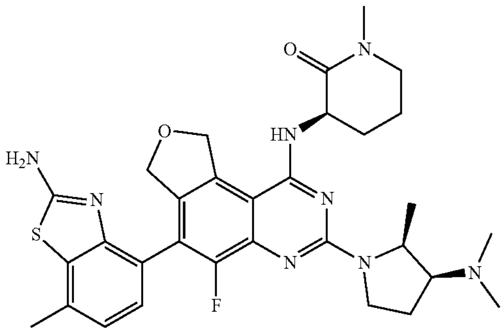 | 605 |

TABLE 10-continued

| Example | Chemical Name | Structure | MS (ES) m/z (M + 1) |
|---|---|---|---|
| 58 | (3R)-3-((6-(2-Aminobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-1-methylpiperidin-2-one | 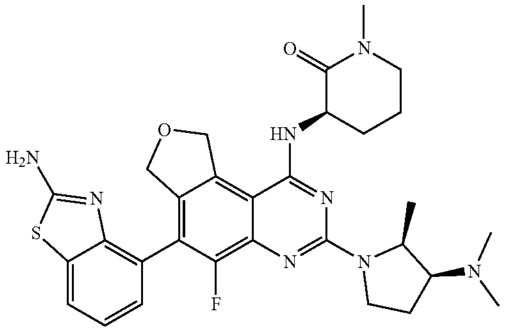 [SMILES: C[C@H]1[C@@H](N(C)C)CCN1c1nc(N[C@@H]2CCCN(C)C2=O)c2c3c(c(-c4cccc5sc(N)nc45)c(F)c2n1)COC3] | 591 |
| 59[21] | (3R)-3-((6-(2-Aminobenzo[d]thiazol-4-yl)-5-chloro-3-((2S,3S)-3-(isopropylamino)-2-methylpyrrolidin-1-yl)-7,9-dihydrofuro[3,4-f]quinazolin-1-yl)amino)-1-methylpiperidin-2-one, Atropisomer 1 | 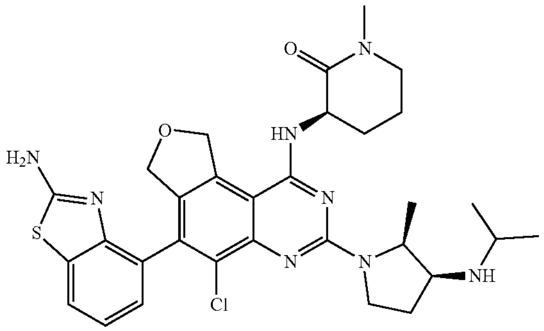 [SMILES: CC(C)N[C@H]1CCN(c2nc(N[C@@H]3CCCN(C)C3=O)c3c4c(c(-c5cccc6sc(N)nc56)c(Cl)c3n2)COC4)[C@H]1C] | 621 |
| 60[21] | (3R)-3-((6-(2-Aminobenzo[d]thiazol-4-yl)-5-chloro-3-((2S,3S)-3-(isopropylamino)-2-methylpyrrolidin-1-yl)-7,9-dihydrofuro[3,4-f]quinazolin-1-yl)amino)-1-methylpiperidin-2-one, Atropisomer 2 | 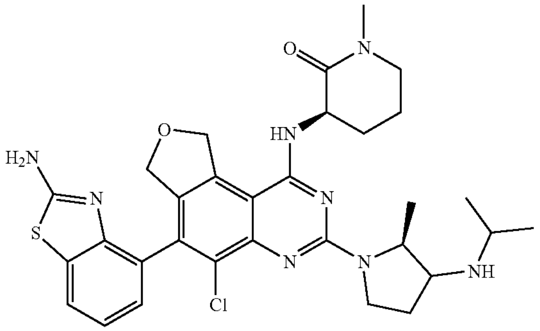 [SMILES: CC(C)NC1CCN(c2nc(N[C@@H]3CCCN(C)C3=O)c3c4c(c(-c5cccc6sc(N)nc56)c(Cl)c3n2)COC4)[C@H]1C] | 621 |
| 61 | (3R)-3-((6-(2-Amino-6-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-1-methylpiperidin-2-one | 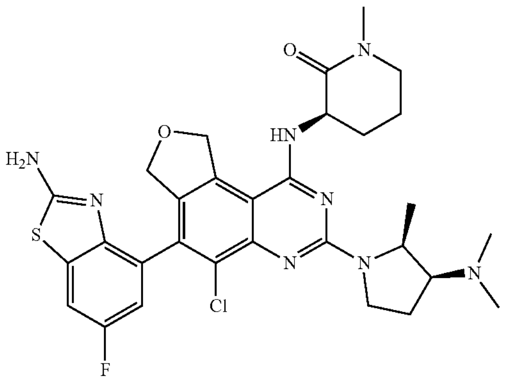 [SMILES: C[C@H]1[C@@H](N(C)C)CCN1c1nc(N[C@@H]2CCCN(C)C2=O)c2c3c(c(-c4cc(F)cc5sc(N)nc45)c(Cl)c2n1)COC3] | 625 |

TABLE 10-continued

| Example | Chemical Name | Structure | MS (ES) m/z (M + 1) |
|---|---|---|---|
| 62 | (3R)-3-((6-(2-Aminobenzo[d]oxazol-4-yl)-5-chloro-3-((2S,3S)-3-(dimethylamino)-2-methylpyrrolidin-1-yl)-7,9-dihydrofuro[3,4-f]quinazolin-1-yl)amino)-1-methylpiperidin-2-one | 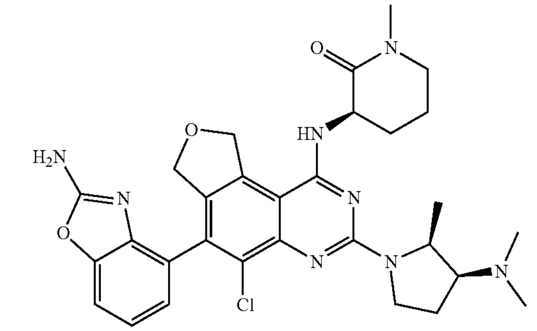 [SMILES: C[C@H]1[C@@H](N(C)C)CCN1c1nc(N[C@@H]2CCCN(C)C2=O)c2c3c(c(-c4cccc5oc(N)nc45)c(Cl)c2n1)COC3] | 591 |

[1]Prep-Chiral-HPLC; Phenomenex Lux i-Cellulose-5, 30 × 150 mm, 30-100% (ethanol w/0.1% isopropylamine) in heptane, 42.5 mL/min
[2]Reverse Phase; C18, 49-100% acetonitrile in (95:5 10 mM aqueous ammonium bicarbonate:methanol)
[3]Prep-Chiral-HPLC; (S,S)-Whelk-01, 30 × 150 mm, 20-95% ethanol in heptane, 45 mL/min
[4]Prep-Chiral-HPLC; Chiralpak IK, 30 × 250 mm, 50% ethanol in (10 mM ammoniated methanol in hexanes), 40 mL/min
[5]Reverse Phase; C18, 45-51% acetonitrile in 10 mM aqueous ammonium bicarbonate
[6]Reverse Phase; C18, 44-100% acetonitrile in (10 mM ammonium acetate in 95:5 water:methanol). Enantiomer refers to a clean isomer at the 3-position of the piperidinone.
[7]Prep-Chiral-HPLC; (S,S)-Whelk-O1, 30 × 150 mm, 10-100% ethanol in heptane, 42.5 mL/min. Enantiomer refers to a clean isomer at the 3-position of the piperidinone.
[8]Prep-Chiral-HPLC; Phenomenex Lux Cellulose-1, 30 × 150 mm, 10-85% ethanol in heptane, 37.5 mL/min
[9]Reverse Phase; C18, 41-100% acetonitrile in (10 mM ammonium acetate in 95:5 water:methanol)
[10]Reverse Phase; C18, 41-100% acetonitrile in (10 mM ammonium acetate in 95:5 water:methanol). Diastereomer refers to both a clean atropisomer and a clean isomer at the 3-position of the piperidinone.
[11]Reverse Phase; C18, 40-100% acetonitrile in (10 mM ammonium acetate in 95:5 water:methanol)
[12]Reverse Phase; C18, 37-43% acetonitrile in 10 mM aqueous ammonium bicarbonate. Followed by Reverse Phase; C18, 58-68% methanol in 10 mM aqueous ammonium bicarbonate
[13]Prep-Chiral-HPLC; Chiralpak ID, 30 × 250 mm, 50% ethanol in (10 mM ammoniated methanol in hexanes), 40 mL/min
[14]Prep-Chiral-SFC; (R,R)-Whelk-O1, 30 × 250 mm, 45% (methanol with 10 mM ammonium acetate) in $CO_2$, 85 mL/min
[15]Reverse Phase; C18, 37-100% acetonitrile in (10 mM ammonium acetate in 95:5 water:methanol)
[16]Clean isomer at the 3-position of the piperidinone, chiral purification from Preparation 31A
[17]Reverse Phase; C18, 35-100% acetonitrile in (10 mM ammonium acetate in 95:5 water:methanol)
[18]Prep-Chiral-SFC; Chiralpak ID, 20 × 250 mm, 45% (isopropanol with 0.5% dimethylethylamine) in $CO_2$, 80 mL/min
[19]Prep-Chiral-SFC; Chiralpak IH, 20 × 250 mm, 35% (methanol with 0.5% dimethylethylamine) in $CO_2$, 80 mL/min
[20]Prep-Chiral-SFC; Chiralpak IH, 20 × 250 mm, 35% (methanol with 0.5% dimethylethylamine) in $CO_2$, 80 mL/min
[21]Reverse Phase; C18, 35-100% acetonitrile in (10 mM ammonium acetate in 95:5 water:methanol)

Biological Assays

The following assays demonstrate that the exemplified compounds are potent inhibitors of KRAS G12V and inhibit growth of certain tumors in vitro and/or in vivo.

Cellular Phospho-ERK AlphaLISA® Assay for KRAS Inhibition

The purpose of these assays is to quantify the ability of test compounds to selectively inhibit KRAS signaling in cells with amplified KRAS and expressing activating KRAS G12 mutations (Table 1A). Cancer cell lines used in this study were selected based on the presence of homozygous activating KRAS G12 mutations, or amplification of the KRAS gene.

TABLE 1A

| Cell Line Information | | |
|---|---|---|
| Cell Line Name | RAS Mutation/Features | Assay Seeding Density (Cells/Well) |
| MKN45 | WT KRAS Amplification/ Human Gastric Cancer | 20,000 |
| SW620 | KRAS G12V/Human Colorectal Cancer | 20,000 |

The compounds' activity is determined by measuring changes in the phosphorylation levels of the downstream effector Extracellular Signal-regulated Kinase-1 and 2 (ERK1/2) in the compound treated cells. Phosphorylation levels of ERK-1/2 are measured using the AlphaLISA® SureFire® Ultra™ p-ERK 1/2 (Thr202/Tyr204) Assay Kit (#ALSU-PERK-A50K, PerkinElmer® Waltham, MA). The AlphaLISA® assay is a quantitative sandwich immunoassay that can be used to detect phosphorylation of target proteins from cellular lysates using bead-based Alpha technology. The assay kit contains two antibodies, one that binds the phospho-Thr202/Tyr204 epitope on ERK-1/2, and another one that recognizes a separate site on the protein. One of these antibodies is biotinylated and associated with streptavidin-coated Alpha Donor beads, the other antibody is conjugated to AlphaLISA® Acceptor beads. When ERK-1/2 is phosphorylated in cellular lysate, the Donor and Acceptor beads are brought into proximity with each other. When the Donor bead is excited by 600 nm wavelength light, a photosensitizer inside the bead converts ambient oxygen to an excited singlet state. When the Acceptor bead is within 200 nm of this reaction, the singlet oxygen reacts with the Acceptor leading to a chemiluminescent emission. The amount of light measured is proportional to the amount of phosphorylated ERK-1/2 in the lysate. The AlphaLISA® SureFire® Ultra™ p-ERK 1/2 (Thr202/Tyr204) Assay Kit contains AlphaLISA® antibody-conjugated Donor and Acceptor Beads, Lysis buffer concentrate, and a set of proprietary buffers (Activation Buffer, Reaction Buffer 1, Reaction Buffer 2, and Dilution Buffer).

To perform the assays, test compounds and controls are acoustically dispensed (Labcyte ECHO®, San Jose, CA)

into a white 384-well assay plate (Proxiplate-384, PerkinElmer #6008280) in a 10-point 3-fold dilution series in 30 nL DMSO. Cells are then added to the assay plate in 8 μL per well assay medium (HBSS, Sigma #55021C, 10% FBS, GIBCO #10082-147) at a cell line specific density (Table 1A). The final compound concentrations range from 0.5 to 10,000 nM and the final DMSO concentration is 0.375% in each well. Maximum signal control wells contain 0.375% DMSO only (negative control), and minimum signal control wells contain 10,000 nM control compound (positive control). Cells in suspension are incubated with the test and reference compounds for 2 h at 37° C./5% $CO_2$. Following the 2 h incubation, cells are lysed by adding 2 L of the AlphaLISA® Lysis buffer concentrate (5×) supplemented with protease/phosphatase inhibitor cocktail (Thermo Scientific #78442). The assay plate is covered with an opaque lid and shaken at 750 rpm on a multi-plate shaker (Heidolph, Schwabach, Germany) for 30 min at room temperature to induce cell lysis. During the lysis, the AlphaLISA® Acceptor beads are diluted 1:50 in a prepared buffer mixture (1:1 AlphaLISA® Reaction Buffers 1 and 2 with a 1:25 dilution of AlphaLISA® Activation Buffer). Following cell lysis, plates are centrifuged briefly, and 5 L per well prepared Acceptor beads are added. The plate is then covered and incubated in the dark for 2 h at room temperature. During the Acceptor bead incubation, Donor beads are prepared by diluting the Alpha streptavidin Donor beads 1:50 in AlphaLISA® Dilution buffer. Following the Acceptor bead incubation, 5 L per well of Donor bead mixture is added to the plates. Plates are then covered and allowed to incubate in the dark at room temperature for 2 h. After this incubation period, the AlphaLISA signal is read using a PHERAstar® FSX multimode plate reader (BMG Labtech, Ortenberg, Germany) equipped with an AlphaLISA® compatible optics cube.

Raw signal obtained from the AlphaLISA® assay is analyzed using Genedata Screener® 17.0.3. Within the program, data is normalized to 32 wells treated with inhibition control (max inhibition/positive control) and 32 wells treated with 0.375% DMSO only (minimum inhibition/negative control) to calculate the % Activity of the compound:

$$\%\ \text{Activity} = 100x\left(1 - \frac{(\text{treated value} - \text{positive control})}{(\text{negative control} - \text{positive control})}\right) \quad \text{eq. 1}$$

% Activity values are fit to a four-parameter non-linear logistic equation using Genedata Screener® 17.0.3. to-determine $TC_{50}$ values:

$$y = \text{Bottom} + \frac{\text{Top} - \text{Bottom}}{1 + \left(\frac{10^{Log(IC_{50})}}{10^{x}}\right)^{h}} \quad \text{eq. 2}$$

Where y=% Activity, Bottom=minimum asymptote, Top=maximum asymptote, x=compound concentration, $IC_{50}$=the compound concentration where half maximal activity is achieved, and h=the Hill Coefficient.

Compounds of Examples 1, 2, 4, 7, 8, 11, 12, 15-20, 22, 24, 28-31, 33, 34, 36, 38-40, 42-45, 47-49, 51, 54, 56-59, 61 and 62 were tested in the SW620 Cellular Phospho-ERK AlphaLISA® Assay and exhibited an ability to reduce levels of phosphorylated ERK-1/2 in cells expressing KRAS indicating inhibition of constitutive RAS activity in cells expressing KRAS G12V with a relative IC50 of <50 nM. Compounds of Examples 1-5, 7-9, 11-13, 15-31, 33, 34, 36, 38-49, 51, 54 and 56-62 were tested in both assays above (SW620 and MKN 45 Cellular Phospho-ERK AlphaLISA® Assays) and showed a significant (i.e., greater than 5-fold) selective inhibition preference for KRAS G12V mutant over KRAS wild-type. Further, the compounds of Examples 1, 2, 4, 7, 12, 15-28, 31, 33, 38-40, 42, 43, 45-47, 49, 51, 54 and 57-61 showed a greater than 10-fold selective inhibition preference for KRAS G12V mutant over KRAS wild-type.

This data shows that compounds of Formula I as described herein are potent inhibitors of KRAS human cancer cells expressing KRAS demonstrating the ability to inhibit KRAS G12V mutants with a significant selective inhibition preference for the KRAS G12V mutant over KRAS WT.

CellTiter-Glo® Luminescent Cell Viability Assay for Anti-Proliferative Activity

The purpose of these assays is to quantify the ability of test compounds to selectively inhibit proliferative activity in cells harboring KRAS wild-type (WT) and activating KRAS G12 mutations (Table 1B) grown as tumor spheroids. Cancer cell lines used in this study were selected based on the presence of homozygous activating KRAS G12 mutations, or the KRAS WT gene.

TABLE 1B

| Cell Line Information | | |
|---|---|---|
| Cell Line Name | RAS Mutation/Features | Assay Seeding Density (Cells/Well) |
| MKN45 | KRAS WT/ Human Gastric Cancer | 1,000 |
| SW620 | KRAS G12V/Human Colorectal Cancer | 1,000 |

The compounds' anti-proliferative activity is determined by CellTiter-Glo 2.0 assay which quantifies changes in the cellular levels of ATP in compound treated cells. In the presence of $Mg^{2+}$, ATP and molecular oxygen, Ultra-Glo™ Recombinant Luciferase catalyzes the mono-oxygenation of beetle luciferin and generates light. The luminescence readout is directly proportional to metabolically active cells in culture.

To perform the assays, 75 nL of test compounds, controls, and DMSO are acoustically dispensed using an ECHO 655 Acoustic Liquid Handler (Beckman Life Sciences) into clear round bottom ultra-low attachment spheroid 384-well assay plate (Spheroid Microplates, Corning® #CLS 3830) in a 10-point 3-fold dilution series. The spheroid microplates aid the formation of spheroids in the center of well by inhibiting cellular attachment. A Multidrop Combi Reagent Dispenser (Thermo Fisher Scientific) is used to dispense 40 L/well of cell suspension in microplates containing compounds. Cells (Table 1B) were seeded at a density of 25,000 live cells/mL or 1,000 cells/well in growth medium (RPMI Gibco #11875-093, 10% FBS Gibco #10082-147). The final compound concentrations range from 0.5 to 10,000 nM and the final DMSO concentration is 0.2% in each well. Maximum signal control wells contain 0.2% DMSO only (negative control), and minimum signal control wells contain 10,000 nM control compound (positive control). Plates were sealed with Breathe-Easy® sealing membranes (Diversified Biotech), transferred to a 37° C. incubator with 5% $CO_2$, and allowed to incubate for 4 days.

After 4-day incubation, CTG 2.0 reagent and assay plates were equilibrated at 25° C. for at least 30 minutes. A Multidrop Combi Reagent Dispenser (Thermo Fisher Scientific) was used to dispense 40 μL/well of CTG reagent in microplates. The assay plate was placed on a multi-plate shaker (Heidolph, Schwabach, Germany) at 750 RPM for 10 min at room temperature to induce cell lysis, followed by a 1-minute centrifugation at 1200 RPM. The luminescence was read using a PHERAstar FSX Multimode Plate reader (BMG LABTECH).

Raw luminescence data obtained by CTG assay were analyzed using Genedata Screener® 20.0.5. Within the program, data were normalized to the average signal from 14 wells treated with the positive control (10 mM LY3841814) and the average signal from 14 wells treated with the negative control (0.2% DMSO) to calculate the % Activity of the compound:

$$\%\ \text{Activity} = 100x\left(1 - \frac{(\text{treated value} - \text{positive control})}{(\text{negative control} - \text{positive control})}\right) \quad \text{eq. 1}$$

% Activity values were fit to a four-parameter non-linear regression in Genedata Screener® 20.0.5. to determine IC50 values:

$$y = \text{Bottom} + \frac{\text{Top} - \text{Bottom}}{1 + \left(\frac{10^{Log(IC_{50})}}{10^{x}}\right)^{h}} \quad \text{eq. 2}$$

Where y=% Activity, Bottom=minimum asymptote, Top=maximum asymptote, x=compound concentration, $IC_{50}$=the compound concentration where half maximal activity is achieved, and h=the Hill Coefficient.

Compounds of Examples 1, 2, 4, 7, 8, 11, 12, 15-22, 24, 27-31, 33, 34, 36, 38-40, 43-45, 47-49, 51, 54, 56-59 and 62 were tested in the SW620 4-day 3D proliferation assay and exhibited an ability to reduce ATP levels indicating inhibition of proliferative activity with a relative IC50 of <250 nM. Compounds of Examples 1, 2, 4, 8, 12, 16, 18, 19, 24-31, 33, 36, 38, 39, 42, 44-46, 48, 49, 51, 52, 54, 56-58 and 60-62 were tested in both assays above (SW620 and MKN45 4-day 3D proliferation assays) and showed a greater than 5-fold selective inhibition preference for KRAS G12V mutant over KRAS wild-type.

These data show that compounds of Formula I as described herein are inhibitors of proliferative activity in KRAS tumor spheroids and inhibit KRAS G12V mutant with a selective inhibition preference over KRAS WT.

TABLE 1C

| Abbreviations | |
|---|---|
| KRAS | Kirsten Rat Sarcoma Virus |
| ERK | Extracellular Signal-Regulated Kinase |
| AlphaLISA | Alpha-Linked Immunosorbent Assay |
| DMSO | Dimethyl Sulfoxide |
| HBSS | Hank's Balanced Salt Solution |
| FBS | Fetal Bovine Serum |
| $CO_2$ | Carbon Dioxide |
| ATP | Adenosine triphosphate |
| CTG | CellTiter-Glo |
| RPMI | Roswell Park Memorial Institute |

What is claimed is:

1. A compound of the formula:

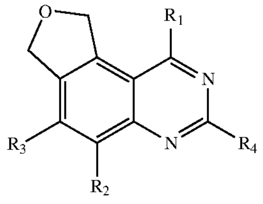

wherein:

$R_1$ is a group of the formula

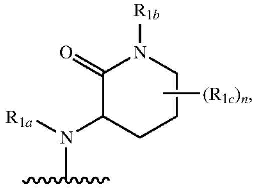

or

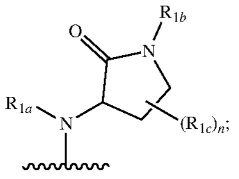

$R_{1a}$ is H or a $C_{1-3}$ alkyl;

$R_{1b}$ is H, $C_{1-3}$ alkyl, or cyclopropyl;

n is 0 or 1;

$R_{1c}$ is a $C_{1-3}$ alkyl;

$R_2$ is H, halogen, or methyl;

$R_3$ is a group of the formula

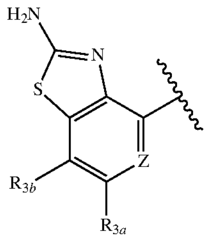

or

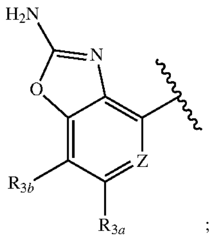

;

Z is —$C(R_{3c})$— or —N—;

$R_{3a}$, $R_{3b}$, and $R_{3c}$ are each independently H, halogen, or methyl;

$R_4$ is a group of the formula selected from

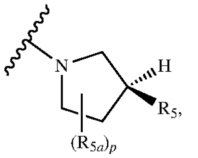

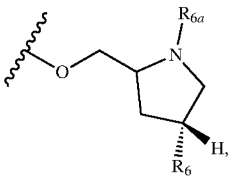

and

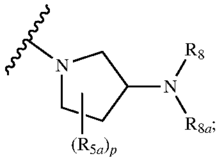

$R_5$ is —$NR_7R_{7a}$;

p is 0 or 1;

$R_{5a}$ and $R_{6a}$ are each independently a $C_{1-3}$ alkyl;
$R_6$ is a halogen or $C_{1-3}$ alkoxy;
$R_7$ is H or a $C_{1-3}$ alkyl; and
$R_{7a}$ is a $C_{1-3}$ alkyl or $C_{1-3}$ alkoxy-$C_{1-3}$ alkyl;
$R_5$ and $R_{5a}$ are each independently a $C_{1-3}$ alkyl; or
$R_5$ and $R_{5a}$ together with the nitrogen atom to which they are attached form an optionally substituted 4-, 5-, or 6-membered heterocycle optionally containing a further heteroatom selected from N, O, and S, wherein the heterocycle is optionally substituted with a $C_{1-3}$ alkyl;
or a pharmaceutically acceptable salt thereof.

2. The compound according to claim 1, wherein:
$R_1$ is a group of the formula

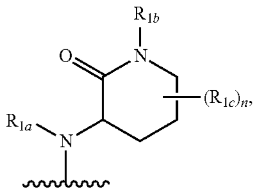 or 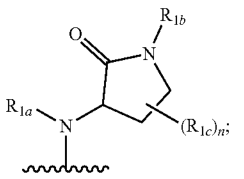

$R_{1a}$ is H, or a $C_{1-3}$ alkyl;
$R_{1b}$ is H, $C_{1-3}$ alkyl, or cyclopropyl;
n is 0, or 1;
$R_{1c}$ is a $C_{1-3}$ alkyl
$R_2$ is H, halogen, or methyl;
$R_3$ is a group of the formula

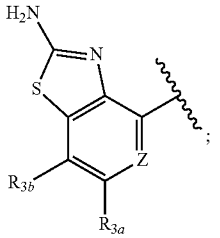

Z is —C($R_{3c}$)— or —N—;
$R_{3a}$, $R_{3b}$, and $R_{3c}$ are each independently H, halogen, or methyl;
$R_4$ is a group of the formula

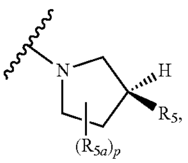 or 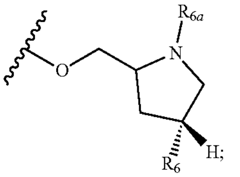

$R_5$ is —$NR_7R_{7a}$;
p is 0 or 1;
$R_{5a}$ and $R_{6a}$ are each independently a $C_{1-3}$ alkyl;
$R_6$ is a halogen;
$R_7$ is H or a $C_{1-3}$ alkyl; and
$R_{7a}$ is a $C_{1-3}$ alkyl; or a pharmaceutically acceptable salt thereof.

3. The compound according to claim 1, wherein $R_3$ is a group of the formula

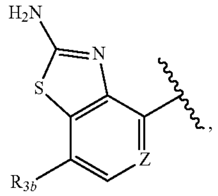

or a pharmaceutically acceptable salt thereof.

4. The compound according to claim 1, wherein $R_3$ is a group of the formula

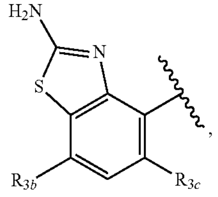

or a pharmaceutically acceptable salt thereof.

5. The compound according to claim 1, wherein $R_3$ is a group of the formula

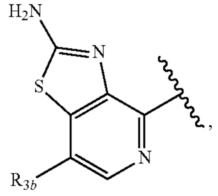

or a pharmaceutically acceptable salt thereof.

6. The compound according to claim 1, wherein $R_3$ is a group of the formula selected from

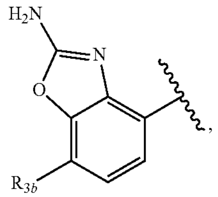

or a pharmaceutically acceptable salt thereof.

7. The compound according to claim 1, wherein $R_3$ is a group of the formula selected from

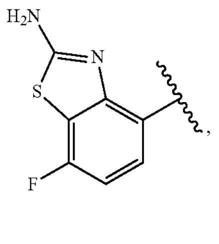 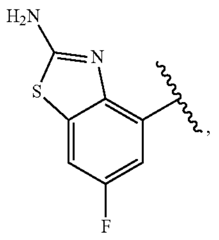

-continued

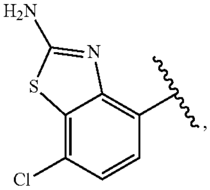,

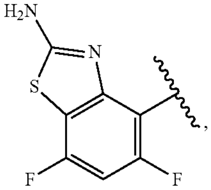,

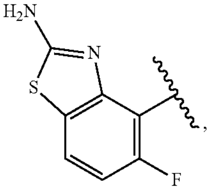,

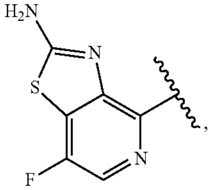,

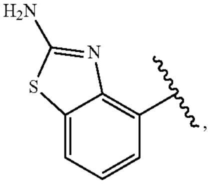,

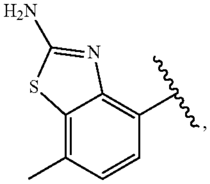, and

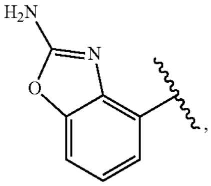, or a pharmaceutically acceptable salt thereof.

8. The compound according to claim 1, wherein $R_3$ is a group of the formula

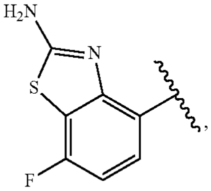,

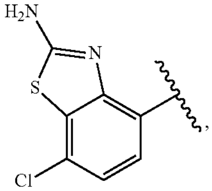,

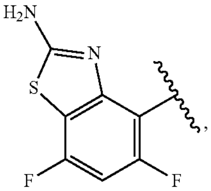,

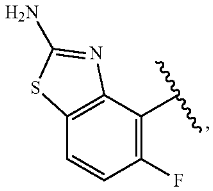, or

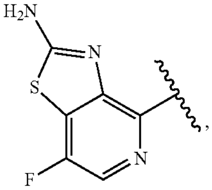, or a pharmaceutically acceptable salt thereof.

9. The compound according to claim 1, wherein $R_2$ is F or Cl, or a pharmaceutically acceptable salt thereof.

10. The compound according to claim 1, wherein $R_1$ is

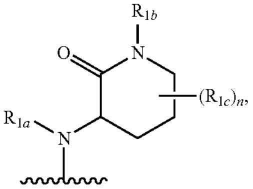

or a pharmaceutically acceptable salt thereof.

11. The compound according to claim 10, wherein $R_1$ is a group of the formula

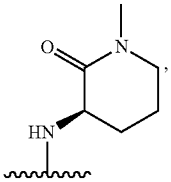,

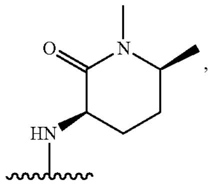, or

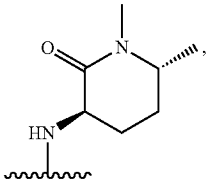, or a pharmaceutically acceptable salt thereof.

12. The compound according to claim 1, wherein $R_{1a}$ is H, or a pharmaceutically acceptable salt thereof.

13. The compound according to claim 1, wherein $R_{1b}$ is a $C_{1-3}$ alkyl, or a pharmaceutically acceptable salt thereof.

14. The compound according to claim 1, wherein n is 0, or a pharmaceutically acceptable salt thereof.

15. The compound according to claim 1, wherein n is 1 and $R_{1c}$ is a $C_{1-3}$ alkyl, or a pharmaceutically acceptable salt thereof.

16. The compound according to claim 1, wherein $R_4$ is a group of the formula selected from

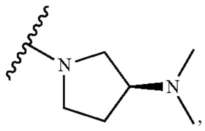,

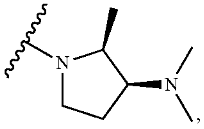,

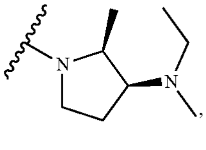,

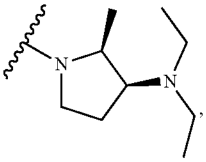,

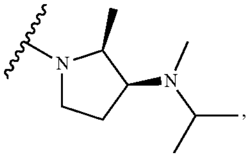,

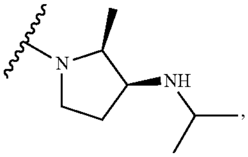,

-continued
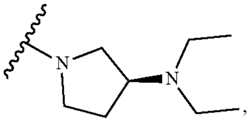,
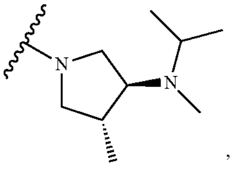,
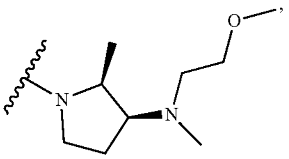
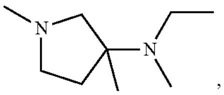,
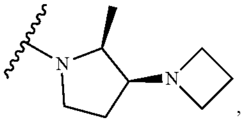,
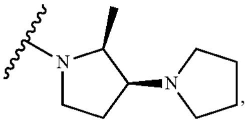,
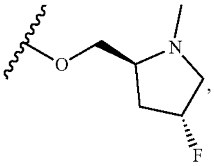,
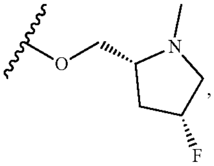, and
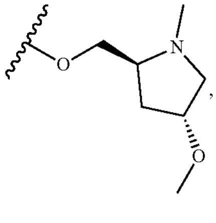,
or a pharmaceutically acceptable salt thereof.
17. The compound according to claim 1, wherein $R_4$ is a group of the formula selected from
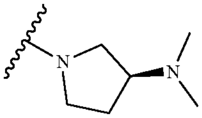,
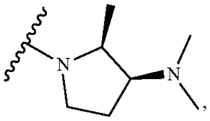,
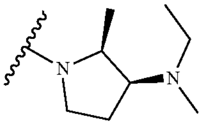,
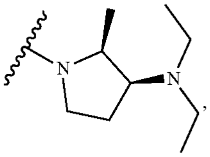,
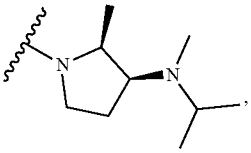,
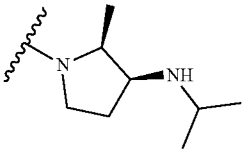,
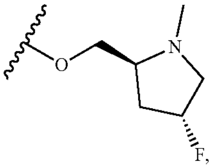, and
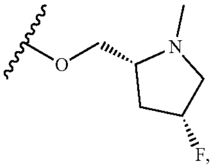,
or a pharmaceutically acceptable salt thereof.
18. The compound according to claim 1, wherein the compound is selected from
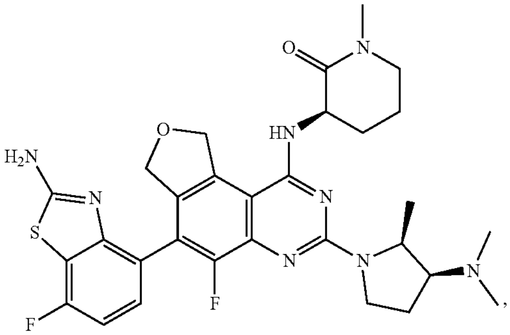,
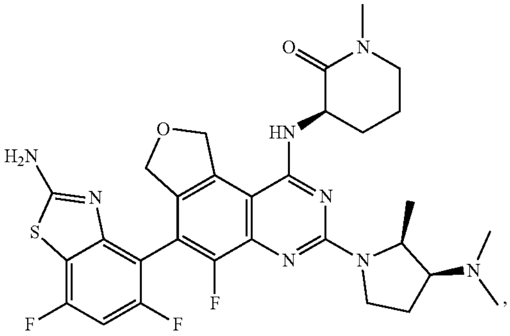,
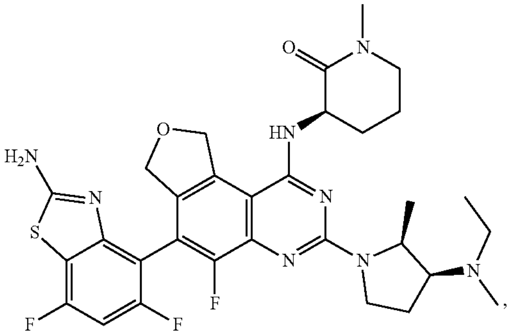,
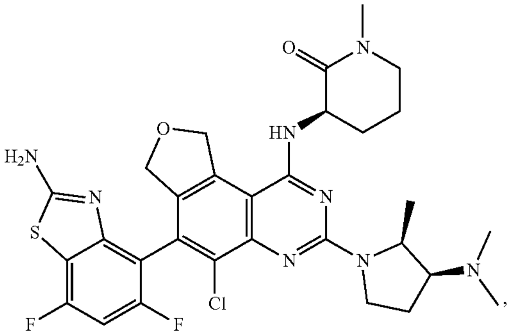,
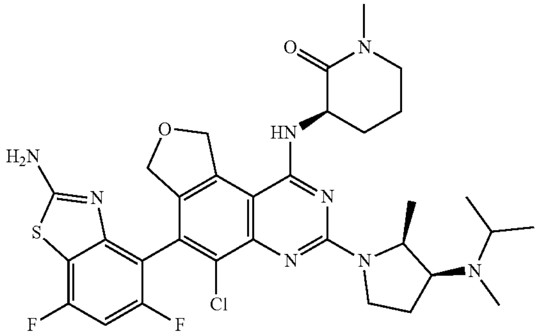, -continued
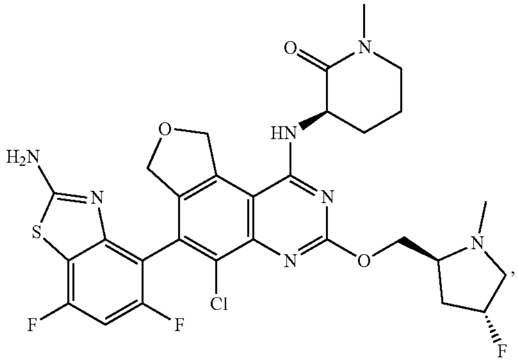,
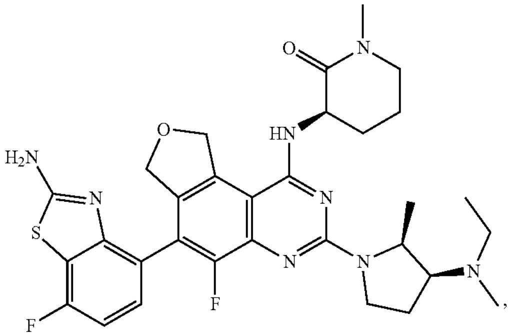,
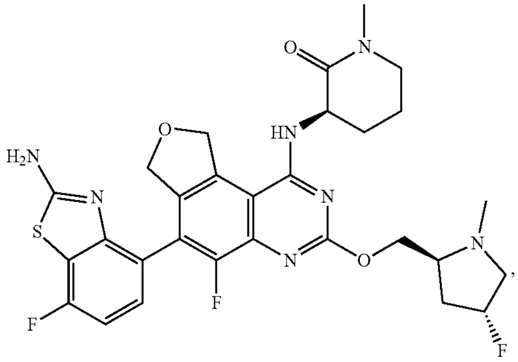,
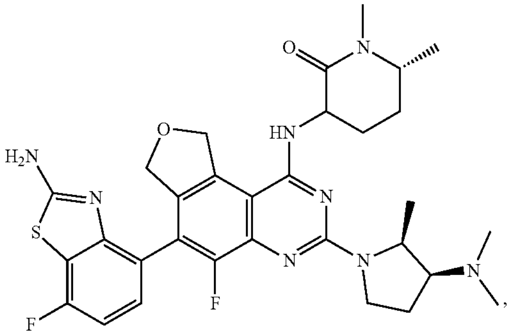,
-continued
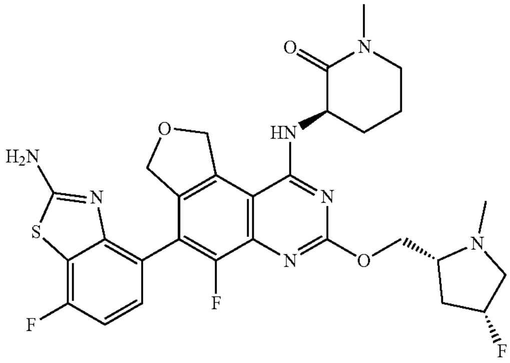,
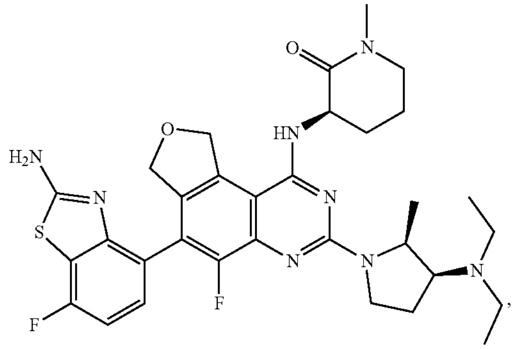,
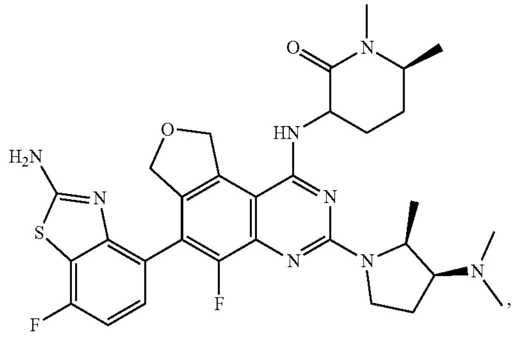,
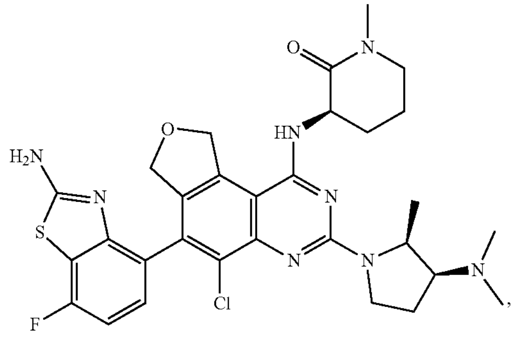,
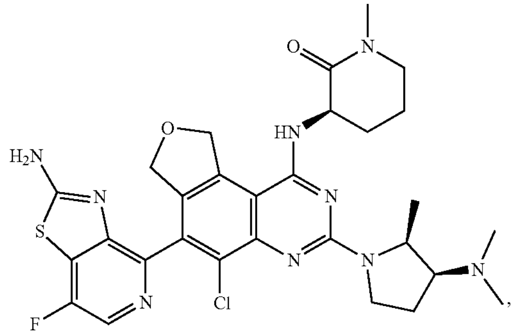, -continued
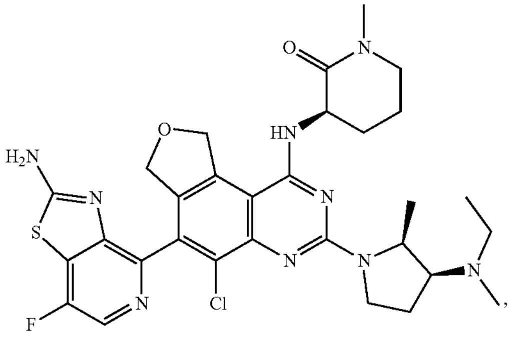
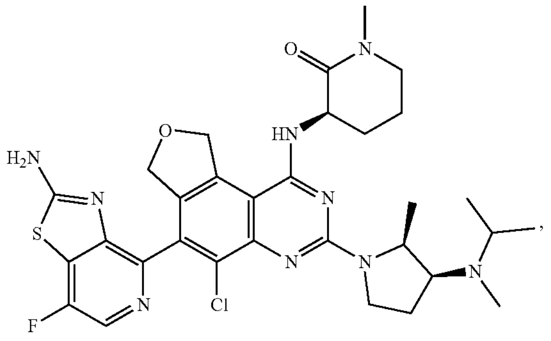
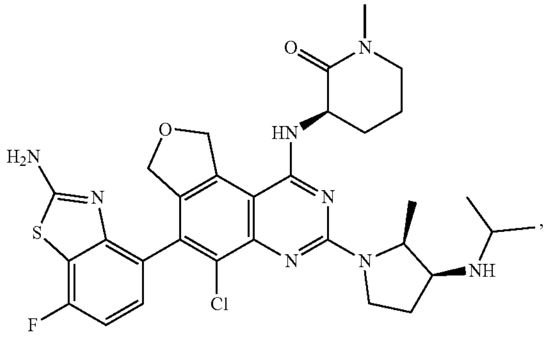
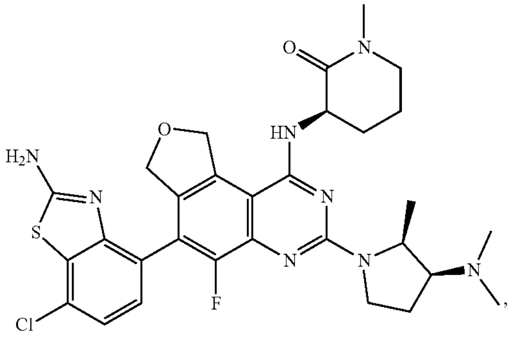
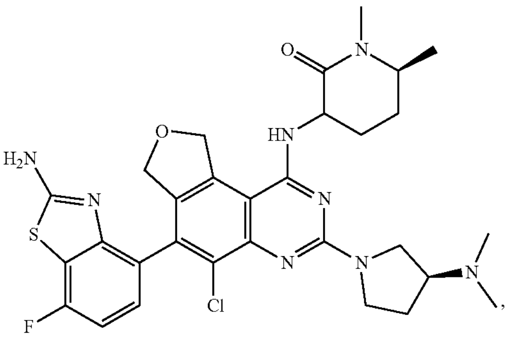
and
-continued
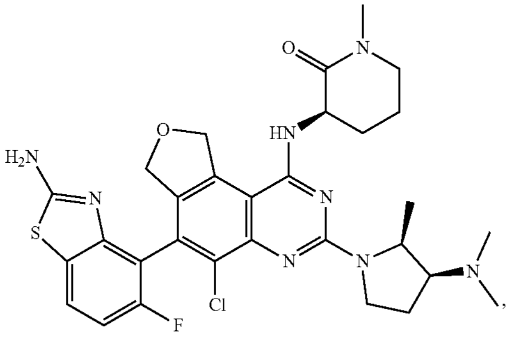
or a pharmaceutically acceptable salt thereof.
19. The compound according to claim 1, wherein the compound is selected from
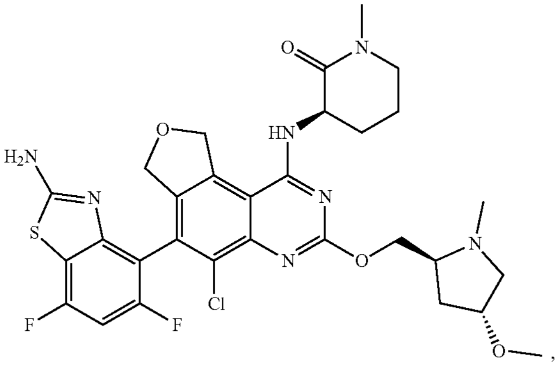
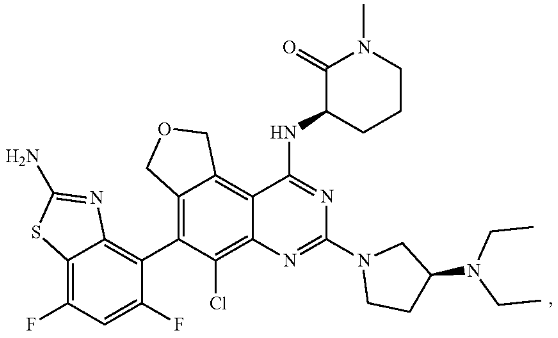
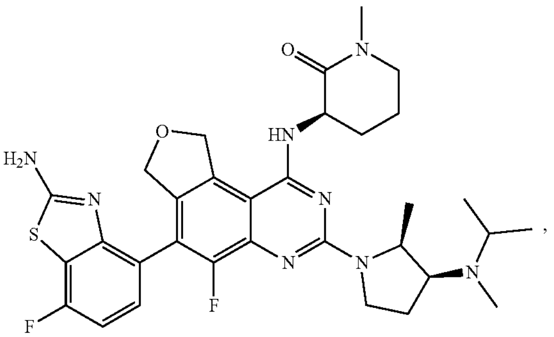

-continued
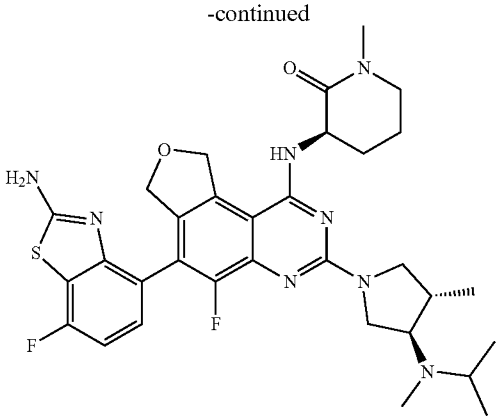
,
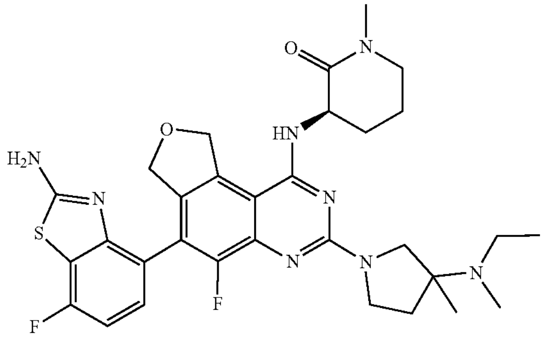
,
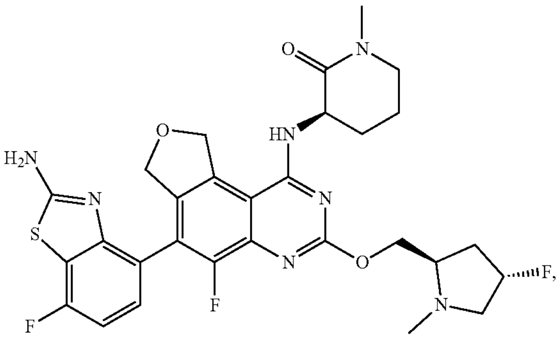
,
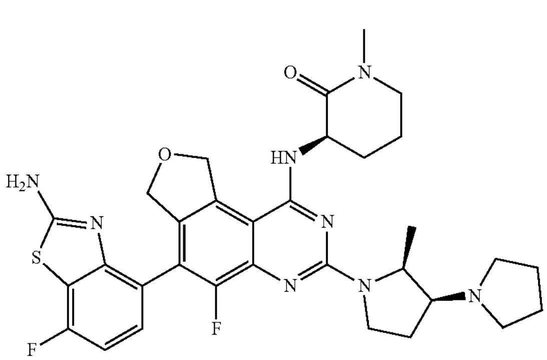
,
-continued
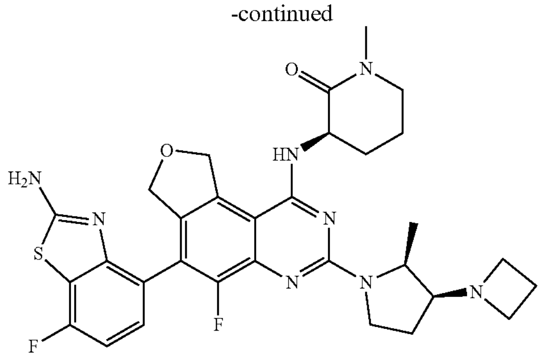
,
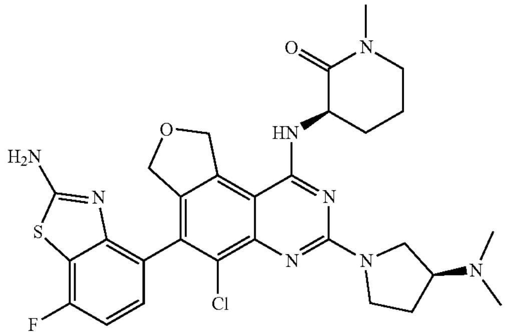
,
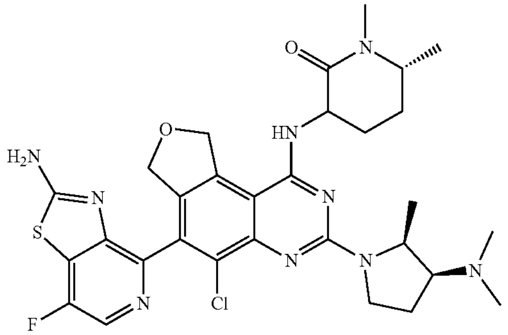
,
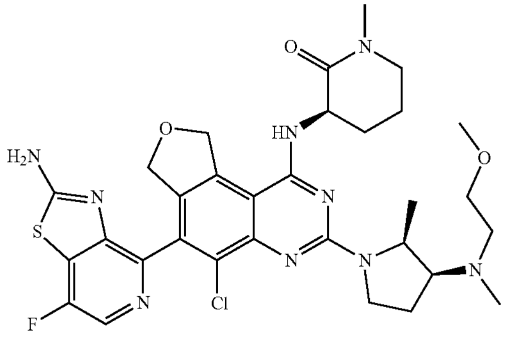
,
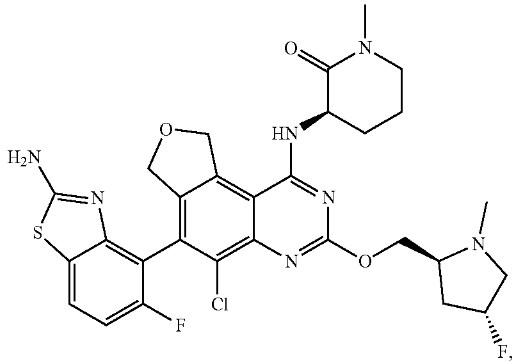
, -continued

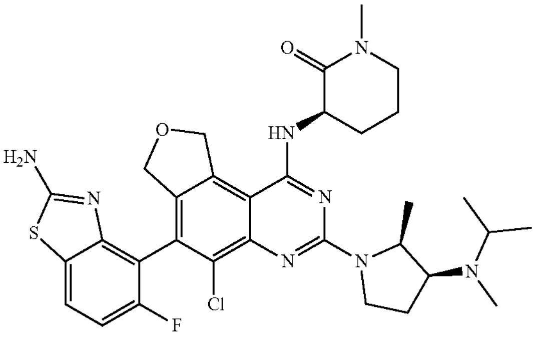

,

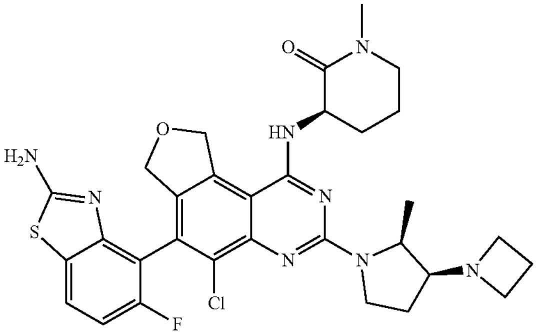

,

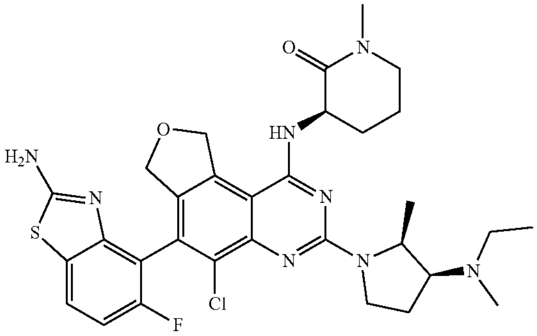

,

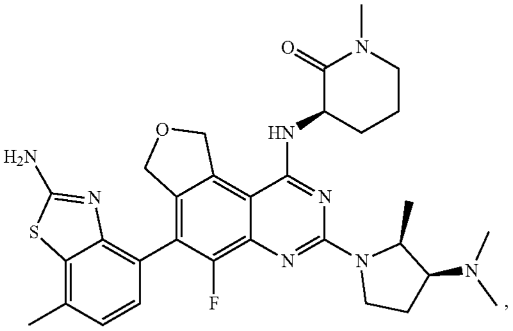

,

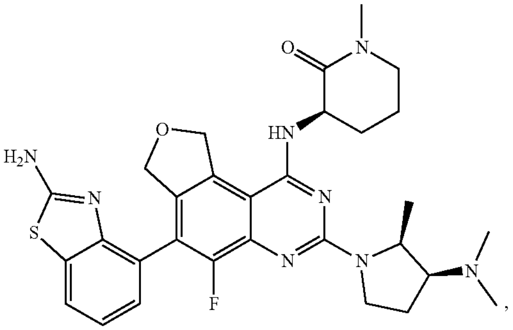

,

-continued

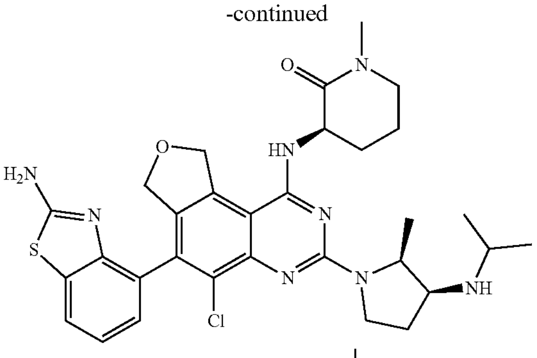

,

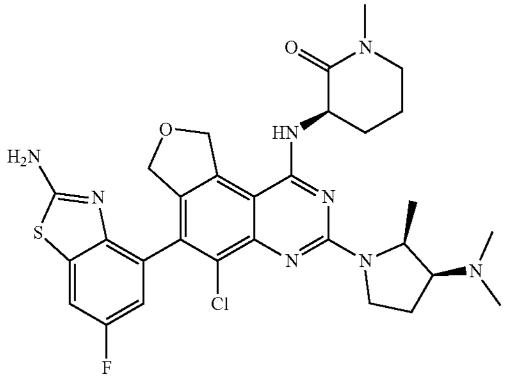

, and

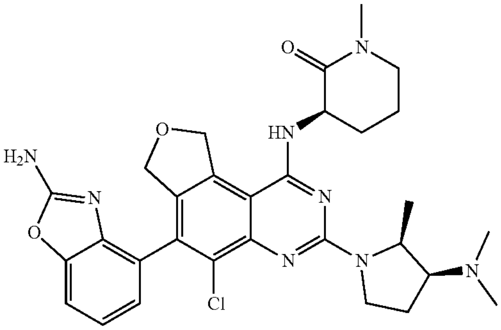

, or a pharmaceutically acceptable salt thereof.

20. A pharmaceutical composition comprising a compound according to claim 1, or a pharmaceutically acceptable salt thereof, and a pharmaceutically acceptable carrier, diluent or excipient.

21. A method of treating a patient with cancer, comprising administering to a patient in need thereof, an effective amount of a pharmaceutical composition according to claim 20, wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

22. A method of treating a patient with cancer, comprising administering to a patient in need thereof, an effective amount of a compound according to claim 1, or a pharmaceutically acceptable salt thereof, wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

23. The method according to claim 22, wherein the patient has a cancer that was determined to have one or more cells expressing the KRAS G12V mutant protein prior to administration of the compound or a pharmaceutically acceptable salt thereof.

24. The method according to claim 22, wherein one or more cells express KRAS G12V mutant protein.

25. A method of treating a patient with a cancer that has a KRAS G12V mutation comprising administering to a patient in need thereof an effective amount of a compound according to claim 1, or a pharmaceutically acceptable salt thereof, and wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

26. The method according to claim 22, wherein the patient is also administered an effective amount of one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof.

* * * * *